US007498407B2

(12) United States Patent
Li et al.

(10) Patent No.: US 7,498,407 B2
(45) Date of Patent: Mar. 3, 2009

(54) VASCULAR ENDOTHELIAL CELL GROWTH INHIBITOR, VEGI-192A

(75) Inventors: Luyuan Li, Pittsburgh, PA (US); Hongguang Pan, Washington, DC (US)

(73) Assignee: Georgetown University, Washington, DC (US)

( * ) Notice: Subject to any disclaimer, the term of this patent is extended or adjusted under 35 U.S.C. 154(b) by 681 days.

(21) Appl. No.: 10/294,249

(22) Filed: Nov. 12, 2002

(65) Prior Publication Data

US 2003/0170242 A1 Sep. 11, 2003

Related U.S. Application Data

(60) Provisional application No. 60/331,190, filed on Nov. 9, 2001.

(51) Int. Cl.
*C07K 1/00* (2006.01)
*C07K 14/435* (2006.01)
*A61K 38/00* (2006.01)
*A61K 38/18* (2006.01)

(52) U.S. Cl. ................. 530/350; 530/355; 530/399; 514/2

(58) Field of Classification Search ................. 530/350
See application file for complete search history.

(56) References Cited

U.S. PATENT DOCUMENTS

| 4,777,127 | A | 10/1988 | Suni et al. |
| 5,219,740 | A | 6/1993 | Miller et al. |
| 5,422,120 | A | 6/1995 | Kim |
| 5,445,934 | A | 8/1995 | Fodor et al. |
| 5,556,752 | A | 9/1996 | Lockhart et al. |
| 5,578,832 | A | 11/1996 | Trulson et al. |
| 5,580,859 | A | 12/1996 | Felgner et al. |
| 5,593,839 | A | 1/1997 | Hubbell et al. |
| 5,599,695 | A | 2/1997 | Pease et al. |
| 5,631,734 | A | 5/1997 | Stern et al. |
| 5,744,305 | A | 4/1998 | Fodor et al. |
| 5,807,522 | A | 9/1998 | Brown et al. |
| 5,814,482 | A | 9/1998 | Dubensky, Jr. et al. |
| 6,146,848 | A | 11/2000 | Wong et al. |
| 2001/0044521 | A1 | 11/2001 | Lin |
| 2002/0037851 | A1 | 3/2002 | Fleckenstein et al. |
| 2002/0111325 | A1 | 8/2002 | Li et al. |

FOREIGN PATENT DOCUMENTS

| EP | 0 345 242 | 12/1989 |
| EP | 0 524 968 | 2/1993 |
| EP | 721 016 | 7/1996 |
| EP | 728 520 | 8/1996 |
| EP | 785 280 | 7/1997 |
| EP | 799 897 | 10/1997 |
| EP | 0 892 047 A2 | 1/1999 |
| EP | 0 892 047 A3 | 1/1999 |
| GB | 2200651 | 8/1988 |
| WO | WO 90/07936 | 7/1990 |
| WO | WO 90/11092 | 10/1990 |
| WO | WO 90/15070 | 12/1990 |
| WO | WO 91/02805 | 3/1991 |
| WO | WO 91/14445 | 10/1991 |
| WO | WO 93/03769 | 3/1993 |
| WO | WO 93/10218 | 5/1993 |
| WO | WO 93/11230 | 6/1993 |
| WO | WO 93/19191 | 9/1993 |
| WO | WO 93/25234 | 12/1993 |
| WO | WO 93/25698 | 12/1993 |
| WO | WO 94/03622 | 2/1994 |
| WO | WO 94/12649 | 6/1994 |
| WO | WO 94/23697 | 10/1994 |
| WO | WO 94/28938 | 12/1994 |
| WO | WO 95/00655 | 1/1995 |
| WO | WO 95/07994 | 3/1995 |
| WO | WO 95/11984 | 5/1995 |
| WO | WO 95/11995 | 5/1995 |
| WO | WO 95/13796 | 5/1995 |
| WO | WO 95/22058 | 8/1995 |
| WO | WO 95/30763 | 11/1995 |
| WO | WO 96/14328 | 5/1996 |
| WO | WO 96/17072 | 6/1996 |
| WO | WO 97/02357 | 1/1997 |
| WO | WO 97/10365 | 3/1997 |
| WO | WO 97/27317 | 7/1997 |
| WO | WO 97/29212 | 8/1997 |
| WO | WO 97/42338 | 11/1997 |
| WO | WO 99/23105 | 5/1999 |
| WO | WO 00/08136 | 2/2000 |
| WO | WO 00/66608 | 11/2000 |
| WO | WO 01/55174 | 8/2001 |
| WO | WO 02/077036 | 10/2002 |
| WO | WO 03/039491 | 5/2003 |

OTHER PUBLICATIONS

Freshney (Culture of Animal Cells, A Manual of Basic Technique, Alan R. Liss, Inc., 1983, New York, p. 4).*
EMBL-EBI. (Aug. 16, 2000). "*Homo sapiens* 3 BAC RP11-486023 (Roswell Park Cancer Institute Human BAC Library) Complete Sequence," Database Accession No. AC078982, located at <http://www.ebi.ac.uk/cgi-bin/emblfetch?style=html&id=AC078982 &Submit=Go>, last visited on Feb. 6, 2006, 13 pages.
Supplemental European Search Report mailed Nov. 16, 2005 for European Patent Application No. 02793986.7, 6 pages.
EMBL Database Accession No. AL390240. "Human DNA Sequence from Clone RP11-428F18 on Chromosome 9 Contains the TNFSF15 Gene for the Tumor Necrosis Factor (Ligand) Superfamily, Member 15 (TL1, VEG1)," created Jul. 21, 2000, located at <http://www.ebi.ac.uk/cgi-bin/emblfetch?style=html&id=AL390240&Submit=Go, last visited on Aug. 1, 2005, 27 pages.

(Continued)

*Primary Examiner*—Karen A Canella
*Assistant Examiner*—Peter J Reddig
(74) *Attorney, Agent, or Firm*—Morrison & Foerster LLP

(57) ABSTRACT

This invention discloses two new VEGI isoforms named VEGI-$_{192a}$ and VEGI-$_{192b}$ consisting of 192 amino acid residues. These isoforms show endothelial cell-specific expression and share a C-terminal 151-residues segment with the previously described VEGI-$_{174}$ and VEGI-$_{251}$. Methods of using these isoforms of VEGI in diagnosing, screening agonist and antagonist of the isoforms, and treating various angiogenesis-related diseases are also disclosed.

10 Claims, 25 Drawing Sheets

OTHER PUBLICATIONS

Wang, L. et al. (2000). "Cloning, Expression and Biological Activity of VEGI$_{151}$, a Novel Vascular Endothelial Cell Growth Inhibitor," *Acta Biochimica et Biophysica Sinica* 32(5):485-489, English Abstract, one page.

Xiao, Y. et al. (2001). "Anti-Angiogenesis of Recombinant Human Soluble Vascular Endothelial Growth Inhibitor (VEGI)," *Pharmaceutical Biotechnology* 8(1):17-21, English Abstract, one page.

GenBank Accession No. AF039390, Jan. 22, 1999, located at <http://www.ncbi.nlm.nih.gov/entrez/query.fcgi?cmd=Retrieve&db=nucleotide&list>, last visited on Apr. 17, 2003, 2 pages.

GenBank Accession No. NT_017568, Apr. 10, 2003, located at <http://www.ncbi.nlm.nih.gov/entrez/query.fcgi?cmd=Retrieve&db=nucleotide&list>, last visited on Apr. 17, 2003, 29 pages.

Aggarwal, B.B. and Natarajan, K. (1996). "Tumor Necrosis Factors: Developments During the Last Decade," *Eur. Cytokine News* 7(2):93-124.

Altamirano, C.V. et al. (2001). "Vascular Endothelial Growth Inhibitor (VEGI) Inhibits the Growth of Multiple Myeloma Plasma Cells and Induces Their Apoptosis," *Blood* 98(11/1):638a. Abstract No. 2672.

Ausubel, F.M. et al. eds. (1987). *Current Protocols in Molecular Biology* vol. 1, Supplement 30:7.7.17-7.7.19. Table 7.7.1., five pages.

Baldwin, H.S. (1996). "Early Embryonic Vascular Development," *Cardiovasc. Res.* 31:E34-45.

Beal, P.A. and Dervan, P.B. (1991). "Second Structural Motif for Recognition of DNA by Oligonucleotide-Directed Triple-Helix Formation," *Science* 251:1360-1363.

Boldrini, L. et al. (2000). "Tumour Necrosis Factor-α and Transforming Growth Factor-β are Significantly Associated with Better Prognosis in Non-Small Cell Lung Carcinoma: Putative Relation with BCL-2-Mediated Neovascularization," *Brit. J. Cancer.* 83(4):480-486.

Burrus, L.W. and Olwin, B.B. (1989). "Isolation of a Receptor for Acidic and Basic Fibroblast Growth Factor from Embryonic Chick," *J. Biol. Chem.* 264(31):18647-18653.

Chalfant, C.E. et al. (1995). "Regulation of Alternative Splicing of Protein Kinase Cβ by Insulin," *J. Biol. Chem.* 270(22):13326-13332.

Chew, L-J. et al. (2002). "A Novel Secreted Splice Variant of Vascular Endothelial Cell Growth Inhibitor," *The FASEB Journal* 27 pages.

Chiou, H.C. et al. (1994). "In Vivo Gene Therapy via Receptor-Mediated DNA Delivery" *In Gene Therapeutics: Methods and Applications of Direct Gene Transfer* Wolff, J.A. ed. Birkhauser: Boston, MA pp. 143-156.

Chomczynski, P. and Sacchi, N. (1987). "Single-Step Method of RNA Isolation by Acid Guanidinium Thiocyanate-Phenol-Chloroform Extraction," *Anal. Biochem.* 162:156-159.

Cohen, J. S. ed. (1989). *Oligodeoxynucleotides as Antisense Inhibitors of Gene Expression* CRC Press: Boca Raton, FL. pp. v.-viii. (Table of Contents Only.).

Cok, S.J. and Morrison, A.R. (2001). "The 3'-Untranslated Region of Murine Cyclooxygenase-2 Contains Multiple Regulatory Elements That Alter Message Stability and Translational Efficiency," *J. Biol. Chem.* 276(25):23179-23185.

Connelly, S. et al. (1995). "In Vivo Gene Delivery and Expression of Physiological Levels of Functional Human Factor VIII in Mice," *Human Gene Therapy* 6:185-193.

Cooney, M. et al. (1988). "Site-Specific Oligonucleotide Binding Represses Transcription of the Human c-*myc* Gene in Vitro," *Science* 241:456-459.

Curiel, D.T. (1992). "High-Efficiency Gene Transfer Mediated by Adenovirus Coupled to DNA-Polylysine Complexes," *Human Gene Therapy* 3:147-154.

Darnay, B.G. and Aggarwal, B.B. (1999). "Signal Transduction by Tumour Necrosis Factor and Tumour Necrosis Factor Related Ligands and Their Receptors," *Annals of the Rheumatic Diseases* 58(Supp.1)I2-I13.

Derrigo, M. et al. (2000). "RNA-Protein Interactions in the Control of Stability and Localization of Messenger RNA," *Int. J. Mol. Med.* 5(2):111-123.

deVries, C. et al. (1992). "The *fms*-Like Tyrosine Kinase, a Receptor for Vascular Endothelial Growth Factor," *Science* 255:989-991.

Dull, T. et al. (1998). "A Third-Generation Lentivirus Vector With a Conditional Packaging System," *J. Virol.* 72(11):8463-8471.

Eissa, N.T. et al. (1996). "Alternative Splicing of Human Inducible Nitric-Oxide Synthase mRNA: Tissue-Specific Regulation and Induction by Cytokines," *J. Biol. Chem.* 271(43):27184-27187.

Engerman, R.L. et al. (1967). "Cell Turnover of Capillaries," *Lab. Invest.* 17(6):738-743.

Fajardo, L.F. et al. (1992). "Dual Role of Tumor Necrosis Factor-α in Angiogenesis," *Am. J. Pathol.* 140(3):539-544.

Findeis, M.A. et al. (1993). "Targeted Delivery of DNA for Gene Therapy Via Receptors," *TIB Tech* 11:202-205.

Folkman, J. (1995). "Angiogenesis in Cancer, Vascular, Rheumatoid and Other Disease," *Nature Medicine* 1(1):27-31.

Folkman, J. (1995). "Clinical Applications of Research on Angiogenesis," *New Eng. J. Med.* 333(26):1757-1763.

Frater-Schröder, M. et al. (1987). "Tumor Necrosis Factor Type α, a Potent Inhibitor of Endothelial Cell Growth in vitro, is Angiogenic in vivo," *Proc. Natl. Acad. Sci. USA* 84:5277-5281.

Gacesa, P. and Ramji, D.P. (1994). *Vectors: Essential Data* Rickwood, D. and Hames, B.D. eds. John Wiley & Sons: Chichester, West Sussex, England. pp. v-ix. (Table of Contents Only.).

Gennaro, A.R. ed. (2000). *Remington: The Science and Practice of Pharmacy* 20th Edition. Lippincott, Williams and Wilkins, pp. xiv-xv. (Table of Contents Only.).

Gimenez-Gallego, G. et al. (1985). "Brain-Derived Acidic Fibroblast Growth Factor: Complete Amino Acid Sequence and Homologies," *Science* 230:1385:1388.

Good, D.J. et al. (1990). "A Tumor Suppressor-Dependent Inhibitor of Angiogenesis is Immunologically and Functionally Indistinguishable From a Fragment of Thrombospondin," *Proc. Natl. Acad. Sci. U.S.A.* 87:6624-6628.

Hanahan, D. and Folkman, J. (1996). "Patterns and Emerging Mechanisms of the Angiogenic Switch During Tumorigenesis," *Cell* 86:353-364.

Haridas, V. et al. (1999). "VEGI, a New Member of the TNF Family Activates Nuclear Factor-κB and c-Jun N-terminal Kinase and Modulates Cell Growth," *Oncogene* 18:6496-6504.

He, Y. et al. (1999). "Alternative Splicing of Vascular Endothelial Growth Factor (VEGF)-R1 (FLT-1) pre-mRNA is Important for the Regulation of VEGF Activity," *Mol. Endocrinol.* 13(4):537-545.

Hein, J. (1990). "Unified Approach to Alignment and Phylogenies" Chapter 39 *In Methods in Enzymology* Academic Press, Inc. vol. 183, pp. 626-645.

Higgins, D.G. and Sharp, P.M. (1988). "Clustal: A Package for Performing Multiple Sequence Alignment on a Microcomputer," *Gene* 73:237-244.

Hohlbaum, A.M. et al. (2000). "Opposing Effects of Transmembrane and Soluble Fas Ligand Expression on Inflammation and Tumor Cell Survival," *J. Exp. Med.* 191(7):1209-1219.

Holash, J. et al. (1999). "New Model of Tumor Angiogenesis: Dynamic Balance Between Vessel Regression and Growth Mediated by Angiopoietins and VEGF," *Oncogene* 18:5356-5362.

Horrevoets, A.J.G. et al. (1999). "Vascular Endothelial Genes That Are Responsive To Tumor Necrosis Factor-α In Vitro Are Expressed In Atherosclerotic Lesions, Including Inhibitor of Apoptosis Protein-1, Stannin, and Two Novel Genes," *Blood* 93(10):3418-3431.

Hu, S. et al. (1999). "Characterization of TNFRSF19, A Novel Member of the Tumor Necrosis Factor Receptor Superfamily," *Genomics* 62:103-107.

Huang, W-Q. et al. (2000). "Inhibition of Breast Cancer Xenograft Tumorigenesis by VEGI, and Endothelial Cell-Specific Anti-Angiogenic Cytokine of the TNF Superfamily," *Proceedings of the 91st Annual Meeting of the American Association for Cancer Research*: San Francisco, CA. vol. 41, p. 647. Abstract No. 4109.

Jackson, D. et al. (1994). "Stimulation and Inhibition of Angiogenesis by Placental Proliferin and Proliferin-Related Protein," *Science* 266:1581-1584.

Jacobson, A. and Peltz, S.W. (1996). "Interrelationships of the Pathways of mRNA Decay and Translation in Eukaryotic Cells," *Ann. Rev. Biochem.* 65:693-739.

Jalkanen, M. et al. (1985). "Heparan Sulfate Proteoglycans From Mouse Mammary Epithelial Cells: Localization on the Cell Surface with a Monoclonal Antibody," *J. Cell. Biol.* 101:976-984.

Jalkanen, M. et al. (1987). "Cell Surface Proteoglycan of Mouse Mammary Epithelial Cells Is Shed by Cleavage of Its Matrix-binding Ectodomain from Its Membrane-Associated Domain," *J. Cell Biol.* 105(6/2):3087-3096.

Jolly, D. (1994). "Viral Vector Systems For Gene Therapy," *Cancer Gene Therapy* 1(1):51-64.

Kaplitt, M.G. (1994). "Long-Term Gene Expression and Phenotypic Correction Using Adeno-Associated Virus Vectors in the Mammalian Brain," *Nature Genetics* 8:148-154.

Kimura, O. et al. (1994). "Retroviral Delivery of DNA into the Livers of Transgenic Mice Bearing Premalignant and Malignant Hepatocellular Carcinomas," *Human Gene Therapy* 5:845-852.

Kwon, B. and Kwon, B.S. (1999). "Molecules of the Tumor Necrosis Factor (TNF) Receptor and Ligand Superfamilies: Endless Stories," *J. Biochem. Mol. Bio.* 32(4):419-428.

Lee, J.S. et al. (1979). "Complexes Formed by $(Pyrimidine)_n$ $(Purine)_n$ DNAs on Lowering the pH Are Three-Stranded," *Nucleic Acids Research* 6(9):3073-3091.

Leek, R.D. et al. (1994). "Cytokine Networks in Solid Human Tumors: Regulation of Angiogenesis," *J. Leukoc. Biol.* 56:423-435.

Leung, D.W. et al. (1989). "Vascular Endothelial Growth Factor Is a Secreted Angiogenic Mitogen," *Science* 246:1306-1309.

Li, L. (1999). "A Novel Negative Regulator of Angiogenesis," *NTIS Annual Report* (Aug. 1, 1998-Jul. 31, 1999). pp. 1-12 without appendices.

Li, L-Y. et al. (1994). "Diminished Heparin Binding of a Basic Fibroblast Growth Factor Mutant Is Associated with Reduced Receptor Binding, Mitogenesis, Plasminogen Activator Induction, and in Vitro Angiogenesis," *Biochemistry* 33:10999-11007.

Lou, H. and Gagel, R.F. (2001). "Alternative Ribonucleic Acid Processing in Endocrine Systems," *Endocrine Rev.* 22(2):205-225.

Maione, T.E. et al. (1997). "Inhibition of Angiogenesis by Recombinant Human Platelet Factor-4 and Related Peptides," *Science* 247:77-79.

McGeehan, G.M. et al. (1994). "Regulation of Tumour Necrosis Factor-α Processing by a Metalloproteinase Inhibitor," *Nature* 370:558-561.

McKay, N.G. et al. (1994). "Regulation of Alternative Splicing of the Fibronectin IICS Domain by Cytokines," *Biochem Biophys. Res. Commun.* 199(2):1005-1011.

McKusick, V.A. et al. eds. (1992). *Mendelian Inheritance in Man: Catalogs of Autosomal Dominant, Autosomal Recessive, and X-Linked Phenotypes* The Johns Hopkins University Press. Tenth Edition, four pages (Table of Contents Only.).

Metheny, L.J. and Skuse, G.R. (1996). "NF1 mRNA Isoform Expression in PC12 Cells: Modulation by Extrinsic Factors," *Exp. Cell. Res.* 228:44-49.

Metheny-Barlow, L. et al. (2001). "Modulation of Endothelial Cell Growth Cycle by VEGI: Possible Role of NFκB," *Proceedings of the 92nd Annual Meeting of the American Association for Cancer Research*: New Orleans, LA vol. 42, p. 941. Abstract No. 5058.

Metheny-Barlow, L.J. et al. (2002). "Activation of Distinct Signaling Pathways in Proliferating Versus Quiescent Endothelial Cells in Response to VEGI," *Proceedings of the 93rd Annual Meeting of the American Association For Cancer Research*: San Francisco, CA vol. 43, p. 34. Abstract No. 173.

Migone, T-S. et al. (2002). "TL1A Is a TNF-like Ligand for DR3 and TR6/DcR3 and Functions as a T Cell Costimulator," *Immunity* 16:479-492.

Miller, A.D. (1990). "Retrovirus Packaging Cells," *Human Gene Therapy* 1:5-14.

Miller, A.D. and Rosman, G. J. (1989). "Improved Retroviral Vectors for Gene Transfer and Expression," *Biotechniques* 7(9):980-990.

Montesano, R. and Orci, L. (1985). "Tumor-Promoting Phorbol Esters Induce Angiogenesis In Virto," *Cell* 42:469-477.

Mueller, C. et al. (1999). "Noncleavable Transmembrane Mouse Tumor Necrosis Factor-α (TNFα) Mediates Effects Distinct from Those of Wild-Type TNFα in Vitro and in Vivo," *J. Biol. Chem.* 274(53):38112-38118.

Naldini, L. et al. (1996). "Efficient Transfer, Integration, and Sustained Long-Term Expression of the Transgene in Adult Rat Brains Injected with a Lentiviral Vector," *Proc. Natl. Acad. Sci. USA* 93:11382-11388.

Naldini, L. et al. (1996). "In Vivo Gene Delivery and Stable Transduction of Nondividing Cells by a Lentiviral Vector," *Science* 272:263-267.

Nguyen, M. et al. (1994). "Quantitation of Angiogenesis and Antiangiogenesis in the Chick Embryo Chorioallantoic Membrane," *Microvasc. Res.* 47:31-40.

Okano, H. et al. (1991). "Myelin Basic Protein Gene and the Function of Antisense RNA in Its Repression in Myelin-Deficient Mutant Mouse," *Journal of Neurochemistry* 56(2):560-567.

Ono, Y. et al. (1999). "Apoptosis, Coronary Arterial Remodeling, and Myocardial Infarction After Nitric Oxide Inhibition in SHR," *Hypertension* 34:609-616.

O'Reilly, M.S. et al. (1994). "Angiostatin: A Novel Angiogenesis Inhibitor That Mediates the Suppression of Metastases by a Lewis Lung Carcinoma," *Cell* 79:315-328.

O'Reilly, M.S. et al. (1997). "Endostatin: An Endogenous Inhibitor of Angiogenesis and Tumor Growth," *Cell* 88:277-285.

Pan, H. et al. (2000). "Identification of a Secreted Form of VEGI, an Endothelial Cell-Specific Antiangiogenic Factor Involved in Negative Regulation of Endothelial Cell Proliferation," *Proceedings of the 91st Annual Meeting of the American Association for Cancer Research*: San Francisco, CA vol. 41, p. 646. Abstract No. 4107.

Pappalardo, P.A. et al. (1998). "Microdissection, Microchip Arrays, and Molecular Analysis of Tumor Cells (Primary and Metastases)," *Sem. Radiation Oncol.* 8(3):217-223.

Patterson, C. et al. (1996). "Downregulation of Vascular Endothelial Growth Factor Receptors by Tumor Necrosis Factor-α in Cultured Human Vascular Endothelial Cells," *J. Clin. Invest.* 98(2):490-496.

Philip, R. et al. (1994). "Efficient and Sustained Gene Expression in Primary T Lymphocytes and Primary and Cultured Tumor Cells Mediated by Adeno-Associated Virus Plasmid DNA Complexed to Cationic Liposomes," *Mol. Cell. Biol.* 14(4):2411-2418.

Pollman, M.J. et al. (1999). "Endothelial Cell Apoptosis in Capillary Network Remodeling," *J. Cell Physiol.* 178:359-370.

Ramsay, G. (1998). "DNA Chips: State-of-the Art," *Nature Biotechnol.* 15:40-44.

Rio, D.C. (1993). "Splicing of Pre-mRNA: Mechanism, Regulation and Role in Development," *Curr. Opin. Genet. Dev.* 3:574-584.

Sambrook, J. et al. eds. (1989). *Molecular Cloning: A Laboratory Manual* Second Edition pp. xi-xxxviii. (Table of Contents Only.).

Schena, M. et al. (1995). "Quantitative Monitoring of Gene Expression Patterns with a Complementary DNA Microarray," *Science* 270:467-470.

Schena, M. et al. (1996). "Parallel Human Genome Analysis: Microarray-Based Expression Monitoring of 1000 Genes," *Proc. Natl Acad. Sci.USA* 93:10614-10619.

Schneider, P. et al. (1998). "Conversion of Membrane-Bound Fas(CD95) Ligand to Its Soluble Form Is Associated With Downregulation of Its Proapoptotic Activity and Loss of Liver Toxicity," *J. Exp. Med.* 187(8):1205-1213.

Schweigerer, L. et al. (1987). "Capillary Endothelial Cells Express Basis Fibroblast Growth Factor, A Mitogen That Promotes Their Own Growth," *Nature* 325:257:259.

Shalon, D. et al. (1996). "A DNA Microarray System for Analyzing Complex DNA Samples Using Two-Color Fluorescent Probe Hybridization," *Genome Res.* 6:639-645.

Shifrin, V.I. and Neel, B.G. (1993). "Growth Factor-Inducible Alternative Splicing of Nontransmembrane Phosphotyrosine Phosphatase PTP-1B Pre-mRNA," *J. Biol. Chem.* 268(34):25376-25384.

Shudo, K. et al. (2000). "Membrane-Bound But Not the Soluble Form of Human Fas Ligand is Responsible for its Inflammatory Activity," *Eur. J. Immunol.* 31:2504-2511.

Stewart, S.A. et al. (1999). "Lentiviral Delivery of HIV-1 Vpr Protein Induces Apoptosis in Transformed Cells," *Proc. Natl. Acad. Sci. USA* 96(21):12039-12043.

Tanaka, M. et al. (1995). "Expression of the Functional Soluble Form of Human Fas Ligand in Activated Lymphocytes," *EMBO J.* 14(6):1129-1135.

Terman, B.I. et al. (1992). "Identification of the KDR Tyrosine Kinase As A Receptor For Vascular Endothelial Cell Growth Factor," *Biochem. Biophys. Res. Comm.* 187(3):1579-1586.

Verma, R.S. and Babu, A. eds. (1988). *Human Chromosomes: Manual of Basic Techniques* Pergamon Press: Elmsford, New York. pp. vii-ix. (Table of Contents Only.).

Wang, A. et al. (1991). "Polarized Regulation of Fibronectin Secretion and Alternative Splicing by Transforming Growth Factor," *J. Biol. Chem.* 266(24):15598-15601.

Weidner, N. et al. (1991). "Tumor Angiogenesis and Metastasis—Correlation in Invasive Breast Carcinoma," *N. Engl J. Med.* 324(1):1-8.

Wennström, S. et al. (1991). "cDNA Cloning and Expression of a Human FGF Receptor which Binds Acidic and Basic FGF," *Growth Factors* 4:197-208.

Wilson, I. A. et al. (1984). "The Structure of an Antigenic Determinant in a Protein," *Cell* 37:767-778.

Woffendin, C. (1994). "Nonviral and Viral Delivery of a Human Immunodeficiency Virus Protective Gene Into Primary Human T Cells," *Proc. Natl. Acad. Sci. USA* 91:11581-11585.

Wright, P. et al. (1999). "Adenovirus-Mediated TNFα Gene Transfer Induces Significant Tumor Regression in Mice," *Cancer Biother. Radiopharm.* 14(1):49-57.

Wu, C.H. et al. (1989). "Targeting Genes: Delivery and Persistent Expression of a Foreign Gene Driven By Mammalian Regulatory Elements in Vivo," *J. Biol. Chem.* 264(29):16985-16987.

Wu, G.Y. and Wu, C.H. (1987). "Receptor-Mediated in Vitro Gene Transformation by a Soluble DNA Carrier System," *J. Biol. Chem.* 262(10):4429-4432.

Wu, G.Y. and Wu, C.H. (1988). "Receptor-Mediated Gene Delivery and Expression in Vivo," *J. Biol. Chem.* 263(29):14621-14624.

Wu, G.Y. et al. (1991). "Receptor-Mediated Gene Delivery in Vivo," *J. Biol. Chem.* 266(22):14338-14342.

Wu, G.Y. et al. (1994). "Incorporation of Adenovirus into a Ligand-Based DNA Carrier System Results in Retention of Original Receptor Specificity and Enhances Targeted Gene Expression," *J. Biol. Chem.* 269(15):11542-11546.

Xu, Y. and Wang, Y. (2001). "Change in Vascular Endothelial Growth Factor Level In Serum and Urine of Esophageal Carcinoma Patients," *Chinese Journal of Oncology* 23(3):393-394. English Abstract.

Yu, J. et al. (2000). "A Dual Role of VEGI, An Endothelial Specific Gene and Novel Member of the TNF Family, in Endothelial Cell Cycle Control: Mediation of Growth Arrest of G0 Cells But Apoptosis of Proliferating Cells," *Proceedings of the 91st Annual Meeting of the American Association for Cancer Research*: San Francisco, CA vol. 41, p. 647. Abstract No. 4108.

Yu, J. et al. (2001). "Modulation of Endothelial Cell Growth Arrest and Apoptosis by Vascular Endothelial Growth Inhibitor," *Circ. Res.* 89:1161-1167.

Yu, J. et al. (2001). "The Structure of the VEGI Gene and Novel Isoforms of VEGI, a Negative Regulator of Angiogenesis," *Proceedings of the 92nd Annual Meeting of the American Association For Cancer Research*: New Orleans, LA vol. 42, p. 2. Abstract No. 7.

Yu, J.Y. et al. (1999). "VEGI, a Novel Cytokine of the TNF Superfamily, Arrests Endothelial Cell Growth at G0/G1 Phase," *Proceedings of the 90th Annual Meeting of the Amerian Association for Cancer Reserch*: Philadelphia, PA vol. 40, p. 229. Abstract No. 1522.

Yue, T-L. et al. (1999). "TL1, a Novel Tumor Necrosis Factor-Like Cytokine, Induces Apoptosis in Endothelial Cells," *J. Biol. Chem.* 274(3):1479-1486.

Zenke, M. et al. (1990). "Receptor-Mediated Endocytosis of Transferrin-Polycation Conjugates: An Efficient Way to Introduce DNA Into Hematopoietic Cells," *Proc. Natl. Acad. Sci. USA* 87:3655-3659.

Zhai, Y. et al. (1999). "Inhibition of Angiogenesis and Breast Cancer Xenograft Tumor Growth by VEGI, a Novel Cytokine of the TNF Superfamily," *International Journal of Cancer* 82:131-136.

Zhai, Y. et al. (1999). "VEGI, A Novel Cytokine of the Tumor Necrosis Factor Family, Is an Angiogenesis Inhibitor That Suppresses the Growth of Colon Carcinomas in vivo," *FASEB J.* 13:181-189.

International Search Report mailed on Aug. 18, 2004, for PCT Application No. PCT/US02/37426, filed on Nov. 12, 2002, four pages.

* cited by examiner

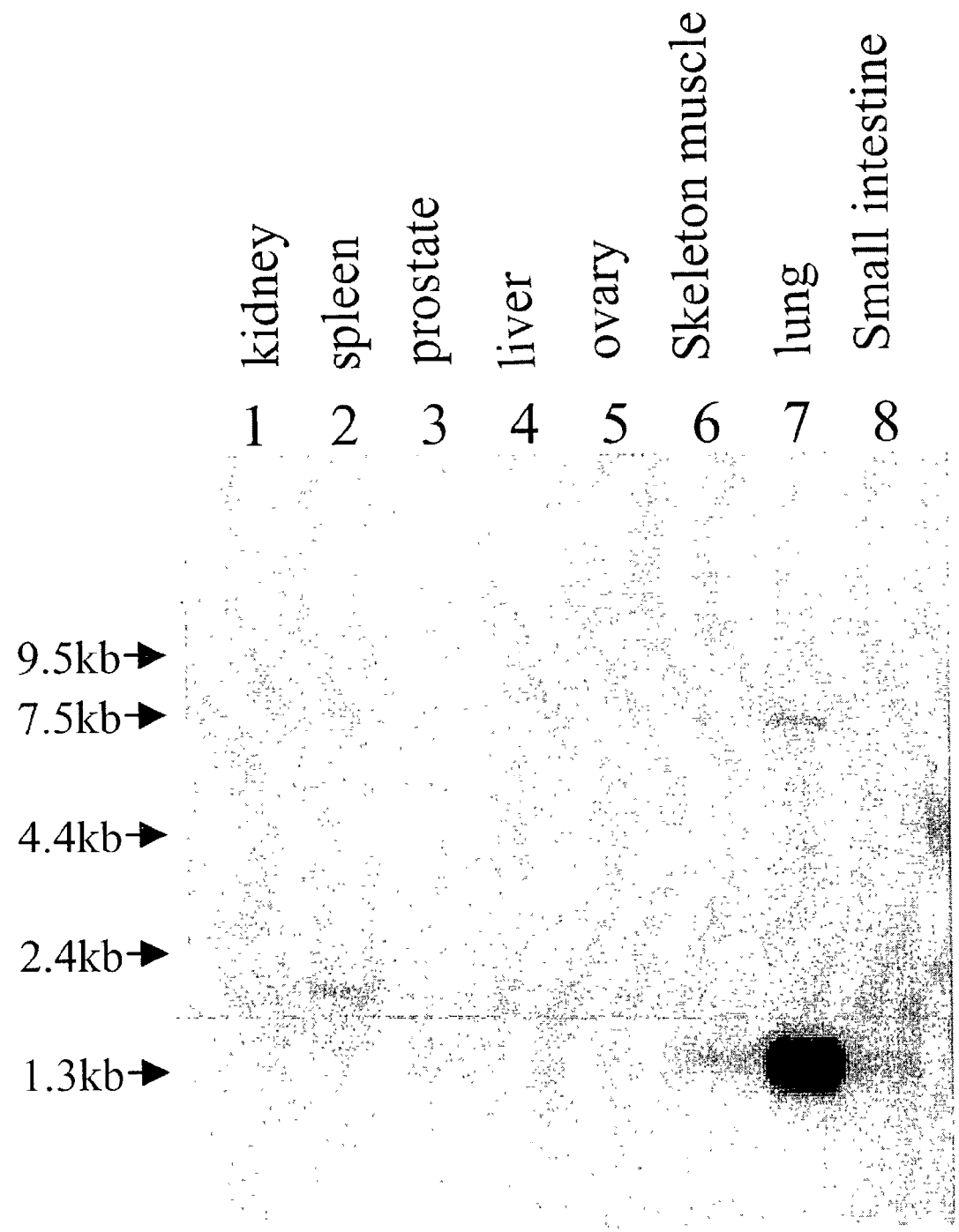
Figure 11. Probe VEGI Full Length

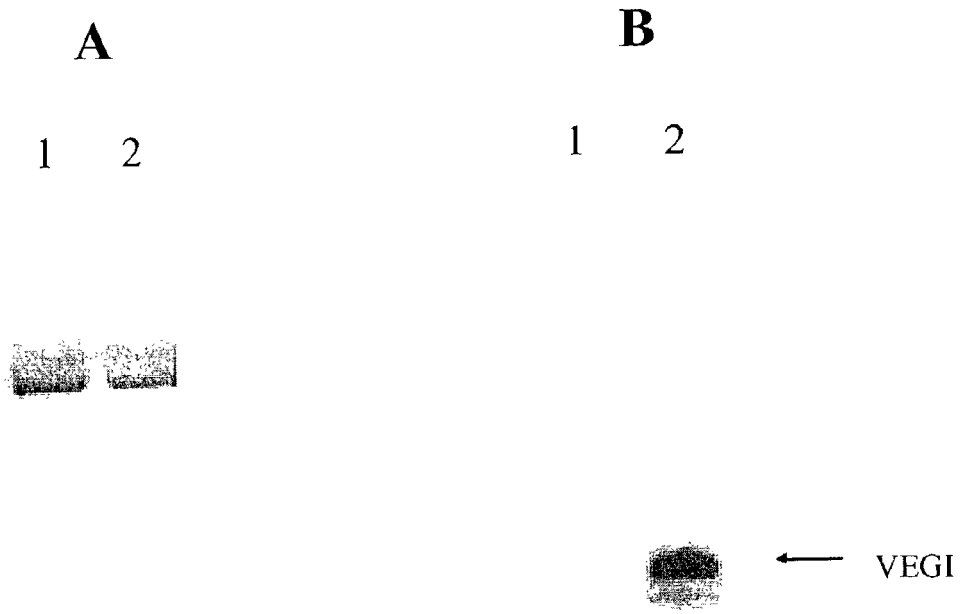

Detection of secreted VEGI in the conditioned media of VEGI-251 transfected cells
Full length VEGI-251 was cloned into pcDNA3 and transfected into MB231 cells. An VEGI affinity column was prepared by immobilising an anti-VEGI polycolonal Ab onto a CNBr activated Sepherose-4B column Secreted VEGI was purified from the conditioned media of transfected MB231 cells with this column.
The purified protein was analysed on SDS-PAGE (A) comasie blue staining of the total protein; (B) Western blotting with monoclonal antibody 13-2D to VEGI.
Lane 1: purified protein from conditioned media of vector only transfected cells.
Lane 2: purified protein from conditioned media of VEGI-251 transfected cells.

Figure 14

- VGEI-1 is VEGI-174

- VEGI-2 is VEGI-251

- IL6/VEGI is a fusion gene of VEGI-174 (residue 23-174) and the secretion signal peptide of interleukin-6.

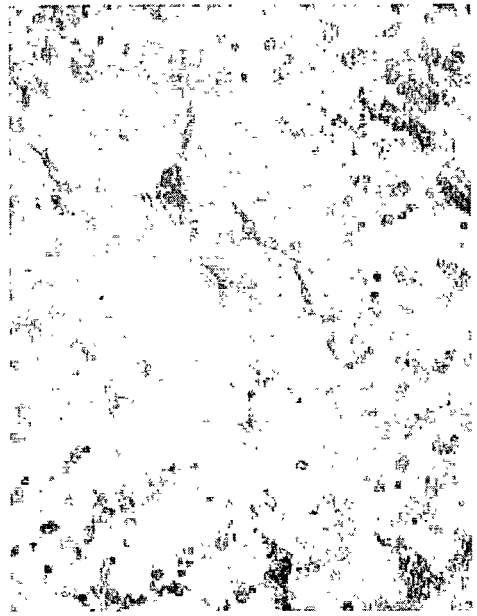
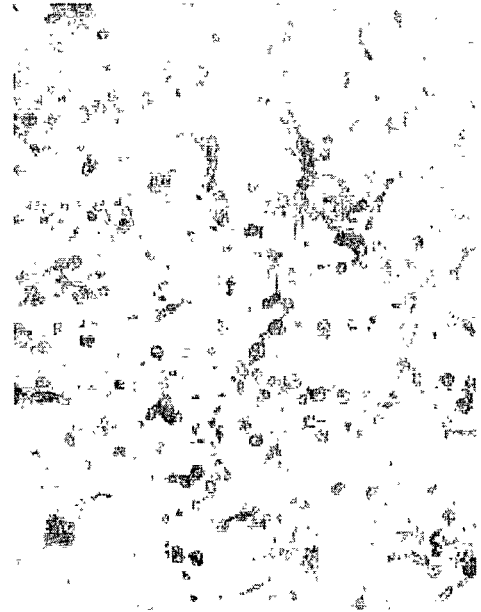
Figure 16

VASCULAR ENDOTHELIAL CELL GROWTH INHIBITOR, VEGI-192A

CROSS-REFERENCES TO RELATED APPLICATIONS

This application claims the priority benefit of U.S. provisional patent application Ser. No. 60/331,190, filed Nov. 9, 2001. The priority application is hereby incorporated herein by reference in its entirety.

GOVERNMENT SUPPORT

This invention was made with U.S. Government support under Department of Defense grant DAMD17-98-1-8093; National Institutes of Health grant NHLBI RO1 HL60660; and National Cancer Institute grant CA58185-08. The Government has certain rights in the invention.

FIELD OF THE INVENTION

The present invention relates to compositions that are useful in the treatment of conditions in which it is advantageous that angiogenesis is inhibited, for example, in the treatment of solid tumors, diabetic retinopathy, Kaposi's sarcoma, psoriasis, and rheumatoid arthritis. In particular, the invention relates to novel isoforms of vascular endothelial growth inhibitors (VEGIs), their DNA and associated protein sequences, compositions and variants thereof, and their use in the treatment of angiogenesis-driven diseases.

BACKGROUND OF THE INVENTION

Under normal physiological conditions, humans and animals undergo angiogenesis, the generation of new blood vessels into a tissue or organ, in very specific restricted situations. For example, angiogenesis is normally observed in wound healing, embryonal development, and formation of the corpus luteum, endometrium and placenta. The term "endothelium" means a thin layer of flat epithelial cells that lines serous cavities, lymph vessels and blood vessels. The term "anti-angiogenic" or "angiogenic inhibiting activity" means the capability of a molecule to inhibit angiogenesis in general.

Both controlled and uncontrolled angiogenesis are thought to proceed in a similar manner. Endothelial cells are actively involved in inflammation, cell adhesion, coagulation, thrombosis, fibrinolysis, and angiogenesis. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

During tumor growth, endothelial cells proliferate, invade the stroma, migrate toward the source of angiogenic stimuli such as cancer cells, interact with perivascular cells and stromal cells, and eventually form capillary vessels linking the tumor tissue to the circulation (J. Folkman (1995) *Nat. Med* 1:27-31). Although the undoubtedly highly complex mechanism that regulates angiogenesis is yet to be understood, it is becoming clear that the initiation or termination of the process is a result of a balance between positive and negative regulators of angiogenesis. A number of angiogenic factors, often markedly upregulated in tumor tissues, have been described, including several members of the fibroblast growth factor family, such as FGF-I (G. Gimenez-Gallego et al. (1985) *Science* 230.:1385), FGF-2 (L. Schweigerer et al. (1987) *Nature* 325: 257), and those of the vascular endothelial cell growth factor family (VEGF) (D. W. Leung et al. (1989) *Science* 246: 1306), as well as the receptors of these growth factors (L. W. Burrus and B. B. Olwin (1989) *J Biol. Chem.* 264:18647; S. Wemistrom et al. (1991) *Growth Factors* 4:197; B. Tennan et al (1992) *Biochem. Biophys. Res. Comm.* 187: 1579. C. de Vries et al., (1992) *Science* 255: 989). Recently, two new protein factors, proliferin and a proliferin-related protein, were found to participate in the regulation of the initiation and cessation of neovascularization in mouse placenta (Jackson D, et al. *Science* 266, 1581-4, 1994). All documents cited herein supra and infra are hereby expressly incorporated in their entirety by reference thereto.

Several inhibitors of angiogenesis have also been reported, including thrombospondin (D. J Good et al. (1990) *Proc. Natl. Acad. Sci. U.S.A.* 87:6624), angiostatin (M. S. O'Reilly et al. (1994) Cell 79:315), endostatin (M. S. O'Reilly et al. (1997) *Cell* 88: 277) and platelet factor-4 (E. Maione et al. (1997) *Science* 247:77). It is apparent that normal angiogenesis is promptly activated when required, and swiftly terminated when no longer needed, whereas pathological angiogenesis, once initiated is often prolonged and difficult to stop. This indicates that the negative regulation mechanism functioning in a normal angiogenesis process is missing or suppressed in a pathological angiogenesis process. It has been suggested that proteolytic activities that release angiogenesis inhibitors from a number of precursors may account partly for down-regulation of angiogenesis, as indicated by the proteolytic activation of angiostatin from plasminogen and that of endostatin from collagen XVIII (M. S. O'Reilly, (1997) Cell 88:277). Many of the known angiogenesis regulators are pleiotrophic and can act on other cell types as well as the one that produces the regulators, although it is conceivable that endothelial cells may produce autocrine factors to suppress an angiogenic process or maintain the quiescence of a mature vasculature. It is therefore an object of the present application to describe novel autocrine negative regulators of angiogenesis of a class called Vascular Endothelial Cell Growth Inhibitors (VEGI) that are specifically expressed by endothelial cells.

Published PCT Application WO 99/23105 discloses a VEGI protein (VEGI-$_{174}$) and a splice variant VEGI-$_{251}$ and their corresponding nucleotide sequences, the disclosure of which is hereby expressly incorporated into the present application by reference in its entirety. Anti-angiogenic activity of N-terminal truncated forms of VEGI-$_{174}$ was described. The protein VEGI-$_{174}$ exhibited 20-30% sequence homology to human TNFα, TNFβ, and the Fas ligand. A protein with a molecular weight of 22 kD was produced in an in vitro transcription and translation experiment using a cDNA clone as a template, consistent with the predicted open reading frame of 174 amino acids. This protein is herein referred to as VEGI-$_{174}$. Hydrophobicity analysis of the protein predicted a 12-amino acid hydrophobic region immediately following the N-terminal segment of 14 non-hydrophobic amino acids. This was consistent with the structure of a type II transmembrane protein, similar to TNFs (B. B. Aggarwal and K. Natarajan (1996) *Eur. Cytokine News*. 7:93). An isoform of VEGI was also described. This protein is herein referred to as VEGI-$_{251}$ which was predicted to be a membrane protein.

Recent Northern analysis of total RNA preparations from 22 different types of cultured cells of various lineages indicated that transcripts for this protein can only be detected in two lines of endothelial cells: HUVE cells and human venous endothelial cells of an early passage. A mRNA was not detected in human venous endothelial cells of a later passage, nor was it seen in human artery cells. In sharp contrast, the TNF family members are mostly expressed in immune cells (B. B. Aggarwal and K. Natarajan (1996), supra). For instance, TNFα is produced by macrophages, monocytes, neutrophils, and T cells, while TNFβ is predominantly produced by mitogen-stimulated T lymphocytes and leukocytes. Similarly, the ligands for Fas and other TNF family members, CD27, CD30, CD40, OX40, and 4-1 BB, are all expressed in cell types in the immune system. Using multiple tissue Northern blots, an EGI transcript was found to be expressed in placenta, lung, kidney, skeletal muscle, brain, liver, thymus, testis, ovary and peripheral blood lymphocytes.

Inhibition of angiogenesis in a tumor is an important approach for the treatment of cancer such as breast and other solid tumors. First of all, tumor growth and metastasis are dependent on angiogenesis. It has been shown in a model system that blocking the capillaries of the tumor neovasculature by specifically induced coagulation gives rise to the eradication of the tumor vasculature and leads to abrogation of the tumors. In addition, it has been suggested that endothelial cells are highly proliferative in tumor tissues but are mostly quiescent in normal tissues. This makes the tumor neovasculature a specific and attractive target. Furthermore, while the characteristics of cancer cells may vary greatly in different tumors, the endothelial cell population in most solid tumors is likely to be untransformed, and thus remains homogeneous. This would apply for both human and animal subjects. It may therefore be possible to develop an antiangiogenic therapeutic agent that could be applied universally for the treatment of many different cancers.

In addition to solid tumors, other important angiogenesis-driven diseases include diabetic retinopathy, Kaposi's sarcoma, psoriasis, rheumatoid arthritis. Patients who suffer from these diseases may benefit from an anti-angiogenic therapeutic approach.

The present invention identifies and describes sequences, functions, compositions, and therapeutic uses of novel isoforms of members of the VEGI family of proteins. Two new isoforms that are termed VEGI-$_{192a}$, and VEGI-$_{192b}$ respectively, comprise a novel N-terminal sequence that substantially alters the properties of the protein with respect to its expression, secretion, and anti-angiogenic properties.

There are disclosed two new VEGI isoforms named VEGI$_{192a}$ and VEGI$_{192b}$, both consisting of 192 amino acid residues. Both isoforms show endothelial cell-specific expression and share a C-terminal 151-residues segment with the previously described VEGI-$_{174}$ and VEGI-$_{251}$. The isoforms are generated from a 17 kb human gene by alternative splicing. VEGI$_{251}$, the most abundant isoform, contains a putative secretion signal. VEGI protein is detected in conditioned media of endothelial cells, human sera and VEGI$_{251}$-transfected mammalian cells. Subcellular localization pattern of VEGI$_{251}$ is suggestive of a secretory protein. Overexpression of VEGI$_{251}$ in endothelial cells causes dose-dependent cell death. VEGI$_{251}$-transfected cancer cells gave rise to xenograft tumors of reduced growth rate and microvessel density compared with tumors of VEGI$_{174}$ transfectants. The invention provides a view that endothelial cell-secreted VEGI can function as an autocrine inhibitor of angiogenesis and a naturally existing modulator of vascular homeostasis.

All publications cited herein are hereby incorporated by reference in their entirety.

SUMMARY OF THE INVENTION

The present invention relates to inhibitors of endothelial cell proliferation in general and inhibitors of angiogenesis in particular, and their methods of use. The complete nucleotide sequences of VEGI-$_{192a}$, VEGI-$_{192b}$, and VEGI-$_{251}$ are shown in Table 1 (SEQ ID NO: 1), Table 2 (SEQ ID NO:2), and Table 3 (SEQ ID NO:3), and the deduced amino acid sequences are shown in Table 4 (SEQ ID NO:4), Table (SEQ ID NO:5), and Table 6 (SEQ ID NO:6), respectively.

Accordingly, in one embodiment, the invention provides an isolated polynucleotide that comprises the sequence shown in Table 1 (SEQ ID NO:1), or their complement. The invention also provides an isolated polynucleotide that comprises at least 10, at least 15, at least 18, at least 20, at least 25, at least 30, at least 50, and at least 100 or more contiguous nucleotides of SEQ ID NO:1, wherein the contiguous nucleotides are within nucleotides 1-93 of SEQ ID NO:1. The invention also provides an isolated polynucleotide that comprises at least 10, at least 15, at least 18, at least 20, at least 25, at least 30, at least 50, and at least 100 or more contiguous nucleotides of SEQ ID NO:1, wherein the contiguous nucleotides comprise nucleotides 93 and 94 of SEQ ID NO:1.

In other embodiments, the invention provides an isolated polynucleotide that comprises the sequence shown in Table 2 (SEQ ID NO:2), or their complement. The invention also provides an isolated polynucleotide that comprises at least 10, at least 15, at least 18, at least 20, at least 25, at least 30, at least 50, and at least 100 or more contiguous nucleotides of SEQ ID NO:2, wherein the contiguous nucleotides are within nucleotides 1-386 of SEQ ID NO:2. The invention also provides an isolated polynucleotide that comprises at least 10, at least 15, at least 18, at least 20, at least 25, at least 30, at least 50, and at least 100 or more contiguous nucleotides of SEQ ID NO:2, wherein the contiguous nucleotides comprise nucleotides 386 and 387 of SEQ ID NO:2.

In some embodiments, the invention provides an isolated polynucleotide that comprises a sequence encoding the polypeptide of SEQ ID NO:4. The present invention also provides an isolated polynucleotide that comprises a polynucleotide encoding at least 5, at least 10, at least 15, at least 20, at least 25, or more contiguous amino acids of SEQ ID NO:4, wherein the contiguous amino acids are within amino acids 1-26 of SEQ ID NO:4. The invention also provides an isolated polynucleotide that comprises a polynucleotide encoding at least 5, at least 10, at least 15, at least 20, at least 25, or more contiguous amino acids of SEQ ID NO:4, wherein the contiguous amino acids comprise amino acids 26 and 27 of SEQ ID NO:4. In some embodiments, the contiguous amino acids are amino acids about 5-192, 10-192, 15-192, 20-192, or 25-192 of the sequence shown in Table 4 (SEQ ID NO:4).

In some embodiments, the invention provides an isolated polynucleotide that comprises a sequence encoding the polypeptide of SEQ ID NO:5. The present invention also provides an isolated polynucleotide that comprises a polynucleotide encoding at least 5, at least 10, at least 15, at least 20, at least 25, or more contiguous amino acids of SEQ ID NO:5, wherein the contiguous amino acids are within amino acids 1-26 of SEQ ID NO:5. The invention also provides an isolated polynucleotide that comprises a polynucleotide encoding at least 5, at least 10, at least 15, at least 20, at least 25, or more contiguous amino acids of SEQ ID NO:5, wherein the contiguous amino acids comprise amino acids 26 and 27 of SEQ ID NO:5. In some embodiments, the contiguous amino acids are amino acids about 5-192, 10-192, 15-192, 20-192, or 25-192 of the sequence shown in Table 5 (SEQ ID NO:5).

In some embodiments, the polynucleotide of the invention provides sequence encoding functionally-preserved variants of the nucleic acid sequences disclosed herein, which include nucleic acid substitutions, additions, and/or deletions. Variants include naturally occurring variants of the polynucleotide sequence (e.g. degenerate variants, allelic variants, etc.)

In some embodiments, the invention provides an isolated polynucleotide having at least 85%, at least 88%, at least 90%, at least 92%, at least 94%, at least 96%, at least 98%, or at least 99% sequence identity with the polynucleotides of the invention as described herein. One embodiment provides an isolated polynucleotide having at least 85%, at least 88%, at least 90%, at least 92%, at least 94%, at least 96%, at least 98%, or at least 99% sequence identity with the sequence of nucleotides 1-93 shown in Table 1 (SEQ ID NO:1) or nucleotides 1-386 shown in Table 2 (SEQ ID NO:2).

In some embodiments, the polynucleotides of the invention further comprise a detectable label. In some embodiments, the polynucleotide of the invention is immobilized on a surface. In some embodiments of the invention, the polynucleotide of the invention is single stranded. In some embodiments of the invention, the polynucleotide of the invention is selected from the group consisting of DNA and RNA. In some embodiments of the invention, the polynucleotide of the invention is prepared in part by chemical synthesis.

It is understood that (unless otherwise specified or required), any embodiment of the invention described herein that is a polynucleotide encompasses both the double-stranded form and each of two complementary single-stranded forms known or predicted to make up the double stranded form.

It is further understood that the invention provides embodiments "consisting of" or "consisting essentially of" the polynucleotide, polypeptides, and/or antibodies described herein.

In another aspect, the invention provides vectors and expression vectors comprising any of the polynucleotides described herein.

In still other aspects, the invention provides a host cell comprising any of the polynucleotide or vectors described herein. In some embodiments, the host cell is prokaryotic, such as $E.\ coli$. In some embodiments, the host cell is eukaryotic, such as Chinese hamster ovary (CHO) cells.

The present invention also encompasses cells containing recombinant polynucleotides which comprises a VEGI-$_{192a}$ or VEGI-$_{192b}$ polynucleotide or variants of VEGI-$_{192a}$ or VEGI-$_{192b}$ polynucleotide. In one embodiment, the invention provides a genetically engineered mammalian cell or bacterial cell, such as $E.\ coli$, comprising a recombinantly modified VEGI-$_{192a}$ or VEGI-$_{192b}$ polynucleotide, such that the polynucleotide is overexpressed. In another embodiment, the invention provides cells comprising a variant of VEGI-$_{192a}$ or VEGI-$_{192b}$ polynucleotide. In another embodiment, a VEGI-$_{192a}$ or VEGI-$_{192b}$ polynucleotide is operatively linked to an inducible promoter. In still other embodiments, the genetically engineered cells possess a variant VEGI-$_{192a}$ or VEGI-$_{192b}$ gene instead of a native VEGI-$_{192a}$ or VEGI-$_{192b}$ gene.

The invention also provides VEGI-$_{192a}$ polypeptides. Therefore, the invention provides an isolated polypeptide comprising the sequence of SEQ ID NO:4. The invention also provides an isolated polypeptide comprising a polypeptide encoded by any of the polynucleotides of the invention, as described herein. In other embodiments, the present invention also provides an isolated polypeptide that comprises at least about 5, at least 10, at least 15, at least 20, at least 25, or more contiguous amino acids of a sequence depicted in Table 4 (SEQ ID NO:4), wherein the contiguous amino acids are within amino acids 1-26 of the sequence shown in Table 4 (SEQ ID NO:4). In other embodiments, the present invention also provides an isolated polypeptide that comprises at least about 5, at least 10, at least 15, at least 20, at least 25, or more contiguous amino acids of a sequence depicted in Table 4 (SEQ ID NO:4), wherein the contiguous amino acids comprise amino acids 26 and 27 of SEQ ID NO:4. In some embodiments, the contiguous amino acids are amino acids about 5-192, 10-192, 15-192, 20-192, 25-192 of SEQ ID NO:4.

The invention also provides VEGI-$_{192b}$ polypeptides. Therefore, the invention provides an isolated polypeptide comprising the sequence of SEQ ID NO:5. The invention also provides an isolated polypeptide comprising a polypeptide encoded by any of the polynucleotides of the invention, as described herein. In other embodiments, the present invention also provides an isolated polypeptide that comprises at least about 5, at least 10, at least 15, at least 20, at least 25, or more contiguous amino acids of a sequence depicted in Table 5 (SEQ ID NO:5), wherein the contiguous amino acids are within amino acids 1-26 of the sequence shown in Table 5 (SEQ ID NO:5). In other embodiments, the present invention also provides an isolated polypeptide that comprises at least about 5, at least 10, at least 15, at least 20, at least 25, or more contiguous amino acids of a sequence depicted in Table 5 (SEQ ID NO:5), wherein the contiguous amino acids comprise amino acids 26 and 27 of SEQ ID NO:5. In some embodiments, the contiguous amino acids are amino acids about 5-192, 10-192, 15-192, 20-192, 25-192 of SEQ ID NO:5.

In other embodiments, the invention provides any polypeptide described herein, wherein the polypeptide includes an epitope. In other embodiments, the invention provides any polypeptide described herein, wherein the polypeptide is immobilized on a solid support.

In other embodiments, the invention provides polypeptides that retains a biological activity of VEGI-$_{192a}$ and/or VEGI-$_{192b}$ and/or VEGI-$_{251}$. As shown in the Examples, VEGI-$_{192a}$ inhibits vascular endothelial cell growth; and VEGI-$_{251}$ upon expression inhibits vascular endothelial cell growth, the formation of capillary-like tubes in an in vitro angiogenesis model, and also inhibits the growth of xenograft tumors in athymic nude mice.

The invention also provides antibodies that selectively bind VEGI-$_{192a}$ and/or VEGI-$_{192b}$. Accordingly, the invention provides an antibody that selectively binds to any of the VEGI-$_{192a}$ and/or VEGI-$_{192b}$ polypeptides described herein. In one embodiment, the antibody is capable of binding selectively to VEGI-$_{192a}$ or VEGI-$_{192b}$. In other embodiment, the antibody is capable of binding selectively to both VEGI-$_{192a}$ and VEGI-$_{192b}$, but not to other isoforms of VEGI. In some embodiments, the antibody binds to a polypeptide encoded by any of the polynucleotides described herein. In one embodiment, the invention provides an antibody capable of binding to a polypeptide of this invention. In another embodiment, the antibody is capable of specifically binding to a polypeptide comprising (a) the sequence shown in Table 4 (SEQ ID NO:4)

and/or Table 5 (SEQ ID NO:5); or (b) at least 10 contiguous amino acids of SEQ ID NO:4 and/or SEQ ID NO:5, wherein the contiguous amino acids are within amino acids 1-26 shown in Table 4 (SEQ ID NO:4) and/or Table 5 (SEQ ID NO:5). The present invention also provides an antibody that is capable of binding to a region of the polypeptide shown in Table 4 (SEQ ID NO:4) and/or Table 5 (SEQ ID NO:5), wherein said region is at least about 5, at least 10, at least 15, at least 20, at least 25, or more contiguous amino acids of SEQ ID NO:4 and/or SEQ ID NO:5, and said region comprise amino acids 26 and 27 of SEQ ID NO:4 and/or SEQ ID NO:5.

In some embodiments, the antibody is a polyclonal antibody. In other embodiments, the antibody is a monoclonal antibody. In still other embodiments, the antibody is immobilized on a solid support. In still other embodiments, the antibody further comprises a detectable label.

The present invention also provides compositions, including pharmaceutical compositions, comprising the polynucleotides, polypeptides, antibodies, recombinant vectors, and host cells of the invention. In some embodiments, the invention provides a pharmaceutical composition comprising the polypeptide of SEQ ID NO:4, or a fragment thereof, wherein the fragment comprises amino acids 26 and 27, in a pharmaceutically acceptable excipient.

The present invention also provides an angiogenesis inhibitor, where the inhibitor comprises VEGI-$_{192a}$, VEGI-$_{192b}$, or VEGI-$_{251}$ polynucleotides, polypeptides or derivatives in a pharmaceutically acceptable carrier, in a pharmaceutically acceptable amount.

In another embodiment, the present invention provides a repressor or inhibitor of cancer growth composition comprising substantially purified VEGI isoform (i.e., VEGI-$_{192a}$, VEGI-$_{192b}$, or VEGI-$_{251}$) polynucleotides or polypeptides of the invention.

In another embodiment, the present invention provides an accelerator of angiogenesis. the accelerator comprising an antibody, an antisense oligonucleotide, an antagonist, a ribozyme, drug or agent which reduces or eliminates VEGI-$_{192a}$, VEGI-$_{192b}$, or VEGI-$_{251}$ function when supplied in a pharmaceutically acceptable carrier, in a pharmaceutically acceptable amount.

The invention also provides kits, arrays comprising any of the polynucleotides, polypeptides and antibodies described herein. In one embodiment, the invention provides kits or arrays for assessing amount of polynucleotide in a sample comprising any of the polynucleotides described herein. In other embodiment, the invention provides kits or arrays for assessing level of polypeptide in a sample comprising any of the antibodies described herein.

In another embodiment, the present invention provides a method for inhibiting angiogenesis which comprises administering to an individual (such as a human or animal) a composition comprising a substantially purified VEGI-$_{192a}$, VEGI-$_{192b}$, or VEGI-$_{251}$ polynucleotide, polypeptides of the invention, or a modified form of these disclosed VEGI isoforms described herein in a dosage sufficient to inhibit angiogenesis. In one embodiment, the composition comprises a gene delivery vector comprising the polynucleotide shown in Table 3 (SEQ ID NO:3) or a polynucleotide encoding the polypeptide of SEQ ID NO:6. In some embodiments, the polynucleotide is operably associated with a regulatory sequence that controls gene expression. In other embodiment, the composition comprising substantially purified VEGI-$_{192a}$ polypeptide of the sequence shown in Table 4 (SEQ ID NO:4), or a functional fragment, wherein the fragment comprises amino acids 26 and 27 of SEQ ID NO:4 or comprises at least one amino acids from amino acids 1-26 of SEQ ID NO:4.

In another embodiment, the invention provides a method for the treatment or amelioration of disease and processes that are mediated by uncontrolled angiogenesis, comprising the step of administering to an individual a composition comprising a VEGI-$_{192a}$, VEGI-$_{192b}$, or VEGI-$_{251}$ polynucleotide, polypeptides, or a modified form of these disclosed VEGI isoforms described herein in a dosage sufficient to control angiogenesis. In one embodiment, the composition comprises a gene delivery vector comprising the polynucleotide shown in Table 3 (SEQ ID NO:3) or a polynucleotide encoding the polypeptide of SEQ ID NO:6. In some embodiments, the polynucleotide is operably associated with a regulatory sequence that controls gene expression. In other embodiment, the composition comprising substantially purified VEGI-$_{192a}$ polypeptide of the sequence shown in Table 4 (SEQ ID NO:4), or a functional fragment, wherein the fragment comprises amino acids 26 and 27 of SEQ ID NO:4 or comprises at least one amino acids from amino acids 1-26 of SEQ ID NO:4.

In another embodiment, the present invention provides a method for treating cancer or suppressing tumor growth which comprises administering to an individual a composition comprising a VEGI-$_{192a}$, VEGI-$_{192b}$, or VEGI-$_{251}$ polynucleotide, polypeptides, or a modified form of these disclosed VEGI isoforms described herein in a dosage sufficient to suppress tumor growth. In one embodiment, the composition comprises a gene delivery vector comprising the polynucleotide shown in Table 3 (SEQ ID NO:3) or a polynucleotide encoding the polypeptide of SEQ ID NO:6. In some embodiments, the polynucleotide is operably associated with a regulatory sequence that controls gene expression. In other embodiment, the composition comprising substantially purified VEGI-$_{192a}$ polypeptide of the sequence shown in Table 4 (SEQ ID NO:4), or a functional fragment, wherein the fragment comprises amino acids 26 and 27 of SEQ ID NO:4 or comprises at least one amino acids from amino acids 1-26 of SEQ ID NO:4.

In another embodiment, the present invention provides a method for accelerating angiogenesis which comprises administering to a human or animal a composition comprising an antibody, an antisense oligonucleotide, an antagonist, a ribozyme, a drug, or agent which reduces or eliminates activity of VEGI-$_{192a}$, VEGI-$_{192b}$, and/or VEGI-$_{251}$.

In yet another embodiment, the present invention provides a therapeutic method and composition for the treatment or amelioration of diseases and processes that are mediated by angiogenesis, including, but not limited to, hemangioma, solid tumors, leukemia, metastasis, telangiectasia, psoriasis sclerodemia, pyogenic granuloma, myocardial anaiogenesis, plagie neovascularization, coronary collaterals, ischemic limb anciogenesis, corneal diseases, rubeosis, neovascular glaucoma. diabetic retinopathy, retrolental fibroplasia, arthritis, diabetic neovascularization, uveitis, retinopathy of prematurity, macular degeneration, corneal graft neovascularization, graft versus host disease, inflammatory bowel disease, myelosuppression, and restenosis; wherein angiogenesis is uncontrolled or excessive and requires inhibition, the method comprising providing to an individual in need of such treatment an effective amount of VEGI isoform (i.e., VEGI-$_{192a}$, VEGI-$_{192b}$, or VEGI-$_{251}$) polynucleotides or polypeptides of the invention such that angiogenesis is inhibited.

In yet another embodiment, the present invention provides a therapeutic method and composition for the treatment or amelioration of diseases such as macular degeneration, wound healing, peptic ulcer, fractures, keloids, vasculogenesis, hematopoiesis, ovulation, menstruation, and placentation, in which angiogenesis is desired, the method comprising administering to an individual in need of such treatment, an antagonist of VEGI isoform (i.e., VEGI-$192a$, VEGI-$192b$, or VEGI-$251$) polynucleotides or polypeptides of the present invention; antisense oligonucleotides specific for VEGI isoform polynucleotides, or anti-VEGI antibodies, agents, or drugs which reduce or eliminate VEGI function in a pharmaceutically acceptable carrier, in a pharmaceutically acceptable amount.

In another embodiment, the present invention provides a method for detecting VEGI isoform polypeptide (VEGI-$192a$, or VEGI-$192b$) comprising contacting a sample from an individual with an antibody described herein which selectively binds to the VEGI polypeptide of the invention, and detecting the presence or absence of a complex formed between a polypeptide in the sample and the antibody. These detection methods are also applicable to detecting any of the VEGI-$192a$ or VEGI-$192b$ described herein.

In another embodiment, the present invention also provides a method for detecting VEGI isoform (VEGI-$192a$, or VEGI-$192b$) polynucleotides comprising contacting a sample from an individual with a polynucleotide (such as an oligonucleotide) which selectively binds to the VEGI polynucleotide of the invention; and detecting the presence or absence of a duplex formed between the oligonucleotide and a polynucleotide in the sample. These methods are also applicable to detecting any of the VEGI-$192a$ or VEGI-$192b$ polynucleotides described herein.

In yet another embodiment, the present invention provides a method for the diagnosis of conditions involving pathological angiogenesis, where the method comprises detecting the presence or absence of polypeptides derived from VEGI-$192a$ or VEGI-$192b$, in a sample, the method comprising the steps of:

(i) contacting a sample from a subject suspected of having pathological angiogenesis with antibodies that are specific for the VEGI-$192a$ and/or VEGI-$192b$ polypeptides of the invention; and (ii) detecting the presence or absence of a complex formed between VEGI-$192a$, and/or VEGI-$192b$, and the antibodies.

In yet another embodiment, the present invention provides a method for the diagnosis of pathological angiogenesis comprising detecting the presence or absence of VEGI-$192a$ or VEGI-$192b$, polynucleotides (preferably RNA) in a sample, the method comprising the steps of:

(i) contacting a sample from a subject suspected of having pathological angiogenesis with polynucleotides (such as oligonucleotides) that specifically bind VEGI-$192a$ or VEGI-$192b$ polynucleotides of the invention (for example, RNA); and (ii) detecting the presence or absence of a duplex formed between polynucleotides and oligonucleotides derived from VEGI-$192a$, or VEGI-$192b$.

In another embodiment, the present invention provides a method for the diagnosis of pathological angiogenesis using the polymerase chain reaction (PCR), the method comprising designing primers using the nucleotide sequence of VEGI isoform (i.e. VEGI-$192a$, VEGI-$192b$) as shown in SEQ ID NO:1, and SEQ ID NO:2, wherein the polymerase chain reaction specifically amplifies a region of VEGI as the basis for detection. The primers can be used to amplify VEGI DNA or VEGI RNA, the latter amplification occurring after RNA is converted into complementary DNA (cDNA) by reverse transcription of the RNA. The PCR assay can be made quantitative by comparing the amplified product to a standard, which can be generated using methods known in the art.

In yet another embodiment, the present invention provides a method for the detection of VEGI isoform (i.e. VEGI-$192a$, or VEGI-$192b$) polynucleotides in a sample, the method comprising assaying for the presence or absence of VEGI-$192a$, or VEGI-$192b$ isoform RNA or DNA in a sample by hybridization assay.

In a further embodiment, the present invention provides a diagnostic or prognostic kit comprising antibodies that bind VEGI isoform (i.e. VEGI-$192a$, or VEGI-$192b$) polynucleotides or polypeptides of the invention; oligonucleotides that hybridize to VEGI DNA or RNA; and/or PCR primers for amplification of VEGI DNA or RNA, and ancillary reagents suitable for use in detecting the presence of VEGI isoform in a sample. Since VEGI may function as a membrane protein, a naturally existing soluble form of membrane-bound VEGI may function as its antagonist, and methods for detecting the soluble form are included in another embodiment of the present invention.

In yet another embodiment, the present invention provides a diagnostic assay comprising detecting the presence or absence of a mutation in VEGI isoform (i.e. VEGI-$192a$, or VEGI-$192b$) polynucleotides, which results in the decrease or increase of VEGI isoform expression or function. Such an assay would include hybridization assay, restriction map polymorphism assays, and gene sequencing, to name a few.

In yet another embodiment, the present invention provides a method for testing possible agents or drugs for angiogenic inhibitory activity by testing whether or not the drug or agent is capable of upregulating VEGI isoform (i.e., VEGI-$192a$, or VEGI-$192b$) expression and/or activity. Since VEGI isoforms, like other angiogenic inhibitors, are activated by proteases which release the protein from the cell membrane, proteases, as well as other agents that facilitate such activation such as metal ions would be useful as agents for increasing the expression of VEGI isoforms.

In another embodiment, the present invention provides a method for testing possible antitumor agents or drugs by testing whether or not the drug or agent is capable of inhibiting angiogenesis by upregulating VEGI isoform expression and/or activity.

In still another embodiment, the present invention provides a method for testing possible drugs or agent which promote angiogenesis by testing whether or not the agent or drug can block and/or inhibit VEGI function (for example, inhibition of angiogenesis). In this case, inhibition of proteases which activate VEGI isoforms as discussed above or agents required for, or agents which facilitate such activation such as metal ions, can be used to down-regulate VEGI, thereby enhancing angiogenesis.

BRIEF DESCRIPTION OF THE FIGURES

FIG. 11. Photograph of the results of a multi-tissue Northern blotting analysis of the expression of VEGI in various human organs, using P-32-labeled VEGI-$_{174}$ cDNA as a probe. VEGI mRNA signals of different sizes are visible.

FIG. 14. Photograph of a Western blotting analysis of the conditioned media of MDA-MB-231 cells transfected with an empty vector (lane 1) or VEGI-$_{251}$ cDNA (lane 2). The conditioned media is subjected to a gel-filtration chromatography and fractions with a molecular weight range of 10-50 kD were collected and subjected to SDS-PAGE. Panel A: Coomassie blue staining of the gel. Panel B: Western blotting with a monoclonal antibody (13-2D) to VEGI.

FIG. 16. Immunohistochemical analysis of the tumor samples obtained from the experiments described in FIG. 7, using mAb 13-2D against human VEGI. VEGI-overexpressing cells are stained brown. Panels on the left are photographs of sections of tumor formed by the $VEGI_{251}$ transfected cells. Levels of $VEGI_{251}$ production were apparently highly variable, as evident from the intensive staining of some of the tumor sections (G9-1R), which suggests high levels of VEGI production, versus markedly less staining of some tumors of the same group (G9-2R). Panels on the right are photographs of sections of tumors formed by vector-control cells. Brown-staining in the control tumor sections are likely to be the results of antibody cross-reaction to the intrinsic VEGI molecules on the mouse endothelium.

DETAILED DESCRIPTION OF THE INVENTION

Figure 1:
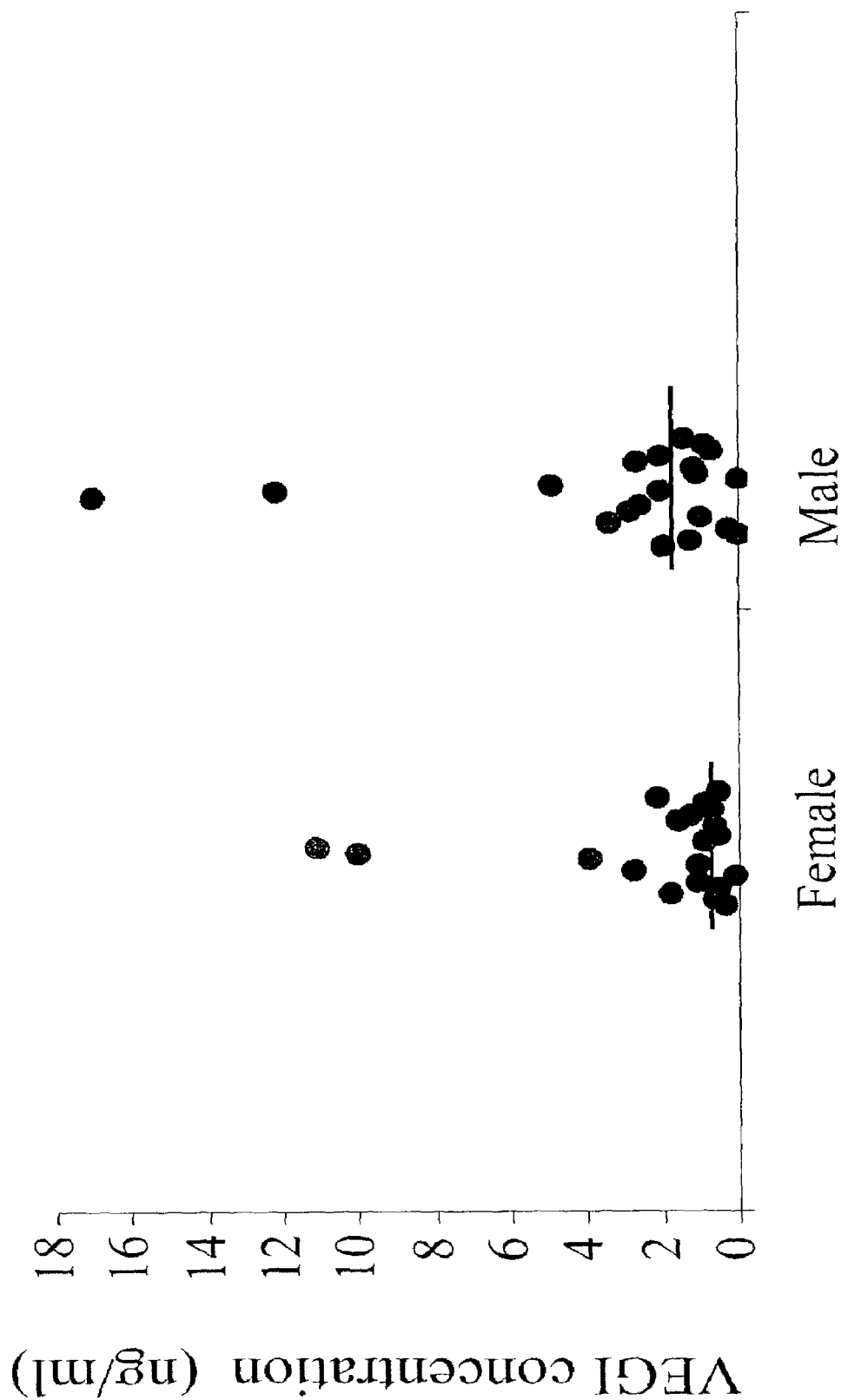
FIG. 1. Serum VEGI level in normal adults. Serum from 40 normal volunteers (20 male, 20 female) were measured by ELISA with an anti-VEGI antibody. Each point represents a single value. Purified recombinant VEGI was used to generate a standard curve. The horizontal bars among the spots indicate the median values for each gender group.

The present invention provides novel isoforms of VEGI polynucleotides and polypeptides, which inhibit vascular endothelial cell growth and methods for the treatment of diseases and processes that are mediated by or associated with angiogenesis via administering these polynucleotides, polypeptides, and other agents. The VEGI polynucleotides or polypeptides of the invention can be isolated from body fluids including, but not limited to, serum, urine, and ascites, or synthesized by chemical or biological methods (for example, cell culture, recombinant gene expression).

Recombinant techniques include gene amplification from DNA sources using the polymerase chain reaction (PCR), and gene amplification from RNA sources using reverse transcriptase/PCR. These methods are well known in the art. VEGI inhibits the growth of blood vessels into tissues such as unvascularized or vascularized tumors. The present invention includes a protein that has a molecular weight of approximately 22 kD and any modified form of the protein, including, but not limited to, a truncation or a post-translational modification such as a glycosylated form of the protein that is capable of overcoming the angiogenic activity of endogenous growth factors.

Definitions

As described herein, a "mutant" or "variant" VEGI polynucleotide or polypeptide is a polynucleotide or polypeptide sequence that comprises one or more deletions, addition, transversion, or alteration in nucleic acid or amino acid sequence. As described further herein, a mutant VEGI sequence may result in a truncated or altered VEGI polynucleotide or polypeptide, increased or decreased expression of a VEGI polynucleotide or polypeptide, or any combination thereof. The mutation may be in coding, non-coding, 5' or 3' flanking, genomic or coding nucleotides.

A "functionally preserved" variant of a VEGI isoform (i.e. VEGI-$_{192a}$, VEGI-$_{192b}$, or VEGI-$_{251}$) polynucleotide or VEGI isoform polypeptide is a VEGI sequence which retains at least one aspect of VEGI isoform function. Functionally preserved variants can be due to differences in linear sequence, arising from, for example, single base mutation(s), addition(s), deletion(s), and/or modification(s) of the bases. The difference can also arise from changes in the sugar(s) and/or linkage(s) between the bases. Regarding polypeptides, functionally preserved variants may arise, for example, by conservative and/or non-conservative amino acid substitutions, amino acid analogs, and deletions. The function that is preserved depends upon the relevant function being considered. For example, if a VEGI isoform polynucleotide is considered for a probe, then the ability of a variant polynucleotide sequence to hybridize to the target is the relevant function. If a polynucleotide is considered for its ability to encode a VEGI isoform polypeptide (or fragment thereof), then the ability of a variant sequence to encode the same polypeptide is the relevant function. If a VEGI isoform polypeptide is considered for its ability to bind to a particular entity (such as an antibody or another protein), then the ability of a variant sequence to encode a polypeptide with equivalent binding characteristics that is relevant. A VEGI isoform polypeptide may be considered for its biological activity of the encoded gene product (e.g., a biological activity ascribed to a gene product corresponded to the VEGI isoform polynucleotides as a result of the assignment of the gene product to a protein family(ies) and/or identification of a functional domain present in the gene product). By a polypeptide demonstrating "functional activity" is meant, a polypeptide capable of displaying one or more known functional activities associated with a complete or mature VEGI isoform polypeptide. Such functional activities include, but are not limited to, biological activity (for example, inhibition of angiogenesis, inhibition of vascular endothelial cell proliferation, induction of cell adhesion, antigenicity (ability, to bind or compete with one or more VEGI isoform polypeptide for binding to an anti-VEGI isoform antibody), immunogenicity (ability to generate antibody which binds to one or more VEGI isoform polypeptides), the ability to form polymers with other VEGI polypeptides. and ability to bind to a receptor or ligand for a VEGI polypeptide (for example, DR3).

As used herein, "expression" includes transcription and/or translation.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

A "reagent" polynucleotide, polypeptide, or antibody, is a substance provided for a reaction, the substance having some known and desirable parameters for the reaction. A reaction mixture may also contain a "target", such as a polynucleotide, antibody, polypeptide, or assembly of polypeptides that the reagent is capable of reacting with. For example, in some types of diagnostic tests, the presence and/or amount of the target in a sample is determined by adding a reagent, allowing the reagent and target to react, and measuring the amount of reaction product (if any). In the context of clinical management, a "target" may also be a cell, collection of cells, tissue, or organ that is the object of an administered substance, such as a pharmaceutical compound.

A "stable duplex" of polynucleotides, or a "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

A gene or polynucleotide is "differentially expressed" in a test sample when the polynucleotide is detected at a higher or lower level compared with a control sample of the same type. Typically, a differentially expressed polynucleotide includes polynucleotides that are expressed such that, for example, mRNA is found at levels at least about 25%, at least about 50% to 75%, at least about 90%, at least about 2-fold, at least about 4-fold, at least about 5-fold, and at least about 10-fold or more, higher (e.g. overexpressed) or lower (e.g., underexpressed). The comparison can be made between two tissue, for example, if one is using in situ hybridization or another assay method that allows some degree of discrimination among cell types in the tissue. The comparison may also be made between cells removed from their tissue source.

An "effective amount" of drug, compound, or pharmaceutical composition is an amount sufficient to effect beneficial or desired results including clinical results such as inhibiting vascular endothelial cell growth, inhibiting angiogenesis, promoting angiogenesis, shrinking the size of the tumor, retardation of cancerous cell growth, decreasing one or more symptoms resulting from the disease, increasing the quality of life of those suffering from the disease, decreasing the dose of other medications required to treat the disease, enhancing effect of another medication, delaying the progression of the disease, and/or prolonging survival of patients, either directly or indirectly. An effective amount can be administered in one or more administrations. As is understood in the angiogenesis-associated disease clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including and preferably clinical results. For purposes of this invention, beneficial or desired clinical results include, but are not limited to, one or more of the following: reducing the proliferation of vascular endothelial cells, inhibiting angiogenesis, promoting angiogenesis, reducing the size of the tumor, decreasing symptoms resulting from the disease, increasing the quality of life of those suffering from the disease, decreasing the dose of other medications required to treat the disease, delaying the progression of the disease, and/or prolonging survival of patients.

"Development" or "progression" of angiogenesis-associated disease herein means initial manifestations and/or ensuing progression of the disorder. Development of angiogenesis-associated disease can be detectable and assessed using standard clinical techniques. However, development also refers to disease progression that may be undetectable. For purposes of this invention, development or progression refers to the biological course of the disease state. "Development" includes occurrence, recurrence, and onset. As used herein "onset" or "occurrence" of angiogenesis-associated disease includes initial onset and/or recurrence.

As used herein, "delaying development" of angiogenesis-associated disease means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

As used herein and in the appended claims, the singular forms "a", "and", and "the" include plural referents unless the context clearly dictates otherwise. Thus, for example, reference to "a polynucleotide" includes a plurality of such polynucleotides and reference to "the agent" includes reference to one or more agents and equivalents thereof known to those skilled in the art, and so forth.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

Polynucleotides of the Invention

The present invention provides polynucleotides of VEGI isoforms, including polynucleotides encoding VEGI-$192a$, VEGI-$192b$, and VEGI-$251$. The nucleotide sequences corresponding to the novel isoforms are given in Tables 1, 2, and 3 (SEQ ID NO:1, SEQ ID NO:2, and SEQ ID NO:3), and their respective polypeptide sequences are given in Tables 4, 5, and 6 (SEQ ID NO:4, SEQ ID NO:5, and SEQ ID NO:6).

TABLE 1

Polynucleotide sequence encoding VEGI-$192a$ (SEQ ID NO:1)

```
CTCCTATCAT AGGCGCCATG CAACTCACAA AGGGCCGTCT TCATTTCAGT CACCCTTTGT
CTCATACAAA GCACATTTCT CCTTTTGTTA CAGATGCACC TCTTAGACCA GACGGAGATA
AGCCAAGGGC ACACCTGACA GTTGTGAGAC AAACTCCCAC ACAGCACTTT AAAAATCAGT
TCCCAGCTCT GCACTGGGAA CATGAACTAG GCCTGGCCTT CACCAAGAAC CGAATGAACT
ATACCAACAA ATTCCTGCTG ATCCCAGAGT CGGGAGACTA CTTCATTTAC TCCCAGGTCA
CATTCCGTGG GATGACCTCT GAGTGCAGTG AAATCAGACA AGCAGGCCGA CCAAACAAGC
CAGACTCCAT CACTGTGGTC ATCACCAAGG TAACAGACAG CTACCCTGAG CCAACCCAGC
TCCTCATGGG GACCAAGTCT GTATGCGAAG TAGGTAGCAA CTGGTTCCAG CCCATCTACC
TCGGAGCCAT GTTCTCCTTG CAAGAAGGGG ACAAGCTAAT GGTGAACGTC AGTGACATCT
CTTTGGTGGA TTACACAAAA GAAGATAAAA CCTTCTTTGG AGCCTTCTTA CTATAG
```

TABLE 2

Polynucleotide sequence encoding VEGI-$192b$ (SEQ ID NO:2)

```
TTAAACGGGC CCTCTAGACT CGAGCGGCCG CCACTGTGCT GGATATCTGC AGAATTCGGC
TTAGCGCGTG AATCAGATCG GGGGGGGGGG TTAAGCAAAG CCATAAAACT GTCAGTTTAA
TATACCATCA TTTCACTAAC ATGAAGTGTG CCGGCTCTGT CCCCCCCTTT CTTTTCCTCC
TTCCAACTCT TTTAAAAAAG AACAGCTCTA CTTACGCCAA GGTGAATTT TGGCTCTACT
AGCCACTATT CTGCGACAGA GTGGCTTTGT TGACGTGAGA AAGGCTCTCT TTGCTTTGCC
AGAATTAGTC ATGGAAACTT CACAGGAACA CCAGGGCCCC TCAGATATAC ACAGAATACC
ATGGAGCTGG GGACAAAGGA ATTCACATGC ACCTCTTAGA GCAGACGGAG ATAAGCCAAG
GGCACACCTG ACAGTTGTGA GACAAACTCC CACACAGCAC TTTAAAAATC AGTTCCCAGC
TCTGCACTGG GAACATGAAC TAGGCCTGGC CTTCACCAAG AACCGAATGA ACTATACCAA
CAAATTCCTG CTGATCCCAG AGTCGGGAGA CTACTTCATT TACTCCCAGG TCACATTCCG
TGGGATGACC TCTGAGTGCA GTGAAATCAG ACAAGCAGGC CGACCAAACA AGCCAGACTC
CATCACTGTG GTCATCACCA AGGTAACAGA CAGCTACCCT GAGCCAACCC AGCTCCTCAT
GGGGACCAAG TCTGTATGCG AAGTAGGTAG CAACTGGTTC CAGCCCATCT ACCTCGGAGC
CATGTTCTCC TTGCAAGAAG GGGACAAGCT AATGGTGAAC GTCAGTGACA TCTCTTTGGT
GGATTACACA AAAGAAGATA AAACCTTCTT TGGAGCCTTC TTACTATAGG ATCCGGAGCC
```

TABLE 2-continued

Polynucleotide sequence encoding VEGI-192b (SEQ ID NO:2)

```
GAATTCCACC ACACTGGACT AAGTGGATTC GAGCTCGGTA CCAAAGCTTA AGTTTAAACG
CTAGCCAGCT TGGGTCCCCC TATAGTGAGT CNTATTAATT TCGATAAGCC AGTAAGCAGT
GGGTT
```

TABLE 3

Polynucleotide sequence encoding VEGI-251 (SEQ ID NO:3)

```
TTGTAATACG ACTCACTATA GGGCGGCCGC GAATTCGGCA CGAGATTTAA TGGCCGAGGA
TCTGGGACTG AGCTTTGGGG AAACAGCCAG TGTGGAAATG CTGCCAGAGC ACGGCAGCTG
CAGGCCCAAG GCCAGGAGCA GCAGCGCACG CTGGGCTCTC ACCTGCTGCC TGGTGTTGCT
CCCCTTCCTT GCAGGACTCA CCACATACCT GCTTGTCAGC CAGCTCCGGG CCCAGGGAGA
GGCCTGTGTG CAGTTCCAGG CTCTAAAAGG ACAGGAGTTT GCACCTTCAC ATCAGCAAGT
TTATGCACCT CTTAGAGCAG ACGGAGATAA GCCAAGGGCA CACCTGACAG TTGTGAGACA
AACTCCCACA CAGCACTTTA AAAATCAGTT CCCAGCTCTG CACTGGGAAC ATGAACTAGG
CCTGGCCTTC ACCAAGAACC GAATGAACTA TACCAACAAA TTCCTGCTGA TCCCAGAGTC
GGGAGACTAC TTCATTTACT CCCAGGTCAC ATTCCGTGGG ATGACCTCTG AGTGCAGTGA
AATCAGACAA GCAGGCCGAC CAAACAAGCC AGACTCCATC ACTGTGGTCA TCACCAAGGT
AACAGACAGC TACCCTGAGC CAACCCAGCT CCTCATGGGG ACCAAGTCTG TATGCGAAGT
AGGTAGCAAC TGGTTCCAGC CCATCTACCT CGGAGCCATG TTCTCCTTGC AAGAAGGGGA
CAAGCTAATG GTGAACGTCA GTGACATCTC TTTGGTGGAT TACACAAAAG AAGATAAAAC
CTTCTTTGGA GCCTTCTTAC TATAGGAGGA GAGCAAATAT CATTATATGA AAGTCCTCTG
CCACCGAGTT CCTAATTTTT TTGTTCAAAT GTAATTATAA CCAGGGGTTT TCTTGGGGCC
GGGAGTAGGG GGCATTCCAC AGGGACAACG GTTTAGCTAT GAAATTTGGG GCCCAAAATT
TCACACTTCA TGTGCCTTAC TGATGAGAGT ACTAACTGGA AAAAGGCTGA AGAGAGCAAA
TATATTATTA AGATGGGTTG GAGGATTGGC GAGTTTCTAA ATATTAAGAC ACTGATCACT
AAATGAATGG ATGATCTACT CGGGTCANGA TTGAAAGAGA AATATTTCAA CACCTTCCTG
CTATACAATG GTCACCAGTG GTCCAGTTAT TGTTCAATTT GATCATAAAT TGCTTCAATT
CANGAGCTTT GAAGGAAGTC CAAGGAAAGC TCTAGAAAAC AGTATAAACT TTCAGAGGCA
AAATCCTTCA CCAAATTTTC CACATACTTT CATGCCCTGC CTAAAAAAAA TGAAAAGAA
AAGTTGGTAT GTCTCATGAA TGTTCACACA NAAAGAGTTG GGTTCATGTC ATCCNCAACA
TATGAGAAAA ANCTACCTTC TTTTGNTTAT GTCACAGATT C
```

TABLE 4

Amino acid sequence of VEGI-192a (SEQ ID NO:4)

```
MQLTKGRLHFSHPLSHTKHISPFVTDAPLPADGDKPPAHLTVVRQTPTQHFKNQFPALHW
EHELGLAFTKNRMNYTNKFLLIPESGDYFIYSQVTFRGMTSECSEIRQAGRPNKPDSITV
VITKVTDSYPEPTQLLMGTKSVCEVGSNWFQPIYLGAMFSLQEGDKLMVNVSDISLVDYT
KEDKTFFGAFLL
```

TABLE 5

Amino acid sequence of VEGI-192b (SEQ ID NO:5)

```
METSQEHQGPSDIHRIPWSWGQRNSHAPLRADGDKPPAHLTVVRQTPTQHFKNQFPALHW
EHELGLAFTKNRMNYTNKFLLIPESGDYFIYSQVTFRGMTSECSEIRQAGRPNKPDSITV
VITKVTDSYPEPTQLLMGTKSVCEVGSNWFQPIYLGAMFSLQEGDKLMVNVSDISLVDYT
KEDKTFFGAFLL
```

TABLE 6

Amino acid sequence of VEGI-251 (SEQ ID NO:6)

```
MAEDLGLSFGETASVEMLPEHGSCRPKARSSSARWALTCCLVLLPFLAGLTTYLLVSQL
RAQGEACVQFQALKGQEFAPSHQQVYAPLRADGDKPRAHLTVVRQTPTQHFKNQFPALHW
EHELGLAFTKNRMNYTNKFLLIPESGDYFIYSQVTFRGMTSECSEIRQAGRPNKPDSITV
VITKVTDSYPEPTQLLMGTKSVCEVGSNWFQPIYLGAMFSLQEGDKLMVNVSDISLVDYT
KEDKTFFGAFLL
```

Referring to the sequence alignment comparing the deduced amino acid sequences for SEQ ID NOS: 4, 5, and 6 (Table 7), the C-terminal region of the polypeptides encoded by these SEQ ID's is identical from Val-24 of VEGI-174 to the C-terminus of the protein. However, the N-termini of the four isoforms are different. It is shown in the Examples that VEGI-174 does not inhibit angiogenesis because it is not efficiently exported from the cell upon expression. In contrast, VEGI-251 is efficiently trafficked to the extracellular medium upon expression, and is thereby effective, at inhibiting angiogenesis. Export of VEGI-$_{251}$ results in cleavage of the presequence; the location for proteolysis is believed to be at position 61 or 96 of VEGI-$_{251}$; but may also be located at another site located approximately between Glu-20 and Ser-57 of VEGI-$_{251}$. Possible sites include, but are not limited to, E64, K73, E77, S81, R90, and K95. Purified VEGI-$_{192a}$ polypeptides is also effective at inhibiting vascular endothelial cell growth.

which it is linked in nature, or (3) does not occur in nature, or (4) in the case of polypeptides arise from expression of recombinant polynucleotides.

The present invention also provides nucleic acid molecules (including, as is well understood by one in the art and described herein, isolated and/or recombinant forms) encoding a mature form of the polypeptide proteins described herein. The amino acid sequence of the complete VEGI iso-

TABLE 7

Alignment of the amino acid sequences of the four VEGI isoforms*: (SEQ ID NOS:6, 4, 5, 7)

```
VEGI-251    MAEDLGLSFGETASVEMLPEHGSCRPKARSSSARWALTCCLVLLPFLAGLTTYLLVSQL    59
VEGI-251    RAQGEACVQFQALKGQEFAPSHQQVYAPLRADGDKPRAHLTVVRQTPTQHFKNQFPALHW   119
VEGI-192a   MQLTKGRLHFSHPLSHTKHISPFVTDAPLRADGDKPRAHLTVVRQTPTQHFKNQFPALHW   60
VEGI-192b   METSQEHQGPSDIHRIPWSWGQRNSHAPLRADGDKPRAHLTVVRQTPTQHFKNQFPALHW   60
VEGI-174                  MRRFLSKVYSFPMRKLILFLVFPVVRQTPTQHFKNQFPALHW   42
                                         **
VEGI-251    EHELGLAFTKNRMNYTNKFLLIPESGDYFIYSQVTFRGMTSECSEIRQAGRPNKPDSITV  179
VEGI-192a   EHELGLAFTKNRMNYTNKFLLIPESGDYFIYSQVTFRGMTSECSEIRQAGRPNKPDSITV  120
VEGI-192b   EHELGLAFTKNRMNYTNKFLLIPESGDYFIYSQVTFRGMTSECSEIRQAGRPNKPDSITV  120
VEGI-174    EHELGLAFTKNRMNYTNKFLLIPESGDYFIYSQVTFRGMTSECSEIRQAGRPNKPDSITV  102
VEGI-251    VITKVTDSYPEPTQLLMGTKSVCEVGSNWFQPIYLGAMFSLQEGDKLMVNVSDISLVDYT  239
VEGI-192a   VITKVTDSYPEPTQLLMGTKSVCEVGSNWFQPIYLGAMFSLQEGDKLMVNVSDISLVDYT  180
VEGI-192b   VITKVTDSYPEPTQLLMGTKSVCEVGSNWFQPIYLGAMFSLQEGDKLMVNVSDISLVDYT  180
VEGI-174    VITKVTDSYPEPTQLLMGTKSVCEVGSNWFQPIYLGAMFSLQEGDKLMVNVSDISLVDYT  162
VEGI-251    KEDKTFFGAFLL 251
VEGI-192a   KEDKTFFGAFLL 192
VEGI-192b   KEDKTFFGAFLL 192
VEGI-174    KEDKTFFGAFLL 174
```

*VEGI-$_{174}$ (SEQ ID NO: 7) is referred to previously as VEGI (GenBank accession number AF039390)
**Homologous sequence in all isoforms begins at V$_{24}$ of VEGI-$_{174}$ (SEQ ID NO:7), V$_{101}$ of VEGI-$_{251}$(SEQ ID NO: 6), V$_{42}$ of VEGI-192a (SEQ ID NO:4), and V$_{42}$ of VEGI-192b (SEQ ID NO:5).

Accordingly, the present invention provides isolated nucleic acid molecules comprising sequences corresponding to novel isoforms of VEGI shown in Table 1, 2, and 3 (SEQ ID NO:1, SEQ ID NO:2, and SEQ ID NO:3). The polynucleotides of this invention, including fragments of polynucleotides of this invention, are useful as probes, primers, in expression systems (including in vivo and in vitro expression systems, as described herein, which may also be a basis of gene therapy), and in screening systems. Especially useful applications of the polynucleotides will be discussed below.

By "isolated" nucleic acid molecule is intended a nucleic acid molecule, DNA or RNA, that has been removed from its native environment. In some embodiments, at least 50%, preferably at least 70%, more preferably at least 80%, and even more preferably at least 90% free of the materials with which it is associated in nature have been removed. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules further includes such molecules produced synthetically. Accordingly, an "isolated" polynucleotide or polypeptide also refers to recombinant or other non-naturally occurring forms polynucleotides or polypeptides, which, by virtue of origin or manipulation: (1) are not associated with all or a portion of a polynucleotide or polypeptide with which it is associated in nature, (2) are linked to a polynucleotide or polypeptide other than that to form polypeptide includes a leader sequence and a mature protein. According to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide.

The present invention also provides polynucleotides encoding a fusion protein. As is well known in the art, a fusion protein or polypeptide is a polypeptide comprising regions in a different position than occurs in nature. The regions may normally exist in separate proteins and are brought together in the fusion polypeptide, or they may normally exist in the same protein but are placed in a new arrangement in the fusion polypeptide. Accordingly, the invention provides polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence and a presequence (leader sequence).

The polynucleotides of the present invention provides coding sequence fused in frame to a marker sequence allows for purification or detection of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g., COS-7 cells, is used. The HA tag, corresponds to an epitope derived from the influenza hemagglutinin protein (Wilson. I., et al., *Cell,* 37:767 (1984)).

Thus, the term "polynucleotide encoding a polypeptide" encompasses a polynucleotide which includes only coding sequence for the polypeptide as well as a polynucleotide which includes additional coding and/or non-coding sequence. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

A mutant or a variant of the polynucleotide may be a naturally occurring allelic variant of the polynucleotide or a non-naturally occurring variant of the polynucleotide. Such nucleotide mutants or variants include deletion variants, substitution variants and addition or insertion variants. A variant sequence may result in a truncated or altered polynucleotide or polypeptide, increased or decreased expression of a polynucleotide or polypeptide, or any combination thereof. The variant may be in coding, non-coding, 5' or 3' flanking, genomic or coding nucleotides.

In some embodiments, the polynucleotide sequence comprises a sequence different from those shown Tables 1, 2, or 3 (SEQ ID NO:1, SEQ ID NO:2, and SEQ ID NO:3) due to the degeneracy of the genetic code. Genetic code is well known in the art. It would be routine for one skilled in the art to generate such degenerate variants. Accordingly, in some embodiments, the present invention provides a polynucleotide encoding the polypeptide of SEQ ID NO:4, SEQ ID NO:5, or SEQ ID NO:6.

The present invention is further provides fragments or truncated form of the isolated nucleic acid molecules described herein. By a fragment of an isolated nucleic acid molecule having the nucleotide sequence of the nucleotide sequences herein, or the complementary strand thereto, is intended fragments at least 5 nt, at least 10 nt, at least 15 nt, at least 20 nt, at least 30 nt, at least 40, 50, 100, 150, 200, 250, 300, 400, or 500 nt in length (contiguous nucleotides). These fragments have numerous uses which include, but are not limited to, diagnostic probes and primers as discussed herein. As is well understood in the art, generally a probe is used for detection on a target by hybridization. In some embodiments, a probe may comprise a label or a means by which a label can be attached, either before or subsequent to the hybridization reaction. Suitable labels include, but are not limited to radio-isotopes, fluorochromes, chemiluminescent compounds, dyes, and enzymes. Further, those skilled in the art understand that a primer is generally extended by polymerization after hybridizing to a target sequence. Of course, larger fragments 50-1500 nt in length are also useful according to the present invention. By a fragment at least 20 nt in length, for example, is intended fragments which include 20 or more contiguous bases from the nucleotide sequence. In some embodiments, these fragments comprises nucleotides 93 and 94 of the sequence shown in Table 1 (SEQ ID NO:1) or nucleotides 386 and 387 of the sequence shown in Table 2 (SEQ ID NO:2). Alternatively, fragments may be less than 1500, 1250, 1000, 750, 500, 250, 200, 150, 100, 50, 40 nt in length and comprise nucleotides 93 and 94 of the sequence shown in Table 1 (SEQ ID NO:1) or nucleotides 386 and 387 of the sequence shown in Table 2 (SEQ ID NO:2).

The present invention also provides polynucleotides comprising the sequence of VEGI-$192_a$ (nucleotides 1 to 93 of the sequence shown in Table 1 (SEQ ID NO:1)), or VEGI-$192_b$ (nucleotides 1 to 386 of the sequence shown in Table 2 (SEQ ID NO:2)).

In some embodiments, the invention provides a polynucleotide comprising at least 10, at least 15, at least 18, at least 20, at least 25, at least 30, at least 50, and at least 100 or more contiguous nucleotides of SEQ ID NO:1 (which generally may also be referred to as regions), said contiguous nucleotides are within nucleotides 1 to 93 of the sequence shown in Table 1 (SEQ ID NO:1). In some embodiments, the invention provides a polynucleotide comprising at least 10, at least 15, at least 18, at least 20, at least 25, at least 30, at least 50, and at least 100 or more contiguous nucleotides of SEQ ID NO:1, said contiguous nucleotides comprise nucleotides 93 and 94 of SEQ ID NO:1.

In some embodiments, the invention provides a polynucleotide comprising at least 10, at least 15, at least 18, at least 20, at least 25, at least 30, at least 50, at least 100, at least 150, at least 175, at least 200, at least 250, at least 275, at least 300, at least 350, at least 375, at least 400 or more contiguous nucleotides of SEQ ID NO:2, said contiguous nucleotides are within nucleotides 1 to 386 of the sequence shown in Table 2 (SEQ ID NO:2). In some embodiments, the invention provides a polynucleotide comprising at least 10, at least 15, at least 18, at least 20, at least 25, at least 30, at least 50, at least 100, at least 150, at least 175, at least 200, at least 250, at least 275, at least 300, at least 350, at least 375, at least 400 or more contiguous nucleotides of SEQ ID NO:2, said contiguous nucleotides comprise nucleotides 386 and 387 of SEQ ID NO:2.

The invention provides an isolated polynucleotide comprising a sequence encoding the polypeptide of SEQ ID NO:4. The invention also provides an isolated polynucleotide comprising a sequence encoding at least 5, at least 8, at least 10, at least 15, at least 20, at least 25, or more contiguous amino acids of SEQ ID NO:4, said contiguous amino acids are within amino acid residues 1-26 shown in Table 4 (SEQ ID NO:4). The invention also provides an isolated polynucleotide comprising a sequence encoding at least 5, at least 8, at least 10, at least 15, at least 20, at least 25, or more contiguous amino acids of SEQ ID NO:4, said contiguous amino acids comprise amino acids 26 and 27 of the sequence shown in Table 4 (SEQ ID NO:4). The invention also provides an isolated polynucleotide comprising a sequence encoding amino acid residues 5-192, 10-192, 15-192, 25-192 of the sequence shown in Table 4 (SEQ ID NO:4).

The invention provides an isolated polynucleotide comprising a sequence encoding the polypeptide of SEQ ID NO:5. The invention also provides an isolated polynucleotide comprising a sequence encoding at least 5, at least 8, at least 10, at least 15, at least 20, at least 25, or more contiguous amino acids of SEQ ID NO:5, said contiguous amino acids are within amino acid residues 1-26 shown in Table 5 (SEQ ID NO:5). The invention also provides an isolated polynucleotide comprising a sequence encoding at least 5, at least 8, at least 10, at least 15, at least 20, at least 25, or more contiguous amino acids of SEQ ID NO:5, said contiguous amino acids comprise amino acids 26 and 27 of the sequence shown in Table 5 (SEQ ID NO:5). The invention also provides an isolated polynucleotide comprising a sequence encoding amino acid residues 5-192, 10-192, 15-192, 25-192 of the sequence shown in Table 5 (SEQ ID NO:5).

It is understood that, a region of contiguous amino acids or nucleotides that are within a given pair of amino acids or nucleotides can, but not necessarily, include either member of the specified pair. For example, contiguous nucleotides within nucleotides 1-93 of SEQ ID NO:1 can include nucleotide 1 and/or nucleotide 93 of SEQ ID NO:1.

The embodiments of the present invention excludes polynucleotides encoding a polypeptide consisting of amino acids 27-192 of SEQ ID NO:4 or SEQ ID NO:5 or any truncated form of such polynucleotides.

The invention also provides polynucleotides comprising the sequence encoding any of VEGI polypeptides described herein.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete or mature VEGI polypeptide. Such functional activities include, but are not limited to, biological activity (for example, inhibition of angiogenesis, inhibition of vascular endothelial cell proliferation, induction of cell adhesion, antigenicity (ability, to bind or compete with a VEGI-$_{192a}$ and/or VEGI-$_{192b}$ polypeptide for binding to an anti-VEGI-$_{192a}$ and/or anti-VEGI-$_{192b}$ antibody), immunogenicity (ability to generate antibody which binds to a VEGI-$_{192a}$ and/or VEGI-$_{192b}$ polypeptide), the ability to form polymers with other VEGI polypeptides. and ability to bind to a receptor or ligand for a VEGI polypeptide (for example, DR3).

Similarly, the VEGI polypeptides encoded by any of the polynucleotides described herein may have one or more functional activities of VEGI as described above and herein.

Another embodiment of the invention provides an isolated polynucleotide having at least 85%, at least 88%, at least 90%, at least 92%, at least 94%, at least 96%, at least 98%, or at least 99% sequence identity with the polynucleotides of the invention as described herein. One embodiment provides an isolated polynucleotide having at least 85%, at least 88%, at least 90%, at least 92%, at least 94%, at least 96%, at least 98%, or at least 99% sequence identity with the VEGI-$_{192a}$ or VEGI-$_{192b}$ sequence shown in Table 1 or Table 2 (SEQ ID NO:1 or SEQ ID NO:2). In other embodiments, isolated polynucleotides additionally have less than 85%, 83%, 80%, 75%, 70% sequence identity with the above VEGI-$_{192a}$ or VEGI-$_{192b}$ sequence. The invention also includes isolated polynucleotides having at least 85%, at least 88%, at least 90%, at least 92%, at least 94%, at least 96%, at least 98%, or at least 99% sequence identity to fragments of at least 10 contiguous nucleotides (or more, such as 15, 18, 20, 25, 35, 40, 45, 50, 60, 75, or 100 contiguous nucleotides) of the sequence shown in Table 1 (SEQ ID NO:1) or 2 (SEQ ID NO:2), wherein the contiguous nucleotides comprise nucleotides 93 and 94 of SEQ ID NO:1, or nucleotides 386 and 387 of SEQ ID NO:2. In some embodiments, the polynucleotides having at least 85%, at least 88%, at least 90%, at least 92%, at least 94%, at least 96%, at least 98%, or at least 99% sequence identity to fragments of at least 10 contiguous nucleotides (or more, such as 15, 18, 20, 25, 35, 40, 45, 50, 60, 75, or 100 contiguous nucleotides of the sequence shown in Table 1 (SEQ ID NO: 1) or of the sequence shown in Table 2 (SEQ ID NO:2), wherein the contiguous nucleotides are within nucleotides 1-93 of SEQ ID NO:1 or nucleotides 1-386 of SEQ ID NO:2.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in Current Protocols in Molecule Biology (F. M. Ausubel et al., eds., 1987) Supplement 30, section 7.718, Table 4.7.1. Percent identity can be determined electronically, e.g., by using the MegAlign.TM. program (DNASTAR, Inc., Madison Wis.). The MegAlign.TM. program can create alignments between two or more sequences according to different methods, e.g., the clustal method. (See, e.g., Higgins, D. G. and P. M. Sharp (1988) Gene 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626-645.)

The invention also provides an isolated nucleic acid that hybridizes under high stringency conditions to a nucleic acid having a sequence complementary to the nucleotide sequence selected from the group consisting of SEQ ID NO:1, and SEQ ID NO:2, or to the nucleic acid having a sequence complementary to a nucleotide encoding polypeptide of SEQ ID NO:4 or SEQ ID NO:5, or their complement thereof.

In terms of hybridization conditions, the higher the sequence identity required, the more stringent are the hybridization conditions if such sequences are determined by their ability to hybridize to a polynucleotide sequence of the invention. Accordingly, the invention also includes polynucleotides that are able to hybridize to a sequence comprising a polynucleotide of the invention as discussed herein. An example of stringent hybridization conditions is overnight incubation at 42° C. in a solution: 50% formamide, 1×SSC (150 mM sodium chloride, 15 mM sodium citrate), 50 mM sodium phosphate (pH 7.6), 5× denhardt's solution, 10% dextran sulfate, and 20 ug/ml denatured, sheared salmon sperm DNA, followed by washing the filters in 0.1×SSC at about 65° C. For discussion regarding hybridization reactions, see below.

In one embodiment, the invention provides an isolated polynucleotide comprising a sequence of at least 10 contiguous nucleotides (or more, such as 15, 18, 20, 25, 35, 40, 45, 50, 60, 75, or 100 (or more) contiguous nucleotides) that hybridizes with a polynucleotide (such as DNA or RNA) comprising the sequence depicted in Table 1 (SEQ ID NO:1) or Table 2 (SEQ ID NO:2), or fragments thereof, as described above, under conditions where it does not hybridize with other polynucleotides from a mammalian cell, preferably a human cell, or under conditions in which hybridization to the polynucleotide having the sequence depicted in Table 1 (SEQ ID NO:1) or Table 2 (SEQ ID NO:2) is enriched relative to hybridization with other polynucleotides from a mammalian cell. In some embodiments, the fragments comprise nucleotides 93 and 94 of SEQ ID NO:1 or nucleotides 386 and 387 of SEQ ID NO:2. In some embodiments, the fragments are within nucleotides 1-93 of SEQ ID NO:1 or nucleotides 1-386 of SEQ ID NO:2.

These embodiments are particularly useful in the diagnostic (detection) context.

In another embodiment, the invention includes a polynucleotide sequence comprising at least 10, preferably 15, preferably 18, preferably 20, more preferably 25, more preferably 35, more preferably 50, still more preferably 75, 100, 125, 150, 200, 250 contiguous nucleotides of the non-coding (i.e., flanking) shown in Table 1 (SEQ ID NO:1) or Table 2 (SEQ ID NO:2). These embodiments may be particularly useful as diagnostic probes, or as primers for amplification of noncoding portions of the VEGI-$192a$ or VEGI-$192b$ gene.

It is understood that (unless otherwise specified or required), any embodiment of the invention described herein that is a polynucleotide encompasses both the double-stranded form and each of two complementary single-stranded forms known or predicted to make up the double stranded form.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM sodium chloride, 15 mM sodium citrate), 50 mM sodium phosphate (pH 7.6), 5× denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

The invention also provides primers and probes comprising a region of SEQ ID NO:1 or SEQ ID NO:2, wherein the region is within nucleotides 1-93 of SEQ ID NO:1 or nucleotides 1-386 of SEQ ID NO:2. The invention also provides primers and probes comprising a region of SEQ ID NO:1 or SEQ ID NO:2, wherein the region comprises nucleotides 93 and 94 of SEQ ID NO:1 or nucleotides 386 and 387 of SEQ ID NO:2.

Probes from more than one polynucleotide sequence provided herein can hybridize with the same nucleic acid if the cDNA from which they were derived corresponds to one mRNA. By using probes, particularly labeled probes of DNA sequences, one can isolate homologous or related genes. The source of homologous genes can be any species, e.g. primate species, canines, felines, bovines, ovines, equines, yeast, nematodes. Probes of more than 10 nucleotides ("nt") can be used, e.g. probes of a size within a range of about 15 nt, 18 nt, 20, nt, 25 nt, 75 nt, or 100 nt, but in general about 15 nt represents sufficient sequence for unique identification.

"Tm" is the temperature in degrees Centigrade at which 50% of a polynucleotide duplex made of complementary strands hydrogen bonded in anti-parallel direction by Watson-Crick base pairing dissociates into single strands under conditions of the experiment. Tm may be predicted according to a standard formula, such as:

$$Tm = 81.5 + 16.6 \log[X^+] + 0.41(\% \ G/C) - 0.61(\% \ F) - 600/L$$

where $[X^+]$ is the cation concentration (usually sodium ion, Na+) in mol/L; (% G/C) is the number of G and C residues as a percentage of total residues in the duplex; (% F) is the percent formamide in solution (wt/vol); and L is the number of nucleotides in each strand of the duplex.

As described above, the invention includes variants or modifications to the VEGI-$192a$ and VEGI-$192b$ polynucleotides such as deletions, substitutions, additions, or changes in the nature of any nucleic acid moieties. A variant or modification is any difference in nucleotide sequence as compared to a polynucleotide shown herein to encode a VEGI-$192a$ or a VEGI-$192b$ polypeptide, and/or any difference in terms of the nucleic acid moieties of the polynucleotide(s). Such changes can be useful to facilitate cloning and modifying expression of VEGI-$192a$ or VEGI-$192b$ polynucleotides. Such changes also can be useful for conferring desirable properties to the polynucleotide(s), such as stability. The definition of polynucleotide provided herein gives examples of these modifications. Hence, the invention also includes functionally-preserved variants of the nucleic acid sequences disclosed herein, which include nucleic acid substitutions, additions, and/or deletions. Variants include naturally occurring variants of the polynucleotide sequence (e.g. degenerate variants, allelic variants, etc. In general, allelic variants contain 15-25% base pair (bp) mismatches and can contain as little as 5-15%, or 2-5%, or 1-2% bp mismatch, as well as a single bp mismatch.

Figure 6:
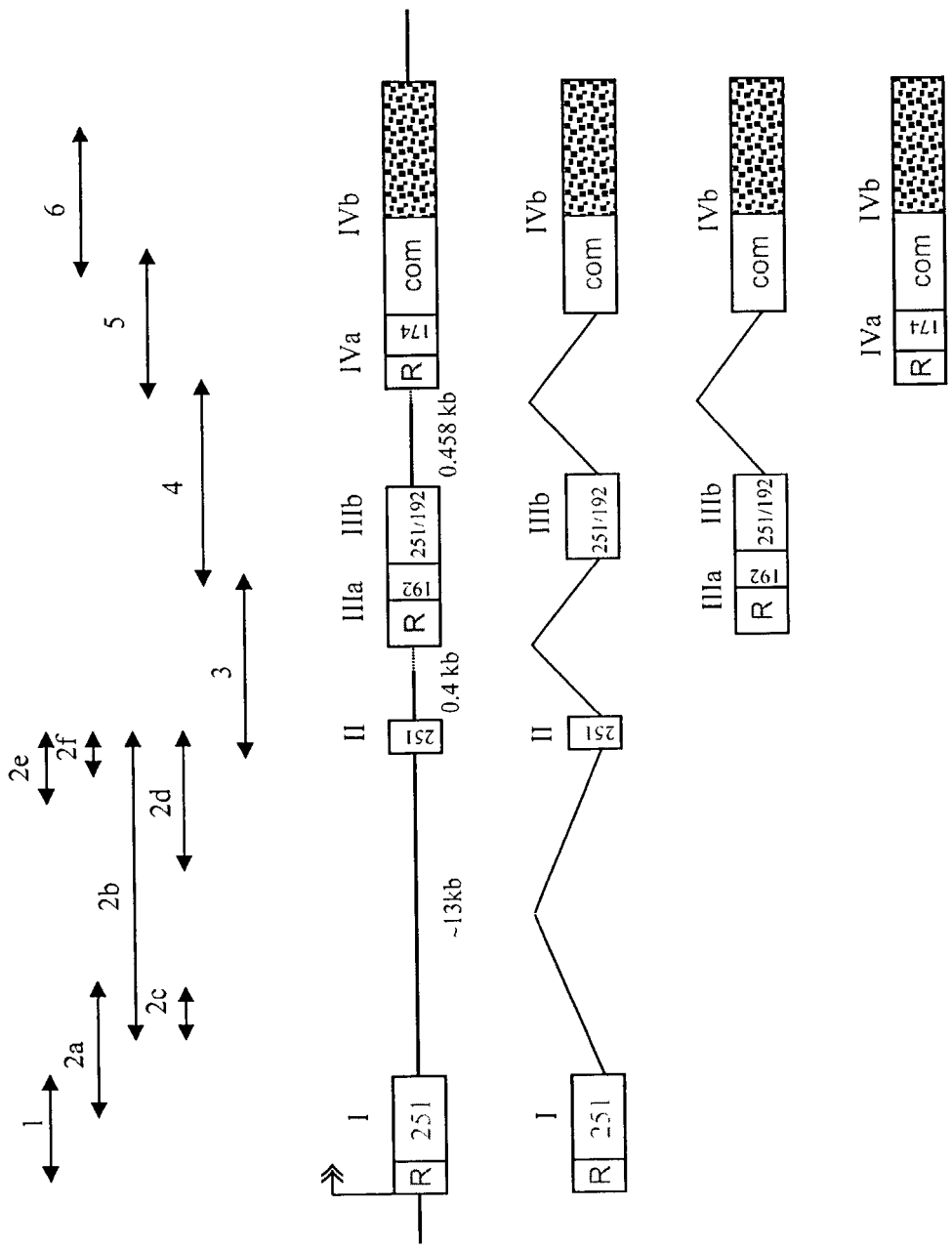
FIG. 6. Gene structure of human VEGI and proposed generation of isoforms. The segments numbered 1 through 9 represent the PCR fragments generated during gene mapping, with specific primer pairs listed in Materials and Methods. Boxes with roman numerals above represent exons and horizontal lines represent intronic sequence. The putative transcription start site is indicated by a double arrowhead. R denotes the 5' untranslated sequence unique to each respective transcript, and stippled boxes represent the common 3' untranslated region. Approximate sizes of the introns are indicated. VEGI-$_{251}$, VEGI-$_{192a}$, or VEGI-$_{174}$ specific sequences are labeled '$_{251}$', '192' or '$_{174}$'. Exon IIIb encodes residues shared by both VEGI-$_{251}$ and VEGI-$_{192a}$. The introns 5' of exons III and IV are dashed because the 5' ends or initiation sites of VEGI-$_{192a}$ and VEGI-$_{174}$ transcripts have not been determined. 'COM' denotes the coding region of the last exon that is common to all three isoforms.

As described above, the invention encompasses VEGI-$192a$ or VEGI-$192b$ polynucleotides including full-length (unprocessed), processed, coding, non-coding or portions thereof. A partial map of the VEGI-$192a$ genomic region is shown in FIG. 6, including predicted intron-exon boundaries. The invention can further include the 3' and 5' untranslated regions found in the mature mRNA, specific transcriptional and translational regulatory sequences, such as promoters, enhancers, etc., including about 1 kb, and possibly more of flanking genomic DNA at either the 5' or 3' end of the transcribed region. The genomic DNA can be isolated as a fragment of 100 kbp or smaller, and substantially free of flanking chromosomal sequence. The genomic DNA flanking the coding region, either 3' or 5', or internal regulatory sequences as sometime found in introns, contains sequences required for proper tissue, stage-specific or disease-state specific expression. Also embodied are the mRNA and cDNA sequences and fragments thereof, including fragments that include a portion of a VEGI-$192a$ or VEGI-$192b$ encoding segment. Normally, mRNA species have contiguous exons, with the intervening introns, when present, being removed by nuclear RNA splicing, to create a continuous open reading frame encoding a polypeptide. mRNA species can also exist with both exons and introns, where the introns may be removed by alternative splicing. Furthermore, different species of mRNAs encoded by the same genomic species can exist at varying levels in a cell, and detection of these various levels of mRNA species can be indicative of differential expression of the encoded gene product in the cell.

The invention also encompasses polynucleotides encoding for functionally equivalent variants and derivatives of full-length VEGI-$_{192a}$ or VEGI-$_{192b}$ and functionally equivalent fragments (such as deletion of amino acids from N-terminal and/or from C-terminal of VEGI-$_{192a}$, or VEGI-$_{192b}$) thereof which may enhance, decrease or not significantly affect properties of the polypeptides encoded thereby. For instance, changes in a DNA sequence that do not change the encoded amino acid sequence, as well as those that result in conservative substitutions of amino acid residues, non-deleterious non-conservative substitutions, one or a few amino acid deletions or additions, and substitution of amino acid residues by amino acid analogs are those which will not significantly affect properties of the encoded polypeptide. Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of VEGI. Alternatively processed polynucleotide sequence variants are defined as polynucleotide sequences corresponding to mRNAs that differ in sequence for one another but are derived from the same genomic region, for example, mRNAs that result from: 1) the use of alternative promoters; 2) the use of alternative polyadenylation sites; or 3) the use of alternative splice sites.

This invention also provides a DNA insert comprising a nucleic acid having a nucleotide sequence of SEQ ID NO:1 or a complement thereof. In other embodiment, the invention provides a DNA insert comprising a nucleic acid having a nucleotide sequence of SEQ ID NO:2 or a complement thereof.

As well understood in the art, a "polynucleotide" refers to a polymeric form of nucleotides of any length, which contain deoxyribonucleotides, ribonucleotides, and/or their analogs. The terms "polynucleotide" and "nucleic acid" as used herein are used interchangeably, and as is well known in the art. Polynucleotides may have any three-dimensional structure. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form. Not all linkages in a polynucleotide need be identical.

In some embodiments, a polynucleotide may comprise modified nucleotides, such as methylated nucleotides and nucleotide analogs. The use of uracil as a substitute for thymine in a deoxyribonucleic acid is also considered an analogous form of pyrimidine.

As is widely known in the art, if present, modification to the nucleotide structure may be imparted before or after assembly of the polymer. In some embodiments, the sequence of nucleotides may be interrupted by non-nucleotide components. As described herein, a polynucleotide may be further modified after polymerization, such as by conjugation with a labeling component. Other types of modifications are, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ploy-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). All of these modifications are well known in the art.

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping group moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and a basic nucleoside analogs such as methyl riboside.

Although conventional sugars and bases are generally used, substitution of analogous forms of sugars, purines and pyrimidines can be advantageous in designing a final product, as can alternative backbone structures like a polyamide backbone or phosphorothioate backbone.

This invention encompasses compositions, including pharmaceutical compositions, comprising polynucleotides described herein. These compositions may further comprise suitable excipients, such as pharmaceutically acceptable excipients including buffers, which are well known in the art.

This invention also provides kits comprising any of the polynucleotides described herein. In some embodiments, the kits comprise polynucleotides of SEQ ID NO:1 and/or SEQ ID NO:2. In some embodiments, the kits comprise polynucleotides encoding a polypeptide of SEQ ID NO:4 and/or SEQ ID NO:5. In some embodiments, the kits comprise probes and primers comprising at least 15 contiguous, at least 20, at least 25, at least 30, or at least 50 nucleotides of SEQ ID NO:1 or SEQ ID NO:2, said contiguous nucleotides are within nucleotides 1-93 of SEQ ID NO:1 or nucleotides 1-386 SEQ ID NO:2. These kits may further include reagents and instructions for detecting the presence or absence or the level of expression of VEGI-$_{192a}$ and/or VEGI-$_{192b}$. The kits of this invention are in suitable packaging, and may optionally provide additional components such as, buffers and instructions.

This invention also provides polynucleotides described herein attached to a solid support. Methods of attaching polynucleotides to a solid support, for example surface of arrays, are well known in the art. The solid support is of any suitable material, including polystyrene based beads and glass chips, such as a GeneChip.RTM. product (Affymetrix, Inc., Santa Clara, Calif.). See International Publication Nos. WO 97/10365, WO 97/29212, WO 97/27317, WO 95/11995, WO 90/15070, and U.S. Pat. Nos. 5,744,305 and 5,445,934.

This invention also provides arrays comprising VEGI-$_{192a}$ and/or VEGI-$_{192b}$ polynucleotides. Polynucleotide arrays provide a high throughput technique that can assay a large number of polynucleotides or polypeptides in a sample. This technology can be used as a tool to test for differential expression. A variety of methods of producing arrays, as well as variations of these methods, are known in the art and contemplated for use in the invention. For example, arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Alternatively, the polynucleotides of the test sample can be immobilized on the array, and the probes detectably labeled. Techniques for constructing arrays and methods of using these arrays are described in, for example, Schena et al. (1996) Proc Natl Acad Sci USA. 93(20):10614-9; Schena et al. (1995) Science 270(5235):467-70; Shalon et al. (1996) Genome Res. 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

Arrays can be used to examine differential expression of genes and can be used to determine gene function. For example, arrays can be used to detect differential expression of a VEGI isoform corresponding to a polynucleotide described herein, where expression is compared between a test cell and control cell. For example, high expression of a particular VEGI isoform message in an cell from a subject who has a disease, which is not observed in a corresponding normal cell, can indicate an association of this VEGI isoform with such disease. Exemplary uses of arrays are further described in, for example, Pappalarado et al., Sem. Radiation Oncol. (1998) 8:217; and Ramsay Nature Biotechnol. (1998) 16:40. Furthermore, many variations on methods of detection using arrays are well within the skill in the art and within the scope of the present invention. For example, rather than immobilizing the probe to a solid support, the test sample can be immobilized on a solid support which is then contacted with the probe.

A VEGI isoform polynucleotide that is differentially expressed in a cell from an individual having a disease would be of clinical significance with respect to this disease. A VEGI isoform polynucleotide is differentially expressed in a cell when the polynucleotide is detected at higher or lower levels in a cell of an individual having a disease compared to a cell of the same cell type that is from an individual who does not having the disease. Typically, screening for polynucleotides differentially expressed focuses on a polynucleotide that is expressed such that, for example, mRNA is found at levels at least about 25%, at least about 50% to about 75%, at least about 90%, at least about 2-fold, at least about 4-fold; at least about 5-fold, at least about 10-fold, or at least about 50-fold or more, higher (e.g. overexpressed) or lower (e.g., underexpressed) in a cell from an individual who has the disease when compared with a cell of the same cell type that is not from such an individual. The comparison can be made between two tissues, for example, if one is using in situ hybridization or another assay method that allows some degree of discrimination among cell types in the tissue. The comparison may also be made between cells removed from their tissue source.

Thus, the invention provides an array comprising a VEGI isoform polynucleotides as described herein. In some embodiments, the invention provides an array comprising a polynucleotide sequence shown is Table 1 (SEQ ID NO:1), or a region of polynucleotide of the sequence shown in Table 1 (SEQ ID NO:1), wherein said region is at least 10 contiguous nucleotides (or more, such as at least 15, 18, 20, 25, 35, 40, 45, 50, 60, 75 or 100 contiguous nucleotides). In other embodiments, the region further comprises nucleotides 93 and 94 of the sequence shown in Table 1 (SEQ ID NO:1). In other embodiments, the region is within nucleotides 1-93 of the sequence shown in Table 1 (SEQ ID NO:1).

In some embodiments, the invention provides an array comprising a polynucleotide sequence shown in Table 2 (SEQ ID NO:2), or a region of polynucleotide of the sequence shown in Table 2 (SEQ ID NO:2), wherein said region is at least 10 contiguous nucleotides (or more, such as at least 15, 18, 20, 25, 35, 40, 45, 50, 60, 75 or 100 contiguous nucleotides). In other embodiments, the region further comprises nucleotides 386 and 387 of the sequence shown in Table 2 (SEQ ID NO:2). In other embodiments, the region is within nucleotides 1-386 of the sequence shown in Table 1 (SEQ ID NO:1).

Arrays are also useful for detecting mutant VEGI isoform polynucleotides. Mutant VEGI isoform polynucleotides can be detected in genomic DNA, e.g., genomic DNA isolated from the blood of an individual or from another tissue sample. Mutant VEGI isoform polynucleotides can also be detected using cDNA or mRNA from an individual possessing an altered VEGI isoform polynucleotide, if the mutant VEGI isoform polynucleotide results in an mRNA that is altered in size (for example). A mutant VEGI isoform gene may also result in the differential expression (increased or decreased) of a VEGI isoform mRNA, which can be detected as described herein.

The present invention also provides an array comprising one or more isolated polynucleotides that specifically hybridize to the polynucleotide described herein. In some embodiments, the invention provides an array comprising one or more isolated polynucleotides that specifically hybridize to the polynucleotide shown in Table 1 (SEQ ID NO:1), or a region of polynucleotide of the sequence shown in Table 1 (SEQ ID NO:1), wherein said region is at least 10 contiguous nucleotides (or more, such as at least 15, 18, 20, 25, 35, 40, 45, 50, 60, 75 or 100 contiguous nucleotides). In other embodiments, the region further comprises nucleotides 93 and 94 of the sequence shown in Table 1 (SEQ ID NO:1). In other embodiments, the region is within nucleotides 1-93 of the sequence shown in Table 1 (SEQ ID NO:1).

In other embodiments, the invention provides an array comprising one or more isolated polynucleotides that specifically hybridize to a polynucleotide sequence shown in Table 2 (SEQ ID NO:2), or a region of polynucleotide of the sequence shown in Table 2 (SEQ ID NO:2), wherein said region is at least 10 contiguous nucleotides (or more, such as at least 15, 18, 20, 25, 35, 40, 45, 50, 60, 75 or 100 contiguous nucleotides). In other embodiments, the region further comprises nucleotides 386 and 387 of the sequence shown in Table 2 (SEQ ID NO:2). In other embodiments, the region is within nucleotides 1-386 of the sequence shown in Table 1 (SEQ ID NO:1).

Polypeptides of the Invention

The present invention encompasses human VEGI-$_{192a}$, VEGI-$_{192b}$, and VEGI-$_{251}$ polypeptide sequences shown in Tables 4 (SEQ ID NO:4), 5 (SEQ ID NO:5), and 6 (SEQ ID NO:6). The VEGI polypeptides can be recovered and purified from recombinant cell cultures by methods including ammonium sulfate or ethanol precipitation., acid extraction, anion or cation exchange chromatography, phosphocellulose chromatography, hydrophobic interaction chromatography, affinity chromatography, hydroxylapatite chromatography and lectin chromatography. Protein refolding steps can be used as necessary in completing configuration of the mature protein. Finally, high performance liquid chromatography (HPLC)

can be employed for final purification steps. Examples of protein refolding and purification methods are described in U.S. Pat. Appl. 20010044521 and WO 01/55174.

The polypeptides of the present invention may be a naturally purified product or a product of chemical synthetic procedures, or produced by recombinant techniques from a prokaryotic (such as E.coli) or eukaryotic host (such as CHO cells). Depending upon the host employed in a recombinant production procedure, the polypeptides of the present invention may be glycosylated or may be non-glycosylated. Polypeptides of the invention may also include an initial methionine amino acid residue.

The VEGI-$_{192a}$, VEGI-$_{192b}$, and VEGI-$_{251}$ polypeptides of the invention (which, as described herein, include various embodiments, such as full-length, muture, fusion, fragments, etc.) have a variety of uses, as described herein. The polypeptides are of particular interest as genetic or biochemical markers (e.g., in blood or tissues) that indicate angiogenesis related disease, and/or to monitor the efficacy of various therapies and preventative interventions. Diagnostic (i.e., detection) and screening methods are described in more detail below. The polypeptides of the invention also are of use in making antibodies that bind to these polypeptides, their use as an agent to screen pharmaceutical candidates (both in vitro and in vivo), their use in rational (i.e., structure-based) drug design, as well as other uses include therapeutic uses which are described herein (for example, if full-length VEGI-$_{192a}$ or VEGI-$_{192b}$ exerts its action by binding to another protein, a polypeptide that binds competitively to VEGI-$_{192a}$ or VEGI-$_{192b}$ could compromise VEGI-$_{192a}$ or VEGI-$_{192b}$ function as a competitive inhibitor and thus exert therapeutic activity). The VEGI-$_{192a}$ or VEGI-$_{192b}$ polypeptides may also be used to identifying proteins especially those from humans that bind (or interact physically) with VEGI-$_{192a}$ or VEGI-$_{192b}$ which could thus themselves be drug targets.

The invention provides polypeptide, truncated forms, or fragments, of VEGI-$_{192a}$ and VEGI-$_{192b}$. The VEGI polypeptides of the invention have one or more functions, as described in the previous section. In some embodiments, the VEGI polypeptide serves to bind a specific antibody. In other embodiments a VEGI polypeptide is an immunogen. In yet other embodiments a VEGI polypeptide inhibits vascular endothelial cell growth and/or angiogenesis. Methods for testing the activity of a VEGI polypeptide (including a truncated form of VEGI) is well known in the art and are described in the Examples in detail, such as assay for testing effect on vascular endothelial cell growth, capillary-like tube formation, capillary growth in collagen gels placed on chick embryo chorioallantoic membrane, xenograft tumor growth.

The size of the polypeptide fragments may vary widely. Thus, the invention includes polypeptide fragments of full-length VEGI-$_{192a}$ or VEGI-$_{192b}$ comprising a portion of the amino acid sequence depicted in Table 4 (SEQ ID NO:4) or Table 5 (SEQ ID NO:5) in which the VEGI-$_{192a}$ or VEGI-$_{192b}$ polypeptide is at least about 5, about 10, about 15, 25, 50, 75, 100, 150, or more contiguous amino acids of a sequence shown in Table 4 (SEQ ID NO:4) or Table 5 (SEQ ID NO:5). It is understood that the fragments comprising at least one amino acids within amino acids 1-26 of SEQ ID NO:4 or SEQ ID NO:5, preferably a region, within amino acids 1-26 of SEQ ID NO:4 or SEQ ID NO:5. In some embodiments, the portion of the amino acid sequence comprises amino acids 26 and 27 shown in Table 4 (SEQ ID NO:4) or Table 5 (SEQ ID NO:5). In some embodiments, the portion of the amino acid sequence are within amino acids 1-26 of SEQ ID NO:4 or SEQ ID NO:5. As is evident to one skilled in the art, these polypeptides, regardless of their size, may also be associated with, or conjugated with, other substances or agents to facilitate, enhance, or modulate function and/or specificity of a VEGI-$_{192a}$ or a VEGI-$_{192b}$ polypeptide. These fragments may be used for a variety of purposes, including as an immunogen (either alone or in conjunction with a suitable agent), or as an agent to inhibit angiogenesis. The fragments (as with polypeptides) should have one or more of the biological functions described above for a VEGI polypeptide. In some embodiments, the fragments inhibit angiogenesis. The truncated forms may be less than about any of the following: 185, 170, 160, 150, 125, 100, 80, 50, 40, 25, 20, 15, or 10 amino acids.

It is understood that, a region of contiguous amino acids or nucleotides that are within a given pair of amino acids or nucleotides can, but not necessarily, include either member of the specified pair. For example, the contiguous amino acids within amino acids 1-26 of SEQ ID NO:4 can include amino acid 1 and/or amino acid 26 of SEQ ID NO:4.

In some embodiments of the invention, the polypeptides of the invention comprise at least 5, at least 8, at least 10, at least 15, at least 20, at least 25, or more contiguous amino acids within amino acid residues 1-26 shown in Table 4 (SEQ ID NO:4) or Table 5 (SEQ ID NO:5) (which generally may also be referred to as regions). The invention also provides polypeptides comprising amino acid residues about 5-192, 10-192, 15-192, 20-192, 25-192 of the sequence shown in Table 4 (SEQ ID NO:4) or Table 5 (SEQ ID NO:5).

The embodiments of the present invention excludes any polypeptides consisting of amino acids 27-192 of SEQ ID NO:4 or SEQ ID NO:5 or a truncated form of such polypeptides.

The present invention further include polypeptides which have at least 90% similarity, more preferably at least 95% similarity, and still more preferably at least 96%, 97%, 98% or 99% similarity to those described above. The polypeptides of the invention also comprise those, which are at least 80% identical, more preferably at least 90%, or 95% identical, still more preferably at least 96%, 97%, 98% or 99% identical to the polypeptides described herein and also include portions of such polypeptides with at least 30 amino acids and more preferably at least 50 amino acids. In some embodiments, the invention provides polypeptides which have at least 90% similarity, more preferably at least 95% similarity, and still more preferably at least 96%, 97%, 98% or 99% similarity to the polypeptide of SEQ ID NO:4 or the polypeptide of SEQ ID NO:5. The polypeptides of the invention also comprise those, which are at least 80% identical, more preferably at least 90%; or 95% identical, still more preferably at least 96%, 97%, 98% or 99% identical to the polypeptide of SEQ ID NO:4 or the polypeptide of SEQ ID NO:5.

This invention also provides fusion proteins comprising polypeptides described herein. The polypeptides described herein can be fused with sequences, such as sequences that enhance immunological reactivity, facilitate the coupling of the polypeptide to a support or a carrier, or facilitate purification (e.g., sequences encoding epitopes such as Myc, HA derived from influenza virus hemagglutinin, His-6, or FLAG). In addition, the protein or polynucleotide can be fused to other or polypeptides which increase its function, or specify its localization in the cell, such as a secretion sequence is discloses herein. For Methods for producing the recombinant fusion protein described above are common in the art. The recombinant or fusion protein can be isolated by methods well known in the art. Tile transformed host cells can be used to analyze the effectiveness of drugs and agents which inhibit or activate VEGI function, such as host proteins or chemically derived agents or other proteins which interact with VEGI polynucleotides to down-regulate or alter the expression of VEGI polypeptides or affect its ability to inhibit angiogenesis. A method for testing the effectiveness of an anti-VEGI or anti-angiogenesis drug or agent can for example, be the blockage of the endothelial cell growth inhibitor.

This invention encompasses compositions, including pharmaceutical compositions, comprising polypeptides described herein. In some embodiments, the composition comprises polypeptide of SEQ ID NO:4. This composition is useful for inhibiting angiogenesis. These compositions may further comprise suitable excipients, such as pharmaceutically acceptable excipients including buffers, which are well known in the art.

This invention also provides kits comprising polypeptides described herein. In some embodiments, the composition comprises polypeptide of SEQ ID NO:4. In some aspects, the kits may be used for treating pathological angiogenesis, inhibiting angiogenesis, or treating cancer such as reducing tumor size. The kits of this invention are in suitable packaging, and may optionally provide additional components such as, buffers and instructions.

This invention also provides polypeptides described herein attached to a solid support. Methods of making such attachment, for example attaching to an array surface, are well known in the art. The polypeptides of the invention attached to a solid support, such as, particles of agarose, SEPHADEX, or the like, are useful for screening molecules that selectively binding the polypeptides describe herein.

The invention also encompasses an array comprising VEGI isoform polypeptides of the invention, as described herein. Therefore, in one aspect, the invention provides an array comprising VEGI isoform polypeptides encoded by a polynucleotide of the invention as described herein. In other aspect, the invention provides an array comprising a polypeptide comprising the sequence shown in Table 4 (SEQ ID NO:4), or a region thereof, wherein the region is at least 5 contiguous amino acids in length (or more, e.g. at least 10, 15, 25, 50, 75, 100, 150, or more amino acids in length). In some embodiments, the region comprises amino acids 26 and 27 of the sequence shown in Table 4 (SEQ ID NO:4). In other embodiments, the region is within amino acids 1-26 of the sequence shown in Table 4 (SEQ ID NO:4).

In other aspect, the invention also provides an array comprising a polypeptide comprising the sequence shown in Table 5 (SEQ ID NO:5), or a region thereof, wherein the region is at least 5 contiguous amino acids in length (or more, e.g. at least 10, 15, 25, 50, 75, 100, 150, or more amino acids in length). In some embodiments, the region comprises amino acids 26 and 27 of the sequence shown in Table 5 (SEQ ID NO:5). In other embodiments, the region is within amino acids 1-26 of the sequence shown in Table 5 (SEQ ID NO:5).

The terms "polypeptide", and "protein" are used interchangeably herein, and, as is well-known in the art to refer to polymers of amino acids of any length. In various embodiments, the polymer may be linear or branched, it may comprise modified amino acids, it may be interrupted by non-amino acids, and/or it may be assembled into a complex of more than one polypeptide chain. As is well understood in the art, a polypeptide may be modified naturally or by intervention; for example, disulfide bond formation, glycosylation, lipidation, acetylation, phosphorylation, or any other manipulation or modification, such as conjugation with a labeling component. In some embodiments, polypeptides contain one or more analogs of an amino acid (including, for example, unnatural amino acids, etc.), as well as other modifications known in the art.

This invention also includes functionally preserved variants of the VEGI polypeptides described herein. Such variants may be made using methods standard in the art, for example, by conservative amino acid substitutions. In various embodiments, a functionally preserved variant comprises preserved variant comprises (or, in some embodiments, consist of) any of one, two, three, four, five, six, seven, eight, nine, ten conservative amino acid substitutions.

Vectors and Host Cells

The present invention also relates to vectors which include the isolated polynucleotides of the present invention, host cells which are genetically engineered with the recombinant vectors, or which are otherwise engineered to produce the polypeptides of the invention, and the production of polypeptides of the invention by recombinant techniques.

The term "vector" refers to a plasmid, virus or other vehicle known in the art that has been manipulated by insertion or incorporation of the VEGI-$_{251}$, VEGI-$_{192a}$ or VEGI-$_{192b}$ genetic sequences or fragments thereof. This polynucleotide (generally, DNA) element which renders the vector suitable for multiplication can be an origin of replication which works in prokaryotic or eukaryotic cells. An example for an origin of replication which works in prokaryotic cells is the colE1 ori. A recombinant vector needs further a selection marker for control of growth of these organisms which harbor the vector. Suitable selection markers include genes which protect organisms from antibiotics (antibioticum resistance), for example, ampicillin, streptomycin, chloramphenicol or provide growth under compound deprived environmental conditions (auxotrophic growth conditions) when expressed as proteins in cells. In a preferred embodiment of the invention for multiplication of the recombinant vector the prokaryotic cells are bacteria. In special preferred versions of the inventions the bacteria are in particular bacteria of *Escherichia coli* or of *Bacillus* sp. In a further preferred embodiment of the invention for the multiplication of the recombinant vector the eukaryotic cells are cells of a cell line or yeast cells. In special preferred versions of the invention the cells of the cell line are cells of a CHO, COS, Hela-, or 3T3-cell-line and the yeast cells are cells of *Saccharomyces cerevisiae*.

The present invention includes a variety of vectors (i.e., cloning and/or expression vectors, as well as vectors for cloning and/or replication) having cloned therein VEGI-$_{192a}$, VEGI-$_{192b}$, or VEGI-$_{251}$ polynucleotide(s). These vectors can be used for expression of recombinant polypeptides as well as a source of VEGI-$_{192a}$, VEGI-$_{192b}$, or VEGI-$_{251}$ polynucleotides. Cloning vectors can be used to obtain replicate copies of the VEGI-$_{192a}$, VEGI-$_{192b}$, or VEGI-$_{251}$ polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express VEGI-$_{192a}$, VEGI-$_{192b}$, or VEGI-$_{251}$ polypeptides in an individual, such as for eliciting an immune response via the polypeptide(s) encoded in the expression vector(s). Suitable cloning and expression vectors include any known in the art e.g., those for use in bacterial, mammalian, yeast and insect expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide encoding a VEGI polypeptide of interest. The polynucleotide encoding the VEGI polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from VEGI polynucleotides (i.e., one of the VEGI isoform gene), or they may be heterologous (i.e., derived from other genes and/or other organisms). A polynucleotide sequence encoding a signal peptide can also be included to allow a VEGI polypeptide to cross and/or lodge in cell membranes or be secreted from the cell. A number of expression vectors suitable for expression in eukaryotic cells including yeast, avian, and mammalian cells are known in the art.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or polynucleotides will often depend on the host cell.

The invention includes further a host cell and a cell culture comprised of the host cells. This host cell comprising at least one recombinant polynucleotide (generally, DNA) vector was mentioned before. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art. When the host cell is taken from prokaryotic cells it preferably consists of a cell of a bacterium in particular of *Escherichia coli* or *Bacillus* sp. When this host cell consists of a eukaryotic cell it is preferred a cell of a cell line in particular a cell of a COS-, a Hela-, or 3T3-cell-line or a cell of a yeast in particular a cell of *Saccharomyces cerevisiae*.

The host cells of this invention can be used, inter alia, as repositories of VEGI polynucleotides and/or vehicles for production of VEGI polynucleotides and/or polypeptides as described herein. Host cells can also serve as repositories of mutant VEGI-$192a$, VEGI-$192b$, or VEGI-$251$ polynucleotides, as further described herein. Such hosts cells can be useful for screening, production of therapeutic protein or polypeptide as further described herein.

Antibodies and their Preparation

The invention also provides antibodies that selectively bind to VEGI-192a and/or VEGI-192b (including fragments) proteins as described herein. The term "antibody" includes, but not limited to intact molecules, fragments thereof, such as Fab, (Fab')$_2$, Fv, which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; (Fab')$_2$, is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

In some embodiments, the antibodies of the present invention may be any one or more of the following: polyclonal, monoclonal, single chain (ScFv), mutants of these embodiments, fusion proteins comprising an antibody portion (such as one or more CDR regions), humanized antibodies, chimeric antibodies, human antibodies, or any modified configuration of the immunoglobulin molecule that comprises an antigen recognition site of the required specificity.

As is understood in the art, a "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody, which are also termed one or more CDRs "derived from" one or more CDRs from the antibody.

Methods of making antibodies and antibody fragments are known in the art. (See for example, Harlow and Lane, Antibodies: A Laboratory Manual, Cold Spring Harbor Laboratory, New York, 1988, incorporated herein by reference).

The invention also provides an antibody that selectively binds a polypeptide comprising SEQ ID NO:4, SEQ ID NO:5 or a fragment thereof, wherein the fragment is within amino acids 1-26 of SEQ ID NO:4 or SEQ ID NO:5, or the fragment comprises amino acids 26 and 27 of SEQ ID NO:4 or SEQ ID NO:5. The invention also provides antibodies that selectively binds VEGI-$192a$ and VEGI-$192b$ but not other isoforms of VEGI (does not selectively bind to other VEGI isoforms, such as VEGI-$251$). This invention also provides antibodies that selectively binds VEGI-$192a$ or VEGI-$192b$.

The present invention further provides an antibody that selectively binds a polypeptide encoded by SEQ ID NO:1, SEQ ID NO:2, SEQ ID NO:3 or a fragment thereof.

In some embodiments, the invention provides an antibody that selectively binds to a polypeptide comprising a region of at least 5, at least 10, at least 15, at least 20, at least 25, or more contiguous amino acids of SEQ ID NO:4 or SEQ ID NO:5, wherein the region is within amino acid residues 1-26 shown in Table 4 (SEQ ID NO:4) or Table 5 (SEQ ID NO:5). In other embodiments, the invention provides an antibody that selectively binds to a polypeptide comprising a region of at least 5, at least 10, at least 15, at least 20, at least 25, or more contiguous amino acids of SEQ ID NO:4 or SEQ ID NO:5, wherein the region comprises amino acids 26 and 27 of SEQ ID NO:4 or SEQ ID NO:5.

In some embodiments, an antibody of the invention inhibits VEGI activity; for example, such an antibody could promote angiogenesis. Methods of screening such antibody are described below.

In some embodiments, an antibody of the invention can be an agonist antibody in that it promotes VEGI activity. Methods of screening such antibody are described below.

It is understood that, in this context, in which there are various isoforms of VEGI, selective binding indicates binding preferentially (or even exclusively) to a given isoform as compared to another isoform (unless already indicated otherwise). In some embodiments, the antibody selectively binds a VEGI polypeptide of the invention as compared to a non-human VEGI isoform. As an example, an antibody of the invention could selectively bind human VEGI-$192a$ but not mouse (non-human) VEGI-$192a$.

The antibodies of this invention can be linked (i.e., conjugated) to a detectable agent or a hapten. The complex is useful to detect the polypeptide(s) (or polypeptide fragments) to which the antibody specifically binds in a sample, using standard immunochemical techniques such as immunohistochemistry as described by Harlow and Lane (1988), supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of using the monoclonal antibodies of the invention can be done by utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The antibodies of the invention can be bound to many different carriers. Thus, this invention also provides compositions containing antibodies and a carrier. Carriers can be active and/or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, polypeptides of this invention may be detected by the antibodies of the invention when present in samples, such as fluids and tissues. This use of antibodies is discussed in more detail below.

Compositions containing the antibodies, fragments thereof or cell lines which produce the antibodies, are encompassed by this invention. When these compositions are to be used pharmaceutically, they are combined with a pharmaceutically acceptable excipient. Arrays comprising the antibodies or fragments thereof are encompassed by this invention. Antibodies may be immobilized on a surface, e.g., an array for use in detection and diagnostic assays as described in more detail below. Antibodies may also be immobilized on a support for purification of the polypeptides or fragments described herein.

Compositions

The present invention further provides compositions, including pharmaceutical compositions, comprising the polypeptides, polynucleotides, antibodies, recombinant vectors, and host cells of the invention. These compositions may include a buffer, which is selected according to the desired use of the polypeptide, antibody, polynucleotide, recombinant vector, or host cell, and may also include other substances appropriate to the intended use. Those skilled in the art can readily select an appropriate buffer, a wide variety of which are known in the art, suitable for an intended use. In some instances, the composition is a pharmaceutical composition and can comprise a pharmaceutical acceptable excipient, a variety of which are known in the art and need not be discussed in detail herein. Pharmaceutical acceptable excipients have been amply described in a variety of publications, including, for example, A. Gennaro (2000) "Remington: The Science and Practice of Pharmacy", 20th edition, Lippincott, Williams, & Wilkins.

Kits Comprising Polynucleotides, Polypeptides, and/or Antibodies of the Invention As described herein, the present invention also encompasses kits containing polynucleotide(s), polypeptide(s), and/or antibodies of this inventions such as kits for diagnosis, for therapy. Kits embodied by this invention include those that allow someone to conduct an assay for the presence of VEGI polynucleotides, polypeptides, and/or anti-VEGI antibodies, such as any of those describe herein, thus detecting and/or quantitating those molecules. Accordingly, the invention includes (a) a kit for detection or quantification of a VEGI polynucleotide in a sample comprising any of the VEGI polynucleotide described herein; (b) a kit comprising any of the antibodies described herein for detection or quantification of a VEGI polypeptide in a sample; (c) a kit comprising any of the polypeptides described herein for detection or quantification of anti-VEGI antibody in a sample. The invention also provides kits comprising polynucleotides or polypeptides of the invention for use in therapy.

The kits of this invention are in suitable packaging, and may optionally provide additional components that are useful in the procedure. These optional components include, but are not limited to, buffers, capture reagents, developing reagents, labels, reacting surfaces, means for detection, control samples, instructions, and interpretive information.

Methods of Using Polynucleotides, Polypeptides and Antibodies: Detection Systems The invention also provides methods using the VEGI-$192a$ and VEGI-$192b$ polynucleotides, polypeptides, and/or antibodies of the invention to detect suitable targets in a sample. As this disclosure makes clear, detection methods refer to any of detecting presence, absence, as well as quantitation. Procedures for conducting diagnostic (i.e., detection) tests using polynucleotides, polypeptides or antibodies are extensively known in the art and are routine for a practitioner or ordinary skill. Generally, to perform a diagnostic method of this invention, one of the compositions of this invention is provided as a reagent to detect a target with which it reacts in a sample. The target is supplied by obtaining a suitable sample from an individual for whom the diagnostic parameter is to be measured. Many types of samples are suitable for this purpose. If desired, the target may be partially purified from the sample or amplified before the assay is conducted.

The present invention relates to a method of detecting the presence or absence or level of VEGI-$192a$ or VEGI-$192b$ polypeptides in a sample comprising contacting a sample from a human or animal with antibodies which selectively binds to the polypeptide described herein, and detecting the presence or absence or the amount of a complex formed between the polypeptide and the antibodies. Such detecting is useful for the purpose of diagnosis, prognosis, and/or monitoring of an angiogenic-associated disease. In some embodiments, the invention provides a method for the diagnosis of pathological angiogenesis comprising the steps of contacting a sample from a human or animal suspected of having pathological angiogenesis with antibodies which recognize the polypeptide described herein, and detecting the presence or absence of a complex formed between the polypeptide and the antibodies.

A competition assay can be employed wherein antibodies that selectively bind to VEGI-$192a$ and/or VEGI-$192b$ polypeptides are attached to a solid support and labeled VEGI-$192a$ and/or VEGI-$192b$ and a sample derived from the host are passed over the solid support and the amount of label detected, for example, by liquid scintillation chromatography, can be correlated to a quantity of VEGI-$192a$ and/or VEGI-$192b$ in the sample.

A "sandwich" assay is similar to an ELISA assay. In a "sandwich" assay VEGI-$192a$ and/or VEGI-$192b$ is passed over a solid support and binds to antibody attached to a solid support. A second antibody is then bound to the VEGI-$192a$ and/or VEGI-$192b$. A third antibody which is labeled and specific to the second antibody is then passed over the solid support and binds to the second antibody and an amount can then be quantitated.

Using standard methodology well known in the art, a diagnostic assay can be constructed by coating on a surface (i.e., a solid support), for example, a microtitration plate or a membrane (e.g. nitrocellulose membrane), antibodies specific for or which selectively bind to, VEGI-$192a$ or VEGI-$192b$ polypeptides or both, and contacting the coated surface with serum, tissue or other biological or chemical sample obtained from a person suspected of having an angiogenic-associated disease. The presence or absence of a resulting complex formed between VEGI-$192a$ or VEGI-$192b$ polypeptide in the sample and antibodies specific therefor can be detected by any of the known methods common in the art, such as fluorescent antibody spectroscopy or colorimetry. This method of detection can be used, for example, for the diagnosis or prognosis of cancer.

Assaying VEGI-$192a$ and/or VEGI-$192b$ polypeptide levels in a sample can use any antibody-based techniques that are well known in the art. For example, VEGI-$192a$ and/or VEGI-$192b$ polypeptide expression in tissues can be studied with classical immunohistological methods (Jalkanen, M., et al., J. Cell. Biol. 101:976-985 (1985); Jalkanen, M., et al., J. Cell. Biol. 105:3087-3096 (1987)). Other antibody-based methods useful for detecting VEGI-$192a$ and/or VEGI-$192b$ polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying VEGI-$192a$ and/or VEGI-$192b$ polypeptide levels in a sample obtained from an individual, VEGI-$192a$ and/or VEGI-$192b$ polypeptide can also be detected in vivo by imaging. Antibody labels or markers for in vivo imaging of VEGI-$192a$ and/or VEGI-$192b$ polypeptide include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An antibody or antibody fragment that selectively binds to VEGI-$_{192a}$ and/or VEGI-$_{192b}$ polypeptide which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain VEGI-$_{192a}$ and/or VEGI-$_{192b}$ polypeptide. In vivo tumor imaging is described by Burchiel and coworkers (Chapter 13 in Tumor Imaging: The Radiochemical Detection of Cancer, Burchiel, S. W. and Rhodes, B. A., eds., Masson Publishing Inc. (1982)).

As is understood in the art, VEGI-$_{192a}$ and/or VEGI-$_{192b}$ polypeptides may be detected using any agent which selectively binds to the polypeptides.

In another embodiment, the present invention relates to a diagnostic kit comprising antibodies that selectively binds to the polypeptides of the present invention, for example, antibodies that selectively binds VEGI-$_{192a}$ or VEGI-$_{192b}$ or both polypeptides, and ancillary reagents suitable for use in detecting the presence of the polypeptide in a sample. These reagents are well known in the art and that are suitable for use in detecting the presence or absence of VEGI polypeptides in a serum, tissue or other sample. Tissue samples contemplated can be obtained from monkey or human, or other mammals. The kit may further include instructions for use, controls, and interpretative information.

This invention also provides a method for detecting the presence or absence or the level of the polynucleotides described herein comprising contacting a sample from an individual such as a human or an animal with a polynucleotide (in some embodiments, an oligonucleotide) which selectively binds to the polynucleotide described herein, and detecting the presence or absence or the amount of a duplex formed between the polynucleotide used and a polynucleotide in the sample. In some embodiments, the method of the invention, which is useful for the diagnosis of pathological angiogenesis comprising the steps of contacting a sample from a human or animal suspected of having pathological angiogenesis with a polynucleotide (such as an oligonucleotide) which binds to the polynucleotide described herein, and detecting the presence or absence of a duplex formed between the polynucleotide used and a polynucleotide in the sample. In another embodiment, the present invention relates to RNA, DNA or other nucleotide sequences for use in detecting the presence or absence of VEGI polynucleotides using the polymerase chain reaction (PCR) or reverse transcription PCR (RT-PCR). Other primer-based amplification methods may be used. The DNA sequence of the present invention shown in Table 1 (SEQ ID NO:1 or Table 2 (SEQ ID NO:2) can be used to design primers which specifically bind to the VEGI-$_{192a}$ or VEGI-$_{192b}$ polynucleotide sequence in the case of PCR, or to a VEGI-$_{192a}$ or a VEGI-$_{192b}$ cDNA produced from reverse transcription of an RNA encoding a VEGI-$_{192a}$ or VEGI-$_{192b}$ polypeptide, for the purpose of detecting the presence, absence, or quantitating the amount of VEGI-$_{192a}$ or VEGI-$_{192b}$ polynucleotide by comparison to a standard. The primers can be any length ranging, for example, from 7-40 nucleotides, preferably 10-15 nucleotides, most preferably 18-25 nucleotides. Reagents and controls necessary for PCR or RT-PCR reactions are well known in the art. The amplified products can then be analyzed for the presence or absence of VEGI-$_{192a}$ or VEGI-$_{192b}$ polynucleotide sequences, for example by gel fractionation, with or without hybridization, by radiochemistry, and immunochemical techniques. This method is advantageous since only a small sample size is required to generate a sufficient amount of template DNA with which to perform PCR or RT-PCR.

In some embodiments, the detection methods entail using one or more primers to amplify the VEGI-$_{192a}$ and/or VEGI-$_{192b}$ sequence of interest. In other embodiments, detection is accomplished using specific probes (such as labeled probes) which detect presence or absence of (or can quantitate) a VEGI-$_{192a}$ and/or VEGI-$_{192b}$ sequence of interest. In some embodiments, the probe comprises a label.

In some embodiments, the method is used for detecting level of VEGI-$_{192a}$ or VEGI-$_{192b}$ by detecting the presence or absence or the amount of cellular RNA encoding VEGI-$_{192a}$ or VEGI-$_{192b}$ or a fragment described herein. Total cellular RNA can be isolated from a sample using any suitable technique such as the single-step guanidinium-thiocyanate-phenol-chloroform method described by Chomczynski and Sacchi (Anal. Biochem. 162:156-159 (1987)). Levels of mRNA encoding the VEGI-$_{192a}$ and/or VEGI-$_{192b}$ polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

In another embodiment, the present invention relates to a diagnostic kit which contains PCR or RT-PCR primers, one or more primers, such as specific for VEGI-$_{192a}$ or VEGI-$_{192b}$ polynucleotides, and/or primers specific for other isoforms of VEGI, such VEGI-$_{251}$, VEGI-$_{174}$, and ancillary reagents that are well known in the art and that are suitable for use in detecting the presence or absence of VEGI isoform polynucleotides, or quantitating the amount of an RNA which encodes a VEGI isoform polypeptide in a sample using PCR or RT-PCR, or one or more other amplification methods. Samples contemplated can be obtained from humans or animals.

In another embodiment, the present invention relates to a diagnostic kit which contains probes, one or more probes, such as specific for VEGI-$_{192a}$ or VEGI-$_{192b}$ polynucleotides, and/or probes specific for other isoforms of VEGI, such VEGI-$_{251}$, VEGI-$_{174}$, and ancillary reagents that are well known in the art and that are suitable for use in detecting the presence or absence of VEGI isoform polynucleotides, or quantitating the amount of an RNA which encodes a VEGI isoform polypeptide in a sample using methods, such as Northern blotting, or one or more other methods. Samples contemplated can be obtained from humans or animals.

As is understood in the art a "sample" can be any sample obtained from an individual (often referred to as a "biological sample"), body fluid, cell line, tissue culture, or other source which contains or may contain VEGI-$_{192a}$ and/or VEGI-$_{192b}$ polypeptide or mRNA. As indicated, biological samples include body fluids (such as sera, plasma, urine, synovial fluid and spinal fluid) which contain free VEGI-$_{192a}$ and/or VEGI-$_{192b}$ polypeptide, immune and circulatory systems tissue, and other tissue sources found to express complete or mature VEGI-$_{192a}$ and/or VEGI-$_{192b}$ polypeptides or a VEGI-$_{192a}$ and/or VEGI-$_{192b}$ receptor. Methods for obtaining tissue biopsies and body fluids from mammals are well known in the art. Where the biological sample is to include mRNA, a tissue biopsy is the preferred source.

By "assaying the expression level of the gene encoding the VEGI-$_{192a}$ and/or VEGI-$_{192b}$ protein" is intended qualitatively or quantitatively measuring or estimating the level of the VEGI-$_{192a}$ and/or VEGI-$_{192b}$ polypeptide or the level of the mRNA encoding the VEGI-$_{192a}$ and/or VEGI-$_{192b}$ polypeptide in a first sample either directly (e.g., by determining or estimating absolute polypeptide level or mRNA level) or relatively (e.g., by comparing to the VEGI-$_{192a}$ and/or VEGI-$_{192b}$ polypeptide level or mRNA level in a second sample). Preferably, the VEGI-$_{192a}$ and/or VEGI-$_{192b}$ polypeptide level or mRNA level in the first sample is measured or estimated and compared to a standard VEGI-$_{192a}$ and/or VEGI-$_{192b}$ polypeptide level or mRNA level, the standard being taken from a second sample obtained from an individual not having the disorder or being determined by averaging levels from a population of individuals not having a disorder of the immune and circulatory systems. As will be appreciated in the art, once a standard VEGI-$_{192a}$ and/or VEGI-$_{192b}$ polypeptide level or mRNA level is known, it can be used repeatedly as a standard for comparison.

As noted above, VEGI-$_{192a}$ and/or VEGI-$_{192b}$ polynucleotides and polypeptides are useful for diagnosis of conditions involving abnormally high or low expression of VEGI-$_{192a}$ and/or VEGI-$_{192b}$ activities. Given the cells and tissues where VEGI-$_{192a}$ and/or VEGI-$_{192b}$ is expressed as well as the activities modulated by VEGI-$_{192a}$ and/or VEGI-$_{192b}$, it is readily apparent that a substantially altered (increased or decreased) level of expression of VEGI-$_{192a}$ and/or VEGI-$_{192b}$ in an individual compared to the standard or "normal" level produces pathological conditions related to the bodily system(s) in which VEGI-$_{192a}$ and/or VEGI-$_{192b}$ is expressed and/or is active.

The invention also provides methods of aiding diagnosis of a VEGI associated disorder or condition. These methods assist in making a clinical determination regarding the classification, or nature, of pathological angiogenesis or prognosis of cancer, and may or may not be conclusive with respect to the definitive diagnosis. Accordingly, a method of aiding diagnosis of pathological angiogenesis or prognosis of cancer, or a related disease, can comprise the step of detecting the level of VEGI isoforms (i.e. VEGI-$_{192a}$, VEGI-$_{192b}$) expression in a sample from the individual. A method of aiding diagnosis of angiogenesis-associated disease can also comprise the step of detecting altered levels of a VEGI isoform polynucleotide and/or polypeptide in a sample from the individual and/or detecting increased or decreased levels of a VEGI isoform polynucleotide and/or polypeptide in a sample from the individual.

The invention also provides method of detecting an individual at risk who may or may not have detectable angiogenesis associated disease, and/or a condition associated with an abnormal level of VEGI-$_{192a}$ or VEGI-$_{192b}$, and may or may not have displayed detectable disease prior to the treatment methods described therein. "At risk" denotes that an individual who is determined to be more likely to develop a symptom based on conventional risk assessment methods or has one or more risk factors that correlate with development of angiogenesis-associated disease. An individual having one or more of these risk factors has a higher probability of developing angiogenesis-associated disease than an individual without these risk factors. Examples (i.e., categories) of risk groups are well known in the art and discussed herein.

The VEGI-$_{192a}$ and/or VEGI-$_{192b}$ polynucleotide can also be used as probes for the detection of the presence or absence of mutantions or polymorphisms in VEGI-$_{192a}$ and/or VEGI-$_{192b}$ gene, as well as any VEGI-$_{192a}$ or VEGI-$_{192b}$ sequence of interest, whether or not a mutation. A mutant VEGI-$_{192a}$ and/or VEGI-$_{192b}$ may be associated with angiogenesis or various immune and circulatory system-related disorders. Methods for detecting mutant polynucleotide sequences are well known in the art, and include, e.g., single strand conformational polymorphism (SSCP), and various sequence amplification based methods for detecting sequence mutations including point mutations, e.g., LCR, NASBA, PCR, limited primer extension, etc. Methods for detecting altered protein sequences include Western blot analysis, capillary electrophoresis, mass spectroscopy, and WAVE. Generally, a detection experiment will be performed in parallel with a control VEGI-$_{192a}$ and/or VEGI-$_{192b}$ polynucleotide or polypeptide, or, in the case when altered expression levels are being assessed, with a control sample possessing normal levels of a VEGI-$_{192a}$ and/or VEGI-$_{192b}$ polynucleotide or polypeptide.

The sequences of the present invention are valuable for chromosome identification. The sequence is specifically targeted to and can hybridize with a particular location on an individual human chromosome. Moreover, there is a current need for identifying particular sites on the chromosome. The mapping of DNAs to chromosomes according to the present invention is an important first step in correlating those sequences.

Briefly, sequences can be mapped to chromosomes by preparing PCR primers (preferably 15-25 bp) from the cDNA. Computer analysis of the 3' untranslated region of the sequence is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence is mapped to a precise chromosomal location, the physical position of the sequence on the chromosome can be correlated with genetic map data. Such data are found, for example, in V. McKusick, Mendelian Inheritance in Man. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected subject. If a mutation is observed in some or all of the affected individuals but not in any normal subjects, then the mutation is likely to be the causative agent of the disease; a gene localized to a chromosomal region associated with the disease could be one of between 50 and 500 potential causative genes. This assumes 1 megabase mapping resolution and one gene per 20 kb. Utilizing the techniques described above, the chromosomal location of VEGI was determined with very high confidence to be 9q32. Previous chromosomal mapping studies have linked several developmental defects to loci in this area of chromosome 9.

The present invention is also useful for diagnosis or treatment of various immune and circulatory system-related disorders in mammals, preferably humans. Such disorders include infections by bacteria, viruses, and other parasites, immunodeficiencies, inflammatory diseases, lymphadenopathy, autoimmune diseases, graft versus host disease, and any disregulation of immune and circulatory systems cell function including, but not limited to, autoimmunity, leukemias, lymphomas, immunosuppression, immunity, humoral immunity, inflammatory bowel disease, myelo suppression, and the like.

For a number of disorders, substantially altered (increased or decreased) levels of $VEGI\text{-}192_a$ and/or $VEGI\text{-}192_b$ gene expression can be detected in various tissue (such as circulatory tissue) or other cells or bodily fluids (e.g., sera, plasma, urine, synovial fluid or spinal fluid) taken from an individual having such a disorder, relative to a "standard" $VEGI\text{-}192_a$ and/or $VEGI\text{-}192_b$ gene expression level, that is, the $VEGI\text{-}192_a$ and/or $VEGI\text{-}192_b$ expression level from an individual not having the disorder. Thus, the invention provides a diagnostic method useful during diagnosis of a VEGI associated disorder, which involves measuring the expression level of the gene encoding the $VEGI\text{-}192_a$ and/or $VEGI\text{-}192_b$ protein in a sample from an individual and comparing the measured gene expression level with a standard $VEGI\text{-}192_a$ and/or $VEGI\text{-}192_b$ gene expression level, whereby an increase or decrease in the gene expression level compared to the standard is indicative of the disorder.

Thus, the invention provides a diagnostic method useful during diagnosis of a VEGI-associated disorder which involves measuring the expression level of the gene encoding the $VEGI\text{-}192_a$ and/or $VEGI\text{-}192_b$ protein in a sample from an individual and comparing the measured gene expression level with a standard $VEGI\text{-}192_a$ and/or $VEGI\text{-}192_b$ gene expression level, whereby an increase or decrease in the gene expression level compared to the standard is indicative of the disorder.

Where a diagnosis of a disorder has already been made according to conventional methods, the present invention is useful as a prognostic and/or monitoring indicator, whereby patients exhibiting depressed $VEGI\text{-}192_a$ and/or $VEGI\text{-}192_b$ gene expression will experience a worse clinical outcome relative to patients expressing the gene at a level nearer the standard level.

Methods of Using Polynucleotides, Polypeptides and Antibodies: Screening Assays

The polynucleotides and polypeptides of the present invention may be employed as research reagents and materials for discovery of treatments and diagnostics to human disease.

This invention provides a method for identifying agents which modulate an activity of $VEGI\text{-}192_a$ and/or $VEGI\text{-}192_b$; methods for identifying agents which modulate the expression of $VEGI\text{-}192_a$ and/or $VEGI\text{-}192_b$ in a cell. In some embodiments, the assay is a cell-free assay. In other embodiments, the assay is a cell-based assay.

As used herein, the term "modulate" encompasses "increase" and "decrease". In some embodiments, of particular interest are agents, which inhibit an activity $VEGI\text{-}192_a$ and/or $VEGI\text{-}192_b$. Such agents are useful for promoting angiogenesis. In other embodiments, agents of interest are those that increase an activity of $VEGI\text{-}192_a$ and/or $VEGI\text{-}192_b$. Such agents are of interest for inhibiting angiogenesis and treating angiogenesis associated disease.

Generally, the screening or testing methods employ agents or drugs from any variety of sources. An agent or drug may be, for example, a biological or chemical compound such as a simple or complex organic or inorganic molecule, a peptide, a protein, oligonucleotide, polynucleotide, carbohydrate, or lipoprotein. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another.

The invention provides methods for identifying agents that modulates an activity of $VEGI\text{-}192_a$ and/or $VEGI\text{-}192_b$ after binding to $VEGI\text{-}192_a$ and/or $VEGI\text{-}192_b$. The method generally comprises contacting a testing agent that selectively binds to $VEGI\text{-}192_a$ and/or $VEGI\text{-}192_b$ with a sample containing a $VEGI\text{-}192_a$ and/or $VEGI\text{-}192_b$; and assaying an activity of $VEGI\text{-}192_a$ and/or $VEGI\text{-}192_b$ in the presence or absence of the agents. An increase or a decrease in an activity of $VEGI\text{-}192_a$ and/or $VEGI\text{-}192_b$ in the presence of the agent compared to in the absence of the agent indicates that the agent increase (agonist) or decrease (antagonist) the activity of $VEGI\text{-}192_a$ and/or $VEGI\text{-}192_b$. Potential agonists or antagonist include small organic molecules, peptides, polypeptides and antibodies that bind to a polypeptide of the invention and thereby increase or decrease its activity.

Assays for testing the ability of an agent for selectively binding to a polypeptide of the invention is known in the art. For example, the polypeptides of the invention can be attached to a solid support and the agent that selectively binds to the polypeptide can be identified using methods known in the art. Alternatively, $VEGI\text{-}192_a$ and/or $VEGI\text{-}192_b$ agonist and/or antagonists may be detected by combining $VEGI\text{-}192_a$ or $VEGI\text{-}192_b$ and a potential agonist and/or antagonist with membrane-bound $VEGI\text{-}192_a$ or $VEGI\text{-}192_b$ receptors (if such receptors are identified) or recombinant receptors under appropriate conditions for a competitive inhibition assay. $VEGI\text{-}192_a$ or $VEGI\text{-}192_b$ can be labeled, such as by radioactivity, such that the number of $VEGI\text{-}192_a$ or $VEGI\text{-}192_b$ molecules bound to the receptor can determine the effectiveness of the potential agonist and/or antagonist.

Assays for testing activity of VEGI are known in the art. Examples of such cell-based assays are described in the Examples in further detail, such as testing effect on vascular endothelial cell growth, formation and organization of endothelial cells into capillary-like tubular structures, or organization of endothelial cells into capillary vessels in chicken embryo chorioallantoic membrane.

Antibodies that selectively bind to $VEGI\text{-}192_a$ and/or $VEGI\text{-}192_b$ polypeptides may be used as antagonists by binding to $VEGI\text{-}192_a$ and/or $VEGI\text{-}192_b$ and preventing it from performing its activity.

This invention also provides methods for identifying agents that modulates the activity of VEGI isoform described herein without binding to the VEGI isoform. Such agents include, but not limited to, agents that regulate upstream or downstream of activity VEGI. These methods comprise assaying the activity of VEGI in the presence or absence of an agent to be tested.

This invention also provides methods for identifying agents that modulates a level of VEGI mRNA and/or polypeptide described herein.

Accordingly, the present invention provides a method for identifying an agent that modulates a level of VEGI expression in a cell, the method comprising: contacting a candidate agent to be tested with a cell comprising a nucleic acid which encodes a VEGI polypeptide described herein, and determining the effect of said agent on VEGI polypeptide expression. In some embodiments, the effect is measured by detecting the level of mRNA encoding the VEGI polypeptide using the VEGI polynucleotides described herein. In other embodiments, the effect is measured by detecting the level of the VEGI polypeptide using antibodies described herein.

Other potential antagonists include antisense molecules. Antisense technology can be used to control gene expression through antisense DNA or RNA or through triple-helix formation. Antisense techniques are discussed in a number of studies (for example, Okano, J. Neurochem. 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., Nucleic Acids Research 6:3073 (1979); Cooney, et al., Science 241:456 (1988); Dervan, et al., Science $_{251}$:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of VEGI-$_{192a}$ and/or VEGI-$_{192b}$. The antisense RNA oligonucleotide hybridizes to the mRNA in vivo and blocks translation of the mRNA molecule into VEGI-$_{192a}$ and/or VEGI-$_{192b}$ polypeptide. The oligonucleotides described above can also be delivered to cells such that the antisense RNA or DNA may be expressed in vivo to inhibit production of VEGI-$_{192a}$ and/or VEGI-$_{192b}$ polypeptide.

This invention also provides methods for identifying agents such as mutants or variants of VEGI-$_{192a}$ and/or VEGI-$_{192b}$ which may compete for binding with the targets which VEGI-$_{192a}$ and/or VEGI-$_{192b}$ bind to and prevents VEGI-$_{192a}$ and/or VEGI-$_{192b}$ from interacting with their targets. Such mutants or variants may be agonist or antagonist of VEGI-$_{192a}$ and/or VEGI-$_{192b}$.

This invention provides a method for identifying agents that bind to VEGI-$_{192a}$ and/or VEGI-$_{192b}$ comprising contacting the agents with VEGI-$_{192a}$ and/or VEGI-$_{192b}$ and then detecting agents' binding to VEGI-$_{192a}$ and/or VEGI-$_{192b}$.

Methods of Using Polynucleotides, Polypeptides and Antibodies: Treating Disease

The invention provides methods for inhibiting vascular endothelial cell growth, inhibiting angiogenesis, for the treatment or amelioration of diseases and processes that are mediated by uncontrolled angiogenesis, treating cancer, such as suppressing tumor growth. Contrary to the teachings that VEGI-$_{251}$ is a membrane bound protein, the Examples show that VEGI-$_{251}$ is a secreted protein, inhibits vascular endothelial cell growth, and has anti-angiogenesis effect upon expression. In addition, the Example also shows that VEGI-$_{192a}$ inhibits vascular endothelial cell growth.

Accordingly, the compositions that can be used for the method of the invention include, but not limited to, polynucleotides described herein, such as polynucleotides encoding polypeptides of SEQ ID NO:4, SEQ ID NO:5, or SEQ ID NO:6; polypeptides described herein, such as polypeptides of SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6; and agonist or antagonist of VEGI polypeptides described herein, such as an antibody that blocks the activity of VEGI polypeptide.

The invention also includes methods of delaying development of an angiogenesis-associated disease in an individual.

VEGI isoform polypeptides of the present invention (and polynucleotides encoding VEGI isoform polypeptides) can be used to reduce the formation of capillary-like tubular structures formed by endothelial cells in vitro. VEGI isoform polypeptides of the present invention can be used to inhibit the formation of endothelial cells organized into capillary-like tubular structures in response to angiogenic factors such as FGF-2. Furthermore, isolated VEGI isoform polypeptides described herein of the present invention can also be used to inhibit the growth and organization of endothelial cells into capillary vessels in a modified chicken embryo chorioallantoic membrane (CAM). As a result, VEGI isoform polypeptides of the present invention can be used to inhibit the formation of capillaries or capillary-like structures from endothelial cells in vitro.

It will be appreciated that conditions caused by a decrease in the standard or normal level of VEGI isoform polypeptides activities in an individual, particularly disorders of the immune and circulatory systems, can be treated by administration of VEGI isoform polypeptides described herein (or polynucleotides encoding the VEGI isoform polypeptides). Thus, the invention also provides a method of treatment of an individual in need of an increased level of a VEGI isoform activity comprising administering to such an individual a pharmaceutical composition comprising an amount of an isolated VEGI isoform polypeptide of the invention (or a polynucleotide), such as a mature form of the VEGI isoform polypeptide of the invention, effective to increase the VEGI isoform polypeptide activity level in such an individual. The invention also provides a method of treatment of an individual in need of a decreased level of a VEGI isoform activity comprising administering to such an individual a pharmaceutical composition comprising an amount of antagonist of the VEGI isoform, such as an antibody specific for the VEGI isoform that blocks the activity of the VEGI isoform, effective to decrease the VEGI isoform polypeptide activity level in such an individual.

Polynucleotide-based Delivery

In some embodiments, the invention includes a method of inhibiting angiogenesis in a tissue or cell comprising causing an effective amount of a polypeptide having an amino acid sequence of SEQ ID NO:4 or SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6 to come into contact with, or be expressed in the proximity of, the tissue or the cell, such that angiogenesis is inhibited. In some embodiments, the invention includes a method of inhibiting angiogenesis comprising administering to an individual, such as a human or animal, a composition comprising the nucleic acid molecule encoding polypeptide of SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to inhibit angiogenesis. In some embodiments, the nucleic acid molecule is operably associated with a regulatory sequence that controls gene expression. Such regulatory sequences are known in the art.

As an individual is an animal, in some embodiments, an individual may be a mammal.

The invention also provides a method for the treatment or amelioration of disease and processes that are mediated by uncontrolled angiogenesis, comprising the step of administering to an individual, such as a human or animal, a composition comprising a nucleic acid molecule encoding SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to control angiogenesis. In some embodiments, the nucleic acid molecule is operably associated with a regulatory sequence that controls gene expression.

This invention also provides a method for treating cancer or suppressing tumor growth comprising the step of administering to an individual, such as a human or animal, a composition comprising the nucleic acid molecule encoding SEQ ID NO:4, or a SEQ ID NO:5, or a SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to suppress tumor growth. In some embodiments, the nucleic acid molecule is operably associated with a regulatory sequence that controls gene expression.

It is understood, if a truncated form of VEGI is used and the truncation occurs at the secretory signal sequence, the truncated form includes a secretory signal sequence, either homologous or heterologous, for directing secretion of the protein. Heterologous secretory signal sequences are known in the art.

Methods of delivering polynucleotides for expression in an individual (both ex vivo and in vivo) are known in the art. Generally, an appropriate polynucleotide vector construct is prepared and administered.

Targeted delivery of therapeutic compositions containing polynucleotides, expression vector, or subgenomic polynucleotides can be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338. Therapeutic compositions containing a polynucleotide may be administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP 0 345 242), alphavirus-based vectors (e.g., Sindbis virus vectors, Semliki forest virus (ATCC VR-67; ATCC VR-1247; Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581.

Thus, for example, cells from a patient may be engineered with a polynucleotide (DNA or RNA) encoding a polypeptide, such as VEGI-$_{251}$, ex vivo, with the engineered cells then being provided to a patient to be treated with the polypeptide. Such methods are well-known in the art and are apparent from the teachings herein. For example, cells may be engineered by the use of a viral or a retroviral particle containing DNA or RNA encoding a polypeptide of the present invention.

Similarly, cells may be engineered in vivo for expression of a polypeptide in vivo by, for example, procedures known in the art. For example, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector generally includes one or more promoters. Suitable promoters which may be employed include, but are not limited to, the retroviral LTR; the SV40 promoter; and the human cytomegalovirus (CMV) promoter described by Miller and colleagues (Biotechniques 7:980-990 (1989)), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

If a retroviral vector system is chosen, the retroviral plasmid vector is employed to transduce packaging cell lines to form producer cell lines. Examples of packaging cells which may be transfected include, but are not limited to, the PE501, PA317, b-2, b-AM, PA12, T19-14X, VT-19-17-H2, CRE, .beta.-CRIP, GP+E-86, GP+envAm12, and DAN cell lines as described by Miller (Human Gene Therapy 1:5-14 (1990)), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

These general principles apply to other viral based delivery systems, such as AAV.

Polypeptide Delivery

The invention also provides a method of inhibiting angiogenesis comprising administering to an individual, such a human or animal a polypeptide described herein, such as the polypeptide of SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to inhibit angiogenesis.

The invention also provides a method for the treatment or amelioration of disease and processes that are mediated by uncontrolled angiogenesis, comprising the step of administering to an individual, such as a human or animal, a composition comprising the polypeptide of SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to control angiogenesis.

This invention also provides a method for treating cancer or suppressing tumor growth comprising the step of administering to an individual, such as a human or animal, a composition comprising the polypeptide of SEQ ID NO:4, SEQ ID NO:5, or SEQ ID NO:6, or a truncated form which comprises at least one or more amino acids from the region of amino acids 1-26 of SEQ ID NO:4, amino acids 1-26 of SEQ ID NO:5, or amino acids 1-85 of SEQ ID NO:6, in a dosage sufficient to suppress tumor growth.

Methods for testing the activity of a VEGI polypeptide (including a truncated form of VEGI) is well known in the art and are described in the Examples in detail, such as assay for testing effect on vascular endothelial cell growth, capillary-like tube formation, capillary growth in collagen gels placed on chick embryo chorioallantoic membrane, xenograft tumor growth.

As used herein, "angiogenesis associated disease" a disease or condition that is associated with undesired and/or unregulated angiogenesis, or a disease or condition for which it is advantageous to inhibit angiogenesis. It includes disease or processes mediated by undesired and/or uncontrolled angiogenesis. Examples of such angiogenesis associated diseases, such as tumor growth, are described herein.

VEGI isoform polypeptides described herein may be used to inhibit the proliferation of endothelial cells, for example, aortic endothelial cells. As a result, VEGI-$_{192a}$, VEGI-$_{192b}$ and/or VEGI-152 polypeptide can be used to treat diseases and disorders in which inhibition of endothelial cell growth is advantageous.

The VEGI isoform polypeptide composition will be formulated and dosed in a fashion consistent with good medical practice, taking into account the clinical condition of the individual patient (especially the side effects of treatment with VEGI isoform polypeptides alone), the site of delivery of the VEGI isoform polypeptide composition, the method of administration, the scheduling of administration, and other factors known to practitioners. The "effective amount" of VEGI isoform polypeptide for purposes herein is thus determined by such considerations.

The VEGI isoform polypeptides and agonists and antagonists of the present invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 g/kg body weight and in most cases they will be administered in an amount not in excess of about 8 mg/Kg body weight per day. In most cases, the dosage is from about 10 g/kg to about 1 mg/kg body weight daily, taking into account the routes of administration, symptoms, etc.

Various delivery systems are known and can be used to administer VEGI isoform polypeptides of the present invention, e.g., encapsulation in liposomes, microparticles, microcapsules, receptor-mediated endocytosis (see, e.g., Wu and Wu 1987, J. Biol. Chem. 262:4429-4432). Methods of introduction include, but are not limited to, topical, intradermal, intramuscular, intraperitoneal, intravenous, subcutaneous, intranasal, epidural, ophthalmic, and oral routes. The compounds may be administered by any convenient route, for example, by infusion or bolus injection, by absorption through epithelial or mucocutaneous linings (e.g., oral mucosa, rectal and intestinal mucosa, etc.) and may be administered together with other biologically active agents.

In a specific embodiment, it may be desirable to administer the pharmaceutical compositions of the invention locally to the area in need of treatment. This may be achieved by, for example, and not in limitation of, local infusion during surgery, topical application, e.g., in conduction with a wound dressing, by injection, by means of a catheter, by means of a suppository, or by means of an implant, said implant being of a porous, non-porous, or gelatinous material, including membranes, such as sialastic membranes or fibers.

Assessment of disease is performed using standard methods in the art, such as imaging methods and monitoring appropriate markers.

It will also be appreciated by one of ordinary skill that, since the VEGI isoform polypeptides of the invention are members of the TNF family the mature secreted form of the protein may be released in soluble form from the cells which express VEGI isoform polypeptides described herein by proteolytic cleavage. Therefore, when the mature form or soluble extracellular domain of VEGI isoform polypeptides is added from an exogenous source to cells, tissues or the body of an individual, the polypeptide will exert its physiological activities on its target cells of that individual. Also, cells expressing this type II transmembrane polypeptide may be added to cells, tissues or the body of an individual and these added cells will bind to cells expressing receptor for VEGI isoform polypeptides described herein, whereby the cells expressing VEGI isoform polypeptides can cause actions (e.g. regulation of endothelial cell growth and regulation) on the receptor-bearing target cells.

As stated above, VEGI is shown to have strong anti-proliferation effects on endothelial cell growth. Accordingly, VEGI may also be employed to regulate the development of endothelial cells from hematopietic and circulating endothelial precursor cells.

Accordingly, the invention provides methods of enhancing angiogenesis comprising administering an inhibitor of VEGI-$192a$ or VEGI-$192b$, such that angiogenesis is enhanced. Such enhancement may be desirable, for example, in the context of conditions associate with an obstruction of a blood vessel, such as ischemic conditions or heart attack. The formulations may be administered locally or systemically using methods known in the art.

The antibody of the present invention that blocks or suppress the activity the VEGI polypeptide may be used for promoting or enhancing angiogenesis.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

The present invention will be further described with reference to the following examples, however, it is to be understood that the present invention is not limited to such examples.

The discovery of an endothelial cell-specific gene product, vascular endothelial cell growth inhibitor (VEGI) has recently been reported (Zhai Y, et al., *FASEB J.*, 13: 181-189, 1999; Zhai, Y, et al., *Int. J. Cancer,* 82:131-136, 1999). The protein consists of 174-amino acids, i.e., VEGI-$174$, with a 20-30% sequence homology to members of the TNF superfamily. Northern blotting analysis of a wide variety of cell lines and primary cell cultures indicates that the VEGI-$174$ gene is expressed predominantly in endothelial cells. Additionally, the VEGI-$174$ mRNA is detectable in many adult human organs, suggesting a physiological role of the gene in a normal vasculature. The function of VEGI-$174$ was examined in a number of cellular and animal models. Recombinant truncated form of VEGI-$174$ inhibited endothelial cell proliferation with a remarkable potency, but had no effect on the growth of any other types of cells examined. The truncated form of the protein also inhibited the formation of capillary-like structures by endothelial cells in collagen gels, and the growth of capillaries into collagen gels placed on the chick chorioallantoic membrane. Overexpression of a secreted form of VEGI-$174$ in murine colon cancer cells (MC-38) nearly completely prevented these cells from growing tumors in syngenic C57/BL mice. Moreover, co-inoculation of human breast cancer cells with Chinese hamster ovary cells overexpressing secreted form of VEGI-$174$ led to marked inhibition of the growth of the breast cancer xenograft tumors in nude mice.

Example 1

ELISA Analysis of Human Sera

Normal human sera of normal male and female adult individuals are obtained from the Lombardi Cancer Center serum bank. Sandwich ELISA was used to measure serum VEGI content. Serum samples (100 µl) or varying amounts of recombinant VEGI protein in 3% BSA were added to 96-well plates coated with a polyclonal anti-VEGI antibody and blocked with 3% BSA. A monoclonal antibody (100 µl, 2 µg/ml) against VEGI (3-12D) was added. Biotinylated anti-mouse IgG antibody (2 µg/ml, Vector laboratories, Burlingame, Calif.) was added, followed by avidin-horseradish peroxidase, with 3,3',5,5'-tetramethylbenzidine (Vector laboratories) as substrate. The samples were incubated at room temperature for 10 min, the reaction terminated with 50 µl 1M $H_2SO_4$, then analyzed at 450 nm with a spectrophotometric plate reader, using the standard curve y=−0.72+ 0.409*log(x). Standard protein range used was 0.32-1000 ng/ml.

Example 2

Northern Blotting

Multi-tissue Northern blots and multi-tissue dot-blot panels (Clontech, Palo Alto, Calif.) were hybridised in ExpressHyb solution (Clontech) with double-stranded cDNA probes. The full length VEGI-$_{174}$ probe used was a Hind III-BamHI cDNA fragment (GenBank Accession #AF03990) in pCDNA3.1 (Invtrogen, Carlsbad, Calif.). For isoform-specific probes, a 297-bp VEGI-$_{251}$ template encoding its N-terminal 99 amino acids was made by PCR amplification, and labeled wth $^{32}$P-dCTP by random priming (Life Technologies, Invitrogen, CA). The VEGI-$_{174}$ specific probe corresponding to its N-terminal 22 amino acids was made by end-labeling a 66-bp PCR product. The blots were hybridized at 42° C. overnight and washed in wash buffer 1 (2×SSC, 0.1% Sodium lauryl sulfate) and wash buffer 2 (1×SSC, 1% SDS) at 42° C. followed by autoradiography at −70° C. with an intensifying screen.

Example 3

5'RACE and VEGI Isoform Cloning

5' VEGI sequences were amplified from a multi-tissue RACE panel (ORIgene, Rockville, Md.) according to the manufacturer's instructions. This panel contains cDNA samples prepared from 24 individual human tissues, with an adapter ligated to the 5' ends of the cDNAs. Two rounds of nested PCR were performed using two pairs of oligonucleotide primers. In the first round of PCR, an adapter primer ADP1, 5' CGGAATTCGT CACTCAGCG 3' (SEQ ID NO:8) and a VEGI gene-specific primer GSP1, 5' CCCGGATCCT ATAGTAAGAA GGCTCC 3' (SEQ ID NO:9) were used. The reaction products were then diluted 1:10 with water. The diluted PCR samples were then used for the second round of PCR with another adapter primer, ADP2, 5' AGCGCGTGAA TCAGATCG3' (SEQ ID NO:10), and a VEGI gene-specific primer, GSP2, 5' CGGTGGATCC CGAGTTTGTC TCACAACTG3' (SEQ ID NO:11). The PCR products were resolved on an agarose gel, purified, and sequenced on an ABI automatic sequencer.

Example 4

Isolation of VEGI$_{251}$ and VEGI-$_{192a}$

Gene-specific primers designed according to sequencing results of the RACE products were used to repeat the second round PCR to confirm their sequence identities. The gel-purified RACE products were then cloned into plasmid pCR3.1 (Invitrogen, Frederick, Md.) and sequenced. Based on these sequences, isoform-specific primers were designed. The shared reverse primer, Vg161 (161), 5'GTGTAATCCA CCAAAGAG3' (SEQ ID NO:12) was used with forward primers listed in Table 8.

TABLE 8

5' Sequence of human VEGI isoforms (SEQ ID NOS:13, 14, 15)

| Isoform | Source | A. Nucleotide sequence | |
|---|---|---|---|
| VEGI-$_{174}$ | Brain | CAAAGTAATT TGCCCCAGGT CACTAGTCCA AGATGTTATT CTCTTTGAAC AAATGTGTAT GTCCAGTCAC ATATTCTTCA TTCATTCCTC CCCAAAGCAG TTTTTAGCTG TTAGGTATAT TCGATCACTT TAGTCTATTT TGAAAATGAT ATGAGACACT TTTTAAGCAA <u>AGTCTACAGT TTCCCAATGA</u> GAAAATTAAT CCTCCTCCTC TCTCGGGAAC | (SEQ ID NO:13) |
| VEGI-$_{251}$ | Uterus | GGGGGGGGGG GTCAGAGGTG CCTGGTGTTG CTCCCCTTCC TTGCAGG<u>ACT CACCACATAC CTGCTTGTCA</u> GCCAGCTCCG GGCCCAGGGA GAGGCCTGTG TGCAGTTCCA GGCTCTAAAA GGACAGGAGT TTGCACCTTC ACATCAGCAA GTTTATGCAC CTCTTAGAGC AGACGGAGAT AAGCCAAGGG CACACCTG | (SEQ ID NO:14) |
| VEGI-$_{192a}$ | Lung | CTCCTATCAT AGGCGCCATG CAACTCACAA AGGGCC<u>GTCT TCATTTCAGT CACCCTTTGT</u> CTCATACAAA GCACATTTCT CCTTTTGTTA CAGATGCACC TCTTAGAGCA GACGGAGATA AGCCAAGGGC ACACCTG | (SEQ ID NO:15) |

*Table showing the unique 5' cDNA sequences of the isolated VEGI isoforms. Forward PCR primers used to screen cDNA libraries to isolate full length clones are underlined. The sequence of the shared reverse PCR primer is given in the Methods.

Example 5

Cell Culture and TNFα Treatment

Human umbilical vein endothelial cells (HUVE), and fetal bovine heart endothelial (FBHE) cells were obtained from Clonetics (Walkersville, Md.) and grown in EGM-2 (Clonetics). Human dermal microvascular endothelial (HMVE), human coronary artery endothelial (HCAE) cells and NIH3T3 cells were obtained from the American Type Culture Collection and grown in EGM2-MV (Clonetics). Adult bovine aortic endothelial (ABAE) cells, and mouse brain endothelioma bEND.3 were gifts from Dr Peter Bohlen of ImClone Inc, New York, N.Y. Human coronary artery smooth muscle cells (HCASM) (Clonetics) and ABAE cells were cultured in IMEM (Biofluids, Biosource International, Camarillo, Calif.), 10% FBS, 1 ng/ml fibroblast growth factor-2 (Promega, Madison, Wis.). EA.Hy926, a human endothelial-derived cell line, was a gift from Dr Cora-Jean Edgell, University of North Carolina. These cells, together with mouse brain bEND.3 and heart H5V endothelioma cell lines, were maintained in IMEM with 10% FBS. Subconfluent cells grown in 100-mm dishes were treated with various doses of tumor necrosis factor α (TNFα) (Biosource International, Camarillo, Calif.) prior to RNA analysis.

Example 6

Ribonuclease Protection Assays

For isoform-specific probes, cDNA fragments from human VEGI-$_{174}$ (862-1062 bp), VEGI-$_{251}$ (1-160 bp), VEGI-$_{192a}$ (277-656 bp), were generated by PCR and inserted between the EcoRI and NotI sites of pcDNA3 (Invitrogen) in the antisense direction. A mouse β-actin probe (824-942) was cloned into pSP72 (Promega) between the HindIII and BamHI sites. The VEGI and β-actin templates were linearized with HindIII and EcoRI, respectively. Antisense run-off probes were synthesized with SP6 RNA polymerase using the Maxiscript transcription kit (Ambion, Woodward Tex.). For nuclease protection with the RPAIII kit (Ambion, Tex.), 15-20 μg of total RNA was hybridised overnight with 1-3×10$^5$ cpm of each probe at 52° C. RNase digestion was performed with 1:100 dilution of RNase A/T1 mix (Ambion) for 30 min at 37° C. The products of digestion were precipitated, resolved on a 6% polyacrylamide gel, and subjected to autoradiography at −70° C.

Example 7

Gene Structure Analysis

The organization of the human VEGI gene was analyzed by PCR using a bacterial artificial chromosome (BAC) clone (Genome Systems, Inc, St Louis, Mo.). PCR primers from exonic sequences were designed which generated overlapping PCR products. These PCR products were sequenced to determine their relative positions. Primers for the intronic region were designed based the GenBank entry for Chromsome 9 Contig NT_017568, which correspond to sequences between bases 2,643,881 and 2,694,724. These are listed in Table 9. With human placenta DNA as a template, extra long PCR was performed using an rTth XL PCR kit from Perkin Elmer (Foster City, Calif.) and the following extra long PCR conditions: 95° C., 1 min, 97° C., 15 sec, 60.5° C., 10 min, 17 cycles; 97° C., 15 sec, 60.5° C., 10 min plus 15 sec extension, 13 cycles, followed by final extension at 72° C. for 11 min. The PCR fragments were generated with the primer pairs shown in Table 9. The PCR products were sequenced.

TABLE 9

PCR primers used in mapping of the human VEGI gene*
(SEQ ID NOS:16-33)

| PCR product | Forward primer | |
|---|---|---|
| 1 | ATGGCCGAGG ATCTGGGACT | (SEQ ID NO:16) |
| 2a | 50:CCTTGCAGGA CTCACCACAT ACCTGCTT | (SEQ ID NO:18) |
| 2b | 61:TGGGGATAAC CTTCAGCCTC ATATTTTTA | (SEQ ID NO:20) |
| 2c | 60:AGAGGCTAGG TTTCCAGTTA AACCCATTGA | (SEQ ID NO:19) |
| 2d | 57:GATCTGGAGG GACTGATGGA GAAGAAATGG | (SEQ ID NO:22) |
| 2e | 51:TACGTGCCCA GTAGTGAGAT TGCTAGAC | (SEQ ID NO:23) |
| 2f | 53:GAGGCTGATG AAAAGGAGAA CATAGCCATT ATT | (SEQ ID NO:24) |
| 3 | CTAAAAGGAC AGGAGTTTGCA | (SEQ ID NO:25) |
| 4 | ATTTCTCCTT TTGTTACAG | (SEQ ID NO:27) |
| 5 | ATCTAGTTCA TCTGTGCCTGTTCA | (SEQ ID NO:29) |
| 6 | CCAGTTGTGA GACAAACTCCC | (SEQ ID NO:31) |

| PCR product | Reverse primer | |
|---|---|---|
| 1 | CTGCACACAG GCCTCTCCCTG | (SEQ ID NO:17) |
| 2a | 60:AGAGGCTAGG TTTCCAGTTA AACCCATTGA | (SEQ ID NO:19) |
| 2b | 52:ATGTGAAGGT GCAAACTCCT GTCCTTTTAG | (SEQ ID NO:21) |
| 2c | 61:TGGGGATAAC CTTCAGCCTC ATATTTTTA | (SEQ ID NO:20) |
| 2d | 52:ATGTGAAGGT GCAAACTCCT GTCCTTTTAG | (SEQ ID NO:21) |
| 2e | 52:ATGTGAAGGT GCAAACTCCT GTCCTTTTAG | (SEQ ID NO:21) |
| 2f | 52:ATGTGAAGGTGCAAACTCCTGTCCTTTTAG | (SEQ ID NO:21) |
| 3 | CTGTAACAAA AGGAGAAAT | (SEQ ID NO:26) |
| 4 | CTTGAACAGG CACAGATGAAC | (SEQ ID NO:28) |
| 5 | GGGAGTTTGT CTCACAACTGG | (SEQ ID NO:30) |
| 6 | GTAAGGCACA TGAAGTGTGAAAT | (SEQ ID NO:32) |

*Nucleotide sequence of oligonucleotide primers used in PCR analysis of the human VEGI gene. PCR product 2b was also sequenced using primers 61, 57, 51, and 53.

Example 8

Expression Plasmids and Transient Transfections

The open reading frames of VEGI-$_{174}$ and VEGI-$_{251}$ were inserted into pcDNA3.1-myc (Invitrogen, MD) to generate peptides bearing a C-terminal myc tag. The resultant plasmids were transfected into ABAE and HUVE cells for cellular localization studies. For cell transfections, 3×10$^4$ cells were seeded on Lab-Tek chambered coverglass (Nalge, Naperville, Ill.) overnight. Plasmid DNA (400 ng) in 25 μl serum-free IMEM was mixed with PLUS reagent (4 μl) (GIBCO-BRL). LipofectAMINE (GIBCO) reagent (1 μl) was 200-fold and mixed with the DNA solution for 15 mins. The DNA-lipofectAMINE complex was then added to cells with 200 μl IMEM and incubated at 37° C. for 3 h. The cells were allowed to recover in serum-containing growth medium for 36 h prior to immuno-staining and subsequent fluorescence microscopy. The full length coding region of VEGI-$_{174}$ or VEGI-$_{251}$ was also inserted between the EcoR1 and BamH1 sites of pEGFP-C2 (Clontech) to make GFP-VEGI fusion proteins. The GFP-VEGI fusion constructs were transfected into ABAE cells as described above. At 48 h post-transfection, the cellular localization of the fusion protein were examined by fluorescence microscopy.

Example 9

Immunostaining for Subcellular Localization

Transfected adult bovine aortic (ABAE) and HUVE cells were washed with PBS and fixed with 3.7% paraformaldehyde/0.1% Triton X-100 in PBS for 10 min, permeabilized with 0.5% Triton X-100 in PBS for 5 mins, then incubated with a 1:300 dilution of an anti-myc monoclonal antibody 9-10E (Sigma) for 1 h. The cells were washed with PBS and incubated with anti-mouse IgG, Texas Red-conjugated monoclonal antibody at a 1:60 dilution (Jackson ImmunoResearch Labs, Inc West Grove, Pa.), then washed thrice with PBS. The cells were visualized by confocal fluorescence microscopy (Olympus IX70-SIF).

Example 10

Production of Monoclonal Antibodies

Six-week-old female BALB/c mice (Charles River Laboratories, Wilmington, Mass.) were injected subcutaneously with purified recombinant VEGI protein (residues 29-$_{174}$) at 50 µg per mouse in 0.1 ml of a complete Freud's adjuvant (Life Technologies). Following intraperitoneal boosters, mice with higher titers received a final intraperitoneal antigen injection of 30 µg/mouse. Spleen cells were isolated and fused with mouse myeloma SP2/O cells, using polyethylene glycol 1500 (Boehringer Mannheim). Hybridomas were selected by HAT medium and screened by ELISA. Positive hybridomas were cloned and the subclass of monoclonal antibodies was determined using the mouse isotype kit (SIGMA, MO). Hybridomas were cultured on an INTEGRA CL 350 (INTEGRA Biosciences, Inc., Iiamsville, Md.), the supernatants collected, and monoclonal antibodies were purified by AffiGel protein A agarose (Bio-Rad).

Example 11

Production of Polyclonal Antibodies

Four to six-month-old SPF New Zealand White rabbits (Charles River) were inoculated subcutaneously with 100 µg of E. coli expressed recombinant VEGI (as above) mixed with complete Freud's adjuvant (Life Technologies). Following intramuscular boosters, serum was collected from rabbits showing substantial immune response. Sera was purified by absorption with E. coli (transformed with an empty expression vector) cell lysate, then with human coronary artery smooth muscle cell lysate.

Example 12

Analysis of VEGI in Mammalian Cells and Conditioned Media

The full-length VEGI-$_{251}$ coding region was inserted between the Hind III and BamHI sites of pcDNA3 (Invitrogen). These pcDNA3 plasmids, including vector, were transfected into MDA-MB231 breast cancer cells by electroporation. Stable transfectants were selected in 2 mg/ml G418 sulfate (GIBCO). Conditioned media were concentrated with Centricon columns (MW cutoff 10,000). Both cell lysates and conditioned media were immunoprecipitated with protein A/G agarose (Oncogene, Boston, Mass.) and the polyclonal antibody against VEGI. The samples were analyzed by Western blotting. Detection was effected with a 1:1000 dilution of mouse monoclonal antibodies 1-8F, and visualized with anti-mouse IgG antibody conjugated with horseradish peroxidase (ECL kit, Amersham).

Example 13

Lentiviral Gene Transfer

The lentiviral vectors containing VEGI-$_{174}$, sVEGI and VEGI-$_{251}$ were prepared using previously described methods (Dull, et al. *J Virol* 72, 8463-8471, 1998; Naldini, et al. *Proc Natl Acad Sci* (*USA*) 93, 11382-11388, 1996; Naldini, et al. *Science* 272, 263-267, 1996; Stewart, et al. *Proc Natl Acad Sci* (*USA*) 96, 12039-12043. 1999). Briefly, the lentiviral vector was generated in 293T cells with 3 plasmids: the transducing plasmid pHR'CMV-VEGI, the packaging plasmid pCMV ΔR8.2 Δvpr and the envelope plasmid pCMV-VSV-G. Viral supernatants were collected every 24 h from two days post-transfection, purified by 0.45 µm filtration and titrated by p24 assay (Dull, et al. *J Virol* 72, 8463-8471, 1998; Naldini, et al. *Proc Natl Acad Sci* (*USA*) 93, 11382-11388, 1996; Naldini, et al. *Science* 272, 263-267, 1996; Stewart, et al. *Proc Natl Acad Sci* (*USA*) 96, 12039-12043. 1999). One pg of p24 count was defined as one tissue culture infective dose (TCID). For cell toxicity assays, HUVE cells were plated at a density of $2 \times 10^4$ per well in a 24-well plate 20 h before infection with viral supernatant. The cell number was expected to double 20 h after plating. Increasing doses of viral vector were added to HUVE cells. The multiplicity of infection (MOI) was estimated as TCID per cell at the time of infection. The number of adherent cells remaining in culture 24 h after viral infection were determined by Coulter Counter.

Example 14

In Vivo Tumorigenicity Assay

Stably transfected MDA-MB-231 cells containing empty pcDNA3 vector, VEGI-$_{174}$, VEGI-$_{251}$ or sVEGI were injected into mammary fat pads of female athymic nude mice ($1 \times 10^6$ cells/injection). There were 2 injection sites per animal and 15 animals in each group which received the VEGI-$_{174}$, VEGI-$_{251}$ and sVEGI transfectants. A group of 5 animals injected with pcDNA3 vector transfectants was used as control. The sizes of the resultant xenograft tumors monitored in a blinded manner. Determination of microvessel density was carried out as described (Weidner, et al. *N Engl J Med* 324, 1-8, 1991). Briefly, intratumor microvessels were immunostained with rat anti-mouse CD31 (PECAM-1) monoclonal antibody (clone MEC13.3, Pharmingen International, San Diego, Calif.). The antibody was diluted 1:100 in PBS, incubated overnight with 5 µm paraffin-fixed tumor sections, and visualized with a biotinylated anti-rat IgG antibody (Vector Laboratories) by the Vectastain ABC method (Vector Laboratories). Each sample was examined under low power (×10 objective lens and ×10 ocular lens) to identify the most vascular areas of the tumor ("hot spots", see reference (Weidner, et al *N Engl J Med* 324, 1-8, 1991)). Within these areas, a maximum of 10 fields at ×400 magnification (×40 objective and ×10 ocular lens; 0.16 mm² per field) were examined, and the mean values calculated. Large vessels with muscular walls were excluded. The lumen was not required to identify a vessel. Any positively stained endothelial cells or cell clusters, clearly separate from adjacent microvessel, tumor cells and connective tissue elements, were regarded as distinct countable microvessels. All measurements were performed in a blinded manner. The results were analyzed by one-way analysis of variance (ANOVA). The a priori level of significance was set at P-value of less than 0.05.

Example 15

Detection of VEGI Protein in Human Sera

As an initial screen to determine whether VEGI exists in a soluble form, we analyzed a human serum bank of healthy adults with monoclonal antibodies. We were able to detect, by ELISA with an antibody against the C-terminus, VEGI concentrations ranging between 1 and 10 ng/ml (FIG. 1). This indicated that, in addition to the previously characterized VEGI which was believed to be membrane-bound, a soluble form of VEGI would also be of significant physiological relevance. Since previous studies had shown apoptotic activity of a recombinant C-terminal peptide, and overexpression of the full length VEGI-$_{174}$ was ineffective on xenograft tumors formed by transfected cancer cells, we thus reasoned that the C-terminus-containing soluble peptide found in human sera was not likely to have been derived from VEGI-$_{174}$. This observation then prompted us to propose that the VEGI gene might express alternate forms in human tissue.

Example 16

Detection of Multiple VEGI Transcripts and Cloning of Novel VEGI Isoforms

Figure 2:
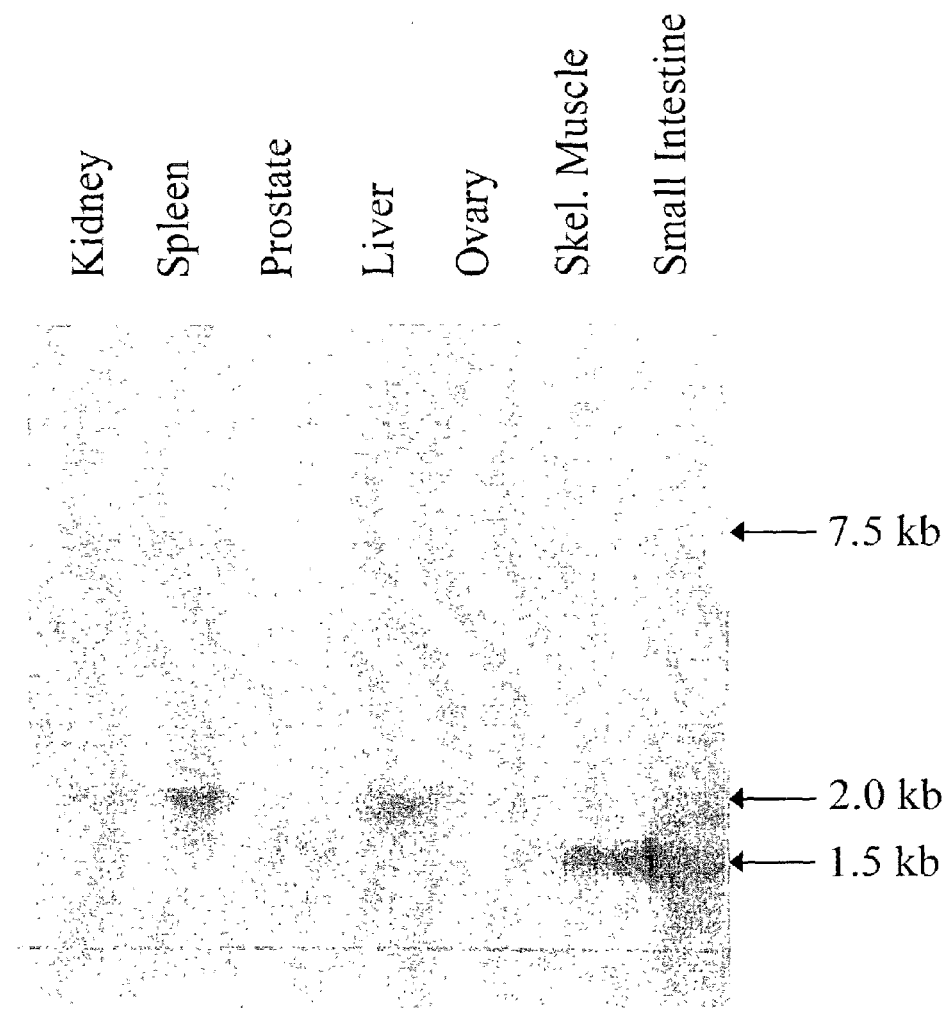
FIG. 2. VEGI is expressed as multiple transcripts in human tissue. VEGI expression in adult human tissues was determined by multi-tissue Northern blotting analysis, using $^{32}$P-labeled full length VEGI-$174$ cDNA as a probe. Three distinct VEGI-related messages of the indicated sizes are detected.
Figure 3:
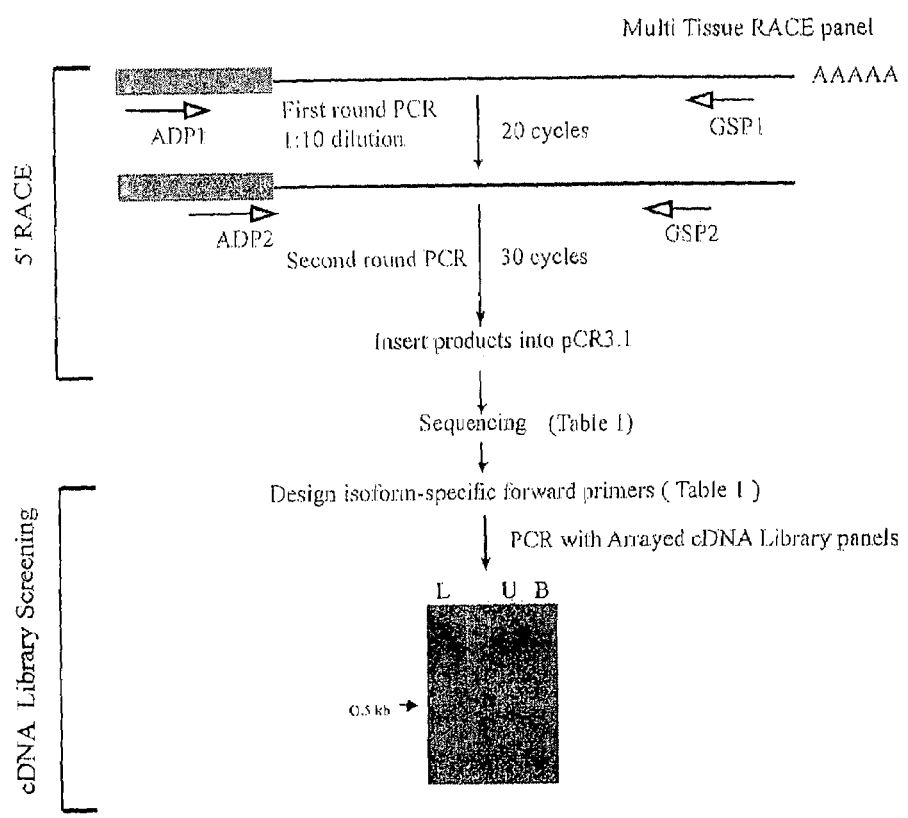
FIG. 3. Isolation of novel VEGI cDNAs. Scheme showing synthesis of 5'RACE products followed by cDNA library screening to isolate full-length VEGI cDNAs from various human tissues. Shaded boxes represent ligated 5' adaptors present in the RACE panel. PCR primers are denoted by arrows with open arrowheads. PCR products of different sizes are visualized by ethidium bromide staining. The PCR products were isolated and subjected to sequencing. L=lung; U=uterus; B=brain. A 1 Kb DNA molecular weight ladder is shown between the L and U lanes.

With a full length cDNA of the originally discovered human VEGI as a probe, Northern blots of normal human tissues consistently revealed multiple bands of the following sizes: 7.5 kb, 2.0 kb and 1.5 kb (FIG. 2). These multiple transcripts for VEGI showed somewhat overlapping tissue distribution and demonstrated the existence of a VEGI family. In order to elucidate the structure of the VEGI-related transcripts, we undertook the isolation of VEGI isoforms by PCR. With VEGI-specific 3' primers, 5' RACE was employed to amplify 5' ends of VEGI messages from a number of human tissues. The RACE products were then cloned into pCR3.1 and sequenced (FIG. 3). Sequence analysis revealed two novel VEGI sequences, VEGI-$_{251}$ and VEGI-$_{192a}$ (Table 8 and FIG. 3). Based on these 5' sequences, isoform-specific primers were designed, and full-length cDNA clones isolated from arrayed cDNA panels. Three VEGI isoforms were thus isolated from fetal brain, adult uterus and lung (FIGS. 3A and B). The novel cDNAs contain open reading frames of $_{251}$ and 192 amino acids (FIG. 3B), with calculated molecular weights of 28 086 and 21 952 Daltons respectively. The two novel VEGI peptides, VEGI-$_{251}$ and VEGI-$_{192a}$, share the carboxyl 151 amino acid residues with the original VEGI (Zhai, et al. *Int J Cancer* 82, 131-136, 1999), now referred to as VEGI-$_{174}$. The hydropathic profile of the proteins indicated a hydrophobic region of 20 amino acid residues in VEGI-$_{251}$ near its N-terminus (FIG. 3B) which is absent from VEGI-$_{174}$ and VEGI-$_{192a}$. This sequence was predicted to comprise a signal peptide. Another highly hydrophobic, possibly transmembrane region, was previously identified at the N-terminus of VEGI-$_{174}$ (FIG. 3B).

Example 17

Expression of VEGI Isoforms

Figure 4:
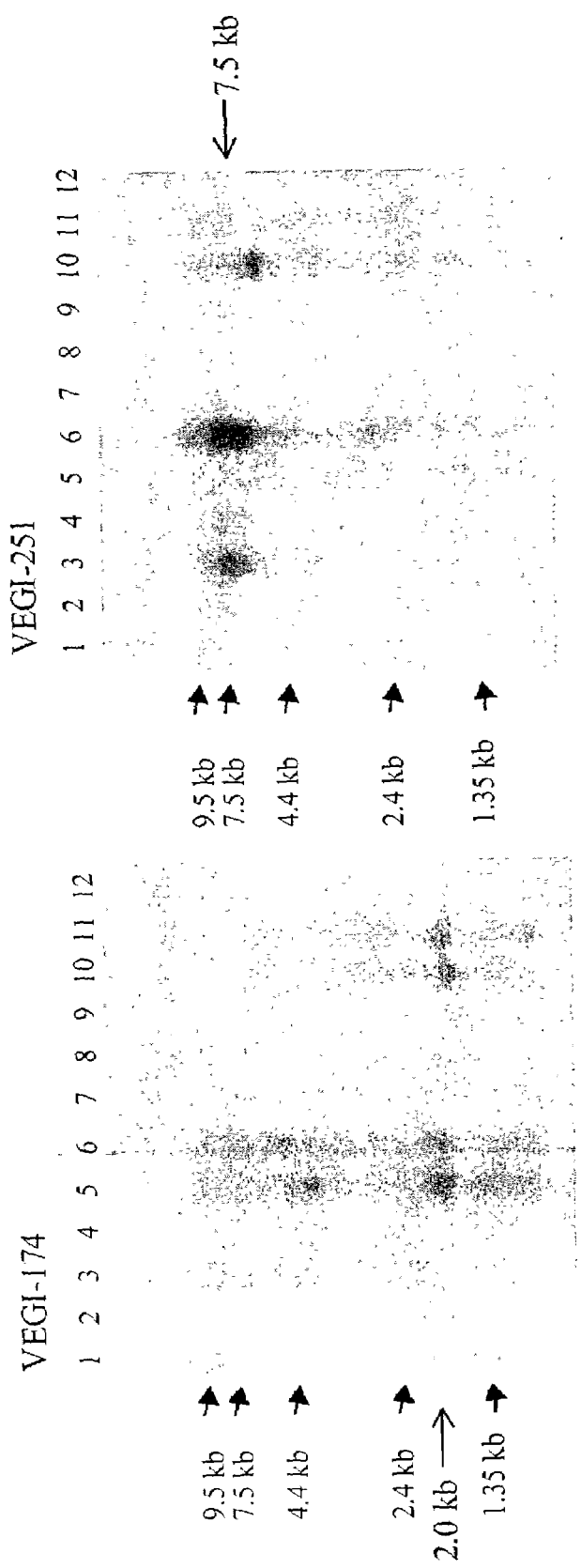
FIG. 4. Differential expression of VEGI-$_{174}$ and VEGI-$_{251}$ in human tissues. Northern blotting analysis of VEGI expression in adult human tissues were performed with cDNA fragments specific for VEGI-$_{251}$ and VEGI-$_{174}$. A 2 kb transcript is detected with the VEGI-$_{174}$ probe, while a 7.5 kb message is detected with the VEGI-$_{251}$ probe. The human tissues examined were as follows: 1. Peripheral blood leukocytes, 2. Lung, 3. Placenta, 4. Small intestine, 5. Liver, 6. Kidney, 7. Spleen, 8. Thymus, 9. colon, 10. Skeletal muscle, 11. Heart, 12. Brain.

The individual expression patterns of the isoforms was further examined by Northern analysis with multi-tissue blots. A 7.5 kb VEGI-$_{251}$ transcript was detected in placenta, kidney, lung and liver while the 2 kb VEGI-$_{174}$ transcript was observed in liver, kidney, skeletal muscle and heart (FIG. 4). When these same probes were used on a multi-tissue RNA dot blot, it was observed that, in addition to overlapping expression between VEGI$_{251}$ and $_{174}$ in prostate, salivary gland and placenta, VEGI-$_{251}$ was more abundant than VEGI-$_{174}$ in fetal kidney and fetal lung, while VEGI-$_{174}$ is more abundant in heart, skeletal muscle, pancreas, adrenal gland, and liver (Table 10). The significance of such expression patterns is at present not readily apparent to us. VEGI-$_{192a}$ mRNA could not be readily detected by Northern blotting because of its low abundance.

Figure 5:
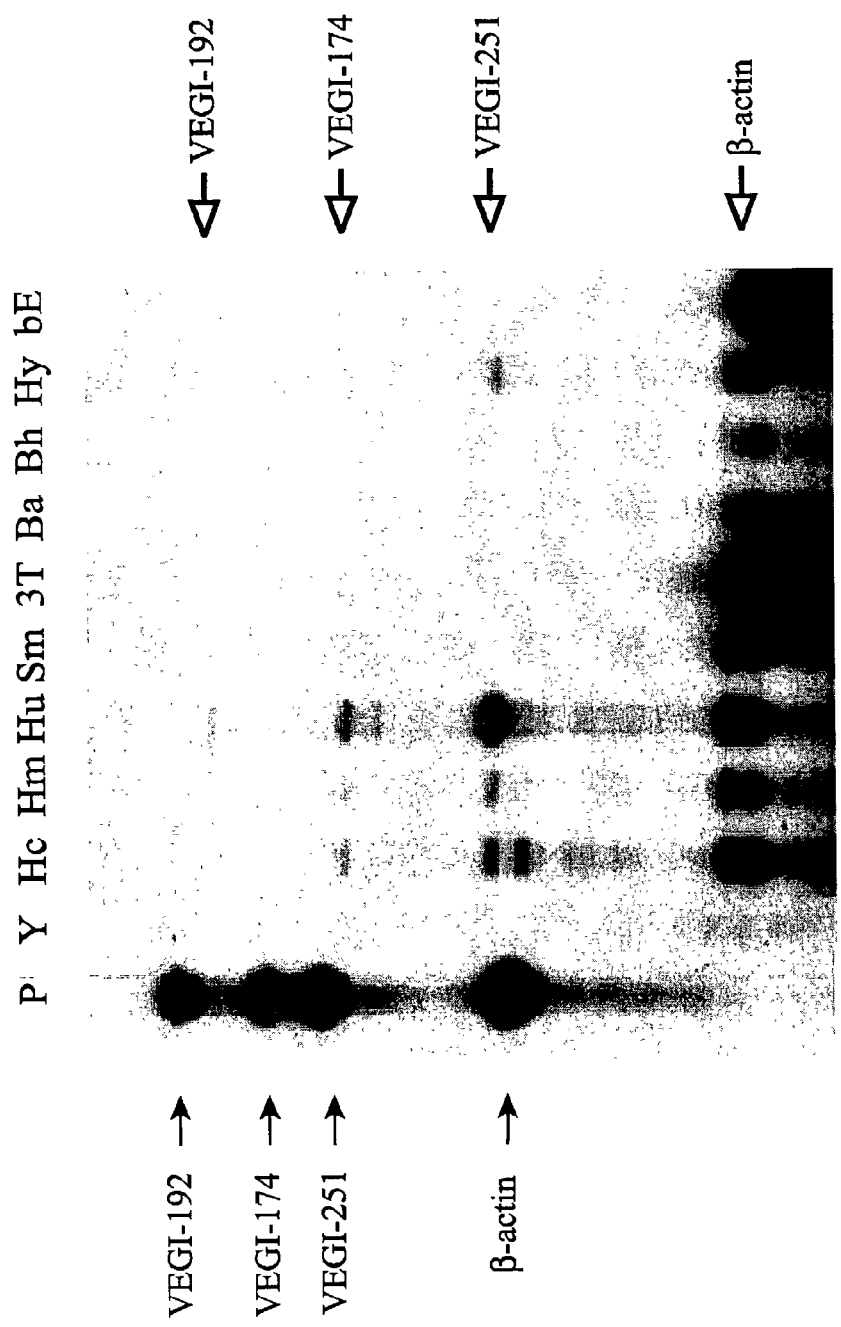
FIG. 5. Ribonuclease protection analysis of VEGI isoforms in various cultured cells. Total RNA from each culture shown was hybridized with isoform-specific VEGI probes and β-actin for loading control. Full-length undigested probes are shown in the probes lane (P), indicated by solid arrowheads, and products of RNase protection are indicated by open arrowheads. Y=yeast RNA, Hc=human coronary artery endothelial cells, Hm=human dermal microvascular endothelial cells, Hu=human umbilical vein endothelial cells, Sm=human Coronary artery smooth muscle cells, 3T=NIH3T3 embryonic mouse cell line, Ba=adult bovine aortic endothelial cells, Bh=fetal bovine heart endothelial cells, Hy=EA.Hy926 human hybridoma cells, bE=bEND.3 mouse brain endothelioma cells.

VEGI expression in vitro was also examined by RNase protection assay. In agreement with previous observations for VEGI-$_{174}$, VEGI-$_{251}$ and VEGI-$_{192a}$ were detected in the same cell types as VEGI-$_{174}$, being present in human endothelial cells, including coronary artery endothelial (HCAE), human umbilical vein endothelial (HUVE) and human microvascular endothelial (HMVE) cells and undetectable in human coronary artery smooth muscle (HCASM), ABAE and mouse endotheliomas bEND.3 (FIG. 5). It should also be noted that more than one isoform was expressed in the same cell type, with VEGI-$_{251}$ being the most abundant. This suggests that the expression of these isoforms plays a regulatory role in VEGI function.

TABLE 10

Expression of VEGI-$_{174}$ and VEGI-$_{251}$ RNA in human tissue*

| Tissue | VEGI-$_{174}$ | VEGI-$_{251}$ |
|---|---|---|
| Brain | ++ | − |
| Heart | ++++ | − |
| Aorta | + | − |
| Sk. Muscle | +++ | − |
| Colon | ++ | ± |
| Bladder | + | ± |
| Uterus | + | − |
| Prostate | ++ | +++ |
| Stomach | +++ | ++ |
| Testis | + | − |
| Ovary | + | − |
| Pancreas | ++++ | ± |
| Pituitary gl. | ++ | − |
| Adrenal gl. | +++ | ± |
| Thyroid gl. | + | − |
| Salivary gl. | ++++ | ++++ |
| Mammary gl. | + | ± |
| Kidney | ++ | +++ |
| Liver | ++++ | − |
| Sm. Intestine | +++ | ++ |
| Spleen | ++ | ± |
| Thymus | ++ | ± |
| Peri. Leukocyte | + | − |
| Lymph note | + | ± |
| Bone marrow | + | − |
| Appendix | + | + |
| Lung | ++ | ++ |
| Trachea | ++ | + |
| Placenta | ++++ | +++ |
| Fetal brain | + | − |
| Fetal heart | + | − |
| Fetal kidney | + | ++++ |

TABLE 10-continued

Expression of VEGI-$_{174}$ and VEGI-$_{251}$ RNA in human tissue*

| Tissue | VEGI-$_{174}$ | VEGI-$_{251}$ |
|---|---|---|
| Fetal liver | ++ | − |
| Fetal spleen | + | + |
| Fetal thymus | + | − |
| Fetal lung | + | ++++ |

*Comparison of VEGI-$_{174}$ and VEGI-$_{251}$ RNA expression using multi-tissue human poly A+ RNA dot blot.
−: undetectable;
±: not significantly above background;
+: very low;
++++ abundant. VEGI-$_{92a}$ expression was undetectable.

Example 18

Human VEGI Gene Organization

In order to determine the structural relationship of the three VEGI transcripts, the organization of the human VEGI gene was analyzed. This was done with a BAC clone as well as with genomic DNA isolated from human placenta samples. It was found that the human VEGI gene spans over 17 kb, with 4 exons and 3 introns (FIG. 6). The intron-exon junctions conform to the GT-AG rule. Based on the size of fragment 2, intron 1 was estimated at 13-15 kb, although sequence information could not be obtained from this PCR product. All three isoforms share a common 438 bp region encoding residues 29-174 of VEGI-$_{174}$ (Table 12) encoded by exon IVb (FIG. 6), but their 5' regions are generated from alternative exon usage. Interestingly, VEGI-$_{251}$ and VEGI-$_{192a}$ utilize exonic splice acceptor sites to generate their respective products (Table 11). Ribonuclease protection and 5' RACE studies using genomic probes and HUVE RNA indicated that the putative transcription initiation site for VEGI-$_{251}$ is located about 100 bp upstream of its ATG (unpublished, Chew LJ) but those for VEGI-$_{174}$ and VEGI-$_{192a}$ have yet to be mapped. Due to the very low abundance of VEGI-$_{192a}$ RNA, subsequent studies were focused on VEGI-$_{251}$. While it is presently unclear whether all the isoforms initiate at the same promoter, we nonetheless reasoned that the significance of generating multiple transcripts could lie in differential regulation of synthesis, which in turn may point toward the relative importance of one particular VEGI isoform.

TABLE 11

Human VEGI gene organization (SEQ ID NOS:34-41)

| EXON | size | 5' splice donor | INTRON size | 3' splice acceptor | EXON |
|---|---|---|---|---|---|
| I | 310 bp | AGTTCAG<br>gtaagccacatggca<br>(SEQ ID NO:34) | ~13 kb | Tttctttcccaatag<br>GCTCTAAAAGGACA<br>(SEQ ID NO:37) | II |
| II | 43 bp | CACATCAGCAAGTTT<br>gtaagtatgctcatc<br>(SEQ ID NO:35) | ~400 bp | *aatgtctagcacat<br>caaaagTATGCACTT<br>CATTTT<br>(SEQ ID NO:38) | IIIa |
| IIIa | 661 bp | | | CTCCTTTTGTTACAG<br>ATGCACCT<br>(SEQ ID NO:39) | IIIb |
| IIIb | 48 bp | GGGCACACCTGACA<br>gtaagcctccctgct<br>(SEQ ID NO:36) | ~458 bp | *ttcagattctatca<br>gCCCTCTCTCTTTCT<br>CTCCT<br>(SEQ ID NO:40) | |
| IVa | 1092 bp | | | GGGCACACCTGACAG<br>TTGTGAGA<br>(SEQ ID NO:41) | |
| IVb | 1592 bp | | | | |

¶Organization of the human VEGI gene, with the size of each exon and approximate size of introns. Exon numbers are given in FIG. 6. Uppercase letters indicate exon sequence, and lower case indicate intron sequence. Consensus splice junctions are underlined.
*The extreme 5' ends of VEGI-$_{192a}$ and VEGI-$_{174}$ mRNA have not yet been identified, therefore intron-exon junctions in these regions are unknown.

TABLE 12

Amino acid sequence of VEGI polypeptide (SEQ ID NO:42)

PTQHFKNQFPALHWEHELGLAFTKNRMNYTNKFLLIPESGDYFIYSQVTFRGMTSECSEI    (SEQ ID NO:42)
RQAGRPNKPDSITVVITKVTDSYPEPTQLLMGTKSVCEVGSNWFQPIYLGAMFSLQEGD
KLMVNVSDISLVDYTKEDKTFFGAFLL

Example 19

VEGI Isoform Transcripts are Induced in Parallel by TNFα

Figure 7:
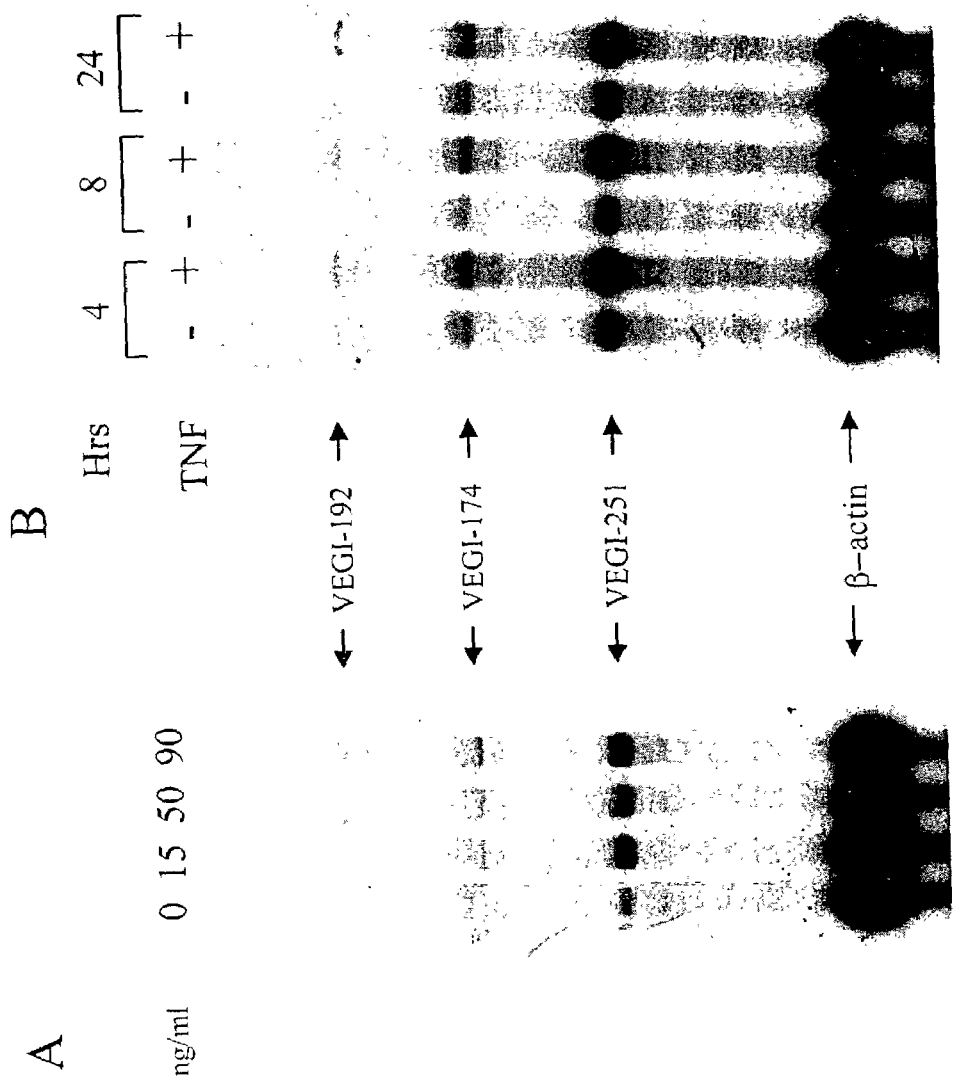
FIG. 7. TNFα induces VEGI isoform expression in both microvessel and large vessel endothelial cells. Ribonuclease protection assays showing parallel induction of VEGI expression. Arrows indicate protected RNAs. A. HMVE cells treated with TNFα at 15, 50 and 90 ng/ml over 24 hr. B. Induction of VEGI gene expression by TNFα in HUVE cells. HUVE cells were treated (+) with 20 ng/ml TNFα for 4, 8 and 24 hr. Controls (−) received corresponding vehicle treatments.

To test for the possibility of differential regulation in VEGI isoform transcription, VEGI gene regulation using an anti-angiogenic paradigm of TNFα treatment was analyzed. Although many studies describe anti-proliferative effects of proinflammatory cytokines like TNFα on endothelial cells, these cytokines can also be angiogenic depending on dose and system used (see Discussion). Such modulatory effects on endothelial cells may serve to regulate the levels of an endothelial cell-specific cytokine such as VEGI. We found that concentrations of 15 ng/ml of TNFα or higher could induce an increase in VEGI RNA levels in both large vessel (umbilical vein) and small vessel (dermal microvascular) endothelial cells (FIG. 7), and that all isoforms were induced in both these endothelial cell types. It is also clear that VEGI-$_{251}$ remains the most abundant of the isoforms. The parallel upregulation of VEGI transcripts by TNFα not only indicates that VEGI-mediated activity is potentially a target of TNFα action, but also that the control of VEGI function through the synthesis of multiple peptides most likely lies at the post-transcriptional level.

Example 20

Subcellular Localization

Figure 8:
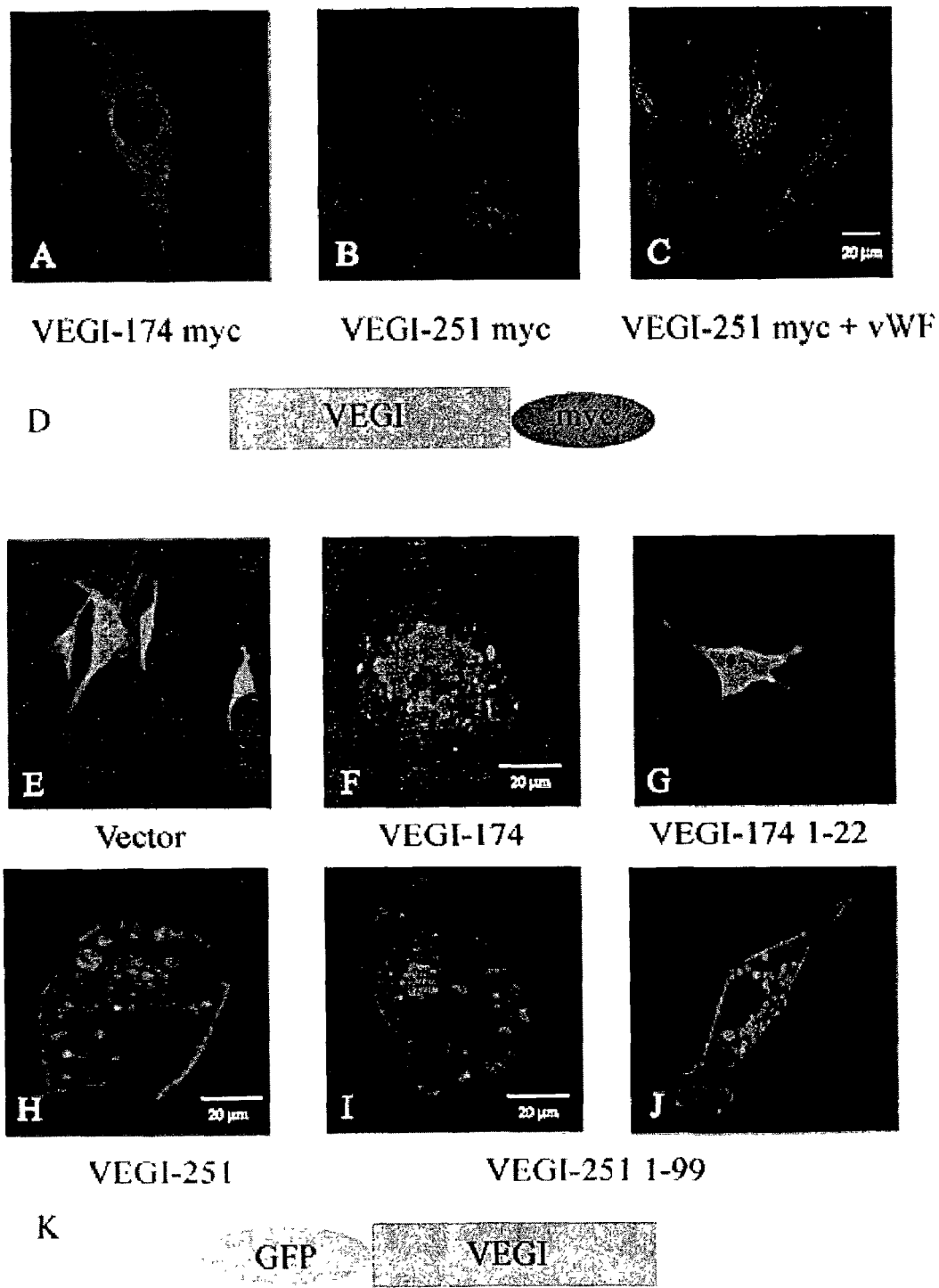
FIG. 8. Intracellular localization of recombinant VEGI-$_{174}$ and VEGI-$_{251}$ in transfected endothelial cells. A. VEGI-$_{174}$-myc and VEGI-$_{251}$-myc (B) were detected in transfected ABAE cells by Texas Red staining of the associated myc tags. C. Double staining of VEGI-$_{251}$-myc (red) and von Willebrand Factor (green) in transfected HUVE cells. The diagram in D depicts VEGI expression constructs with a C-terminal myc tag. E-J. N-terminal tagged GFP-VEGI constructs showed distinct distribution in ABAE cells. Cells transfected with vector plasmid (E) showed GFP throughout the cell whereas three VEGI constructs (F, H-J) resulted in localized GFP distributions. In I and J, VEGI-$_{251}$ 1-99 directed GFP distribution in the plasma membrane. K. The GFP tags in the expression constructs used in F through J are located at the amino termini of the VEGI fragments.

Since TNF-like peptides are often present as both membrane-bound and soluble forms, the possibility by using recombinant VEGI-transfected ABAE cells was investigated. Localization experiments were performed with constructs bearing a myc tag at the C-termini of VEGI coding regions (FIG. 8). Expression constructs of VEGI isoforms in pcDNA3.1-myc were transfected into ABAE cells and the distribution of the VEGI-myc product analyzed by immunocytochemistry with an anti-myc antibody. VEGI-$_{174}$ was detected in the cell with endoplasmic reticulum/Golgi-like distribution (FIG. 8A). However, VEGI-$_{251}$ showed a more restricted peri-nuclear granular staining (FIG. 8B). In both cases, cell surface localization was not apparent by confocal fluorescence microscopy. In HUVE cells, the VEGI-$_{251}$-myc-containing vesicles were found not to be Weibel-Palade bodies of endothelial cells, because the myc signal did not colocalize with von Willebrand factor (vWF) staining (FIG. 8C). It is therefore possible that, in contrast with vWF, processing of VEGI-$_{251}$ does not involve a regulated secretory pathway in endothelial cells.

To determine whether the isoforms might exhibit N-terminus directed differences in subcellular localization, chimeric GFP-VEGI expression constructs were made with both full-length VEGI and their corresponding unique N-terminal sequences. These constructs, with GFP tags at their N-termini (FIG. 8), were transiently transfected into ABAE cells. As shown in FIGS. 8E through 8J, with the exception of 8G, the distribution of GFP-VEGI was distinct from that of untargeted GFP. Full length VEGI-$_{174}$ showed localization in ER/Golgi, as previously seen with myc-tagged VEGI-$_{174}$ while the first 22 residues of VEGI-$_{174}$ appeared inadequate for targeting GFP distribution to a specific intracellular organelle (FIG. 8G). In contrast, the first 99 amino acids of VEGI-$_{251}$ was sufficient to result in GFP localization in vesicles which abutted the plasma membrane. This distribution was seen as a fluorescent band that outlined the cellular boundary (FIGS. 8H through J). Our observations suggested that VEGI-$_{251}$ might be located in secretory vesicles which underwent constitutive exocytosis.

Unlike GFP-VEGI-$_{251}$, the lack of plasma membrane localization of VEGI-$_{251}$-myc (FIG. 8B) strongly suggested that the C-terminal myc tag was lost from the cell, possibly because of cleavage of the secretory signal and secretion of the soluble C-terminal fragment. It was known that true signal sequences that were placed downstream of the N-termini, such as in GFP-VEGI-$_{251}$ and GFP-VEGI-1-99, were not cleaved during synthesis in the ER. This difference in distribution patterns of VEGI-$_{251}$ with C-terminal and N-terminal tags was in agreement with a secretory mechanism that involved cleavage of VEGI-$_{251}$ at or within its N-terminal sequence prior to release into the extracellular milieu.

Example 21

Demonstration of VEGI in Cell-conditioned Media

Figure 9:
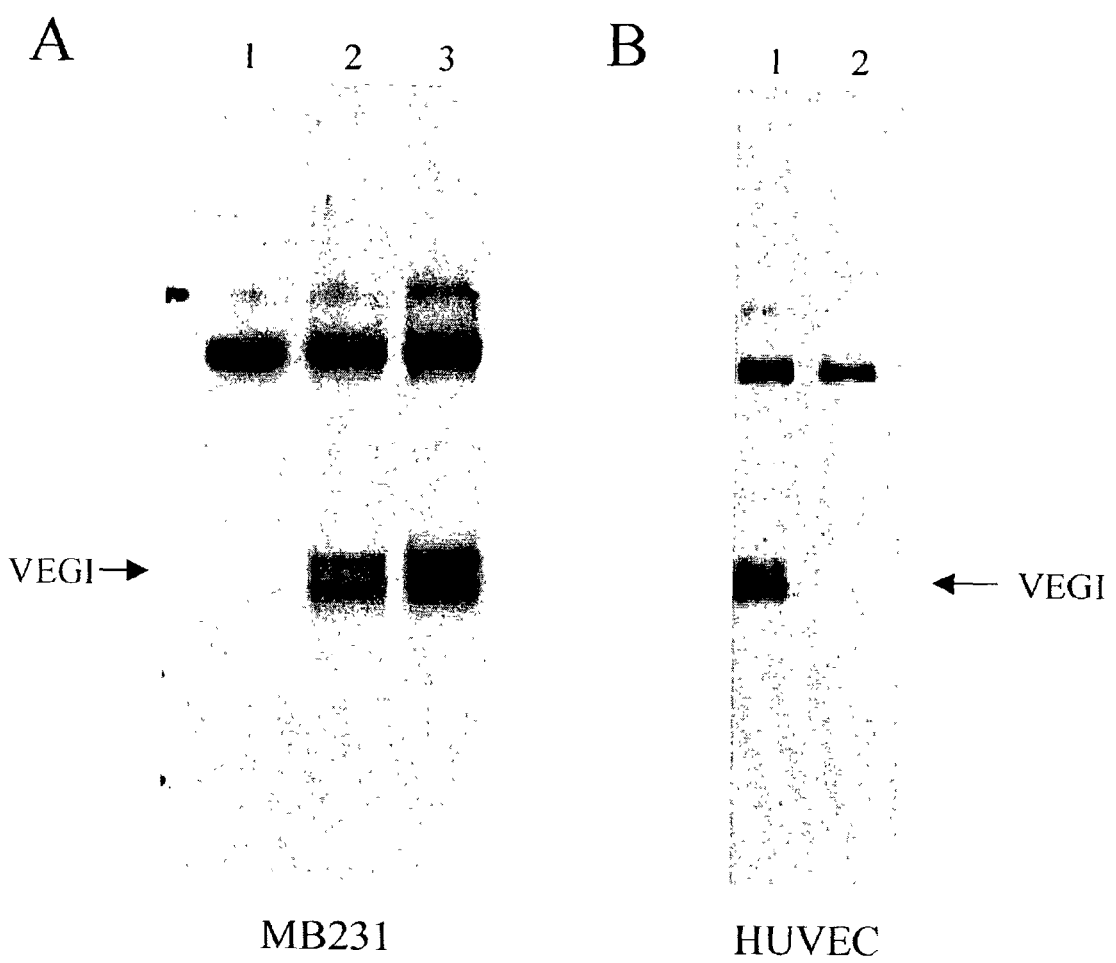
FIG. 9 Detection by Western analysis of VEGI-$_{251}$ in medium conditioned by transfected MB231 cells and untransfected HUVE cells. A. Conditioned medium from stable transfectants of MDA-MB231. Lane 1=pcDNA3 vector only, Lanes 2 and 3=two independent clones expressing VEGI-$_{251}$. B. Lane 1=HUVE cell-conditioned medium, Lane 2=HUVE cell lysate. In both experiments, conditioned media were concentrated with Centricon columns (MW cutoff 10,000), immunoprecipitated using polyclonal antibody, then subjected to SDS-PAGE and Western detection using monoclonal antibody 1-8F against the common C-terminal region of VEGI (residues 29-$_{174}$). Both panels show VEGI peptides of approximately 25 kD.

Given the hydrophobic residues in the N-terminus of VEGI-$_{251}$ and its observed subcellular distribution, it appears likely that VEGI-$_{251}$ is a secreted protein. To test this hypothesis, stable transfectants of VEGI-$_{251}$ in MDA-MB-231 breast cancer cells were generated. As a negative control, transfectants of pcDNA3 vector were also made. Expression of the constructs in MDA-MB-231 was confirmed by RNase protection assay. It should be noted that the survival and proliferation of these cells in vitro was not affected by either vector or VEGI transfection. The conditioned media of the MB-231 transfectants was collected, concentrated and immunoprecipitated with a polyclonal VEGI antibody and subjected to Western analysis with an anti-VEGI monoclonal antibody 3-12D. Our results revealed a protein of molecular weight of about 25 kD (FIG. 9A). The appearance of the doublet cannot be readily explained, but may be the result of alternate glycosylation or other post-translational modification of the recombinant peptide in transfected MB231 cells. No VEGI protein was detected in media from untransfected cells or cells bearing the empty pcDNA3 vector (FIG. 9A). VEGI-$_{174}$ could not be detected in conditioned medium under similar experimental conditions (not shown). In a separate experiment, Western analysis of concentrated HUVE cell-conditioned medium also revealed a band of similar molecular weight as that obtained with VEGI-$_{251}$ transfectants, as did HUVE cell-conditioned medium immunoprecipitated with the polyclonal antibody (FIG. 9B). These observations indicate that VEGI-$_{251}$ is not membrane-bound but is instead a secreted protein.

Example 22

Overexpression of VEGI-$_{251}$ in Endothelial Cells Causes Cell Death

Figure 10A:
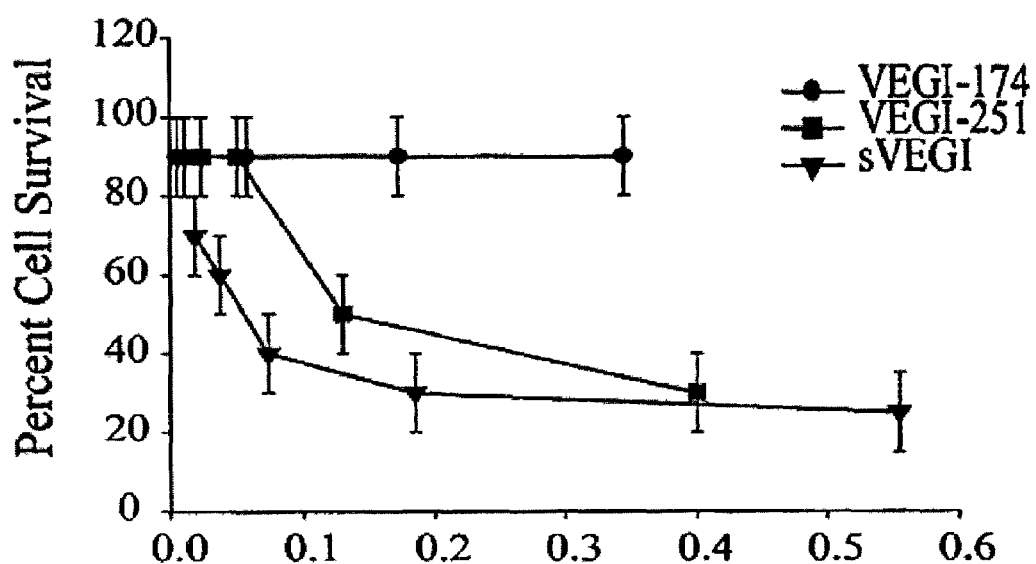
FIG. 10. Overexpression of VEGI-$_{251}$ causes endothelial cell death and interferes with tumor neovascularization. A. Lentivirus delivery of secreted VEGI is lethal to HUVE cells. Dose-dependent cytotoxicity of lentiviral stock expressing VEGI-$_{251}$ and sVEGI compared with VEGI-$_{174}$. Twenty four hours following viral infection, adherent cells remaining in culture were counted by Coulter counting. Viral p24 levels were estimated and viral dose is expressed as multiplicity of infection (MOI). Values shown are mean±SEM of three independent experiments. B. Retardation of xenograft MDA-MB231 breast tumor growth by VEGI-$_{251}$ and sVEGI. Pools of stably transfected MDA-MB231 cells expressing the indicated construct were injected subcutaneously into mammary fat pads of female athymic mice, and tumor sizes monitored in a blind manner. Control mice received MDA-MB231 cells transfected with empty pcDNA3 vector. Attenuation of tumor growth was observed for both VEGI-$_{251}$ and sVEGI, but not for full length VEGI-$_{174}$. C. VEGI-$_{251}$ and sVEGI transfection result in reduced microvessel densities in MB231 xenograft tumors. Paraffin sections (5 μm) from tumors were taken from mice described in FIG. 10A. Vessels were identified by CD31 immunostaining as described in Materials and Methods. One-way analysis of variance was used. a: P<0.0005; b: P<0.05 vs control xenografts with vector pcDNA3.

In order to test the biological activity of VEGI-$_{251}$ on endothelial cells, a lentivirus gene delivery system was selected to transfect HUVE cells with VEGI expression constructs. The lentiviral gene delivery was first tested with a GFP construct and confirmed that over 90% HUVE cells could be transduced (not shown). Our observations with VEGI-$_{174}$, VEGI-$_{251}$ and the secreted form of VEGI with the IL6 signal peptide, sVEGI, showed that only the secreted forms of VEGI, including VEGI-$_{251}$ and sVEGI, were cytotoxic to HUVEC (FIG. 10A), while VEGI-$_{174}$ was without effect.

These results indicate that HUVE cells bear membrane receptors for VEGI that can become activated via an autocrine mechanism.

Example 23

Anti-tumor Activity of VEGI-$_{251}$

It has been previously shown that a recombinant form of VEGI-$_{174}$ carrying the IL-6 secretory signal peptide, sVEGI, was effective in inhibiting the growth of MC38 colon carcinoma tumors in vivo (Zhai, et al. *Int J Cancer* 82, 131-136, 1999). Since native VEGI-$_{251}$ is a secreted protein, we determined whether it could also inhibit the growth of human xenograft tumors in vivo. Fifteen lines of stably transfected MDA-MB-231 clones for each construct were selected, with five lines from vector-transfected controls. Cells from each group were pooled and injected into mammary fat pads of female athymic nude mice. Tumor volumes were determined as a function of time after injection. Similarly pooled cell cultures of VEGI-$_{174}$ and sVEGI-transfected clones were compared. Pooled vector-transfected clones were used as controls. Untransfected parental cells were also assayed and were found to be identical with the vector-transfected clones.

Figure 10B:
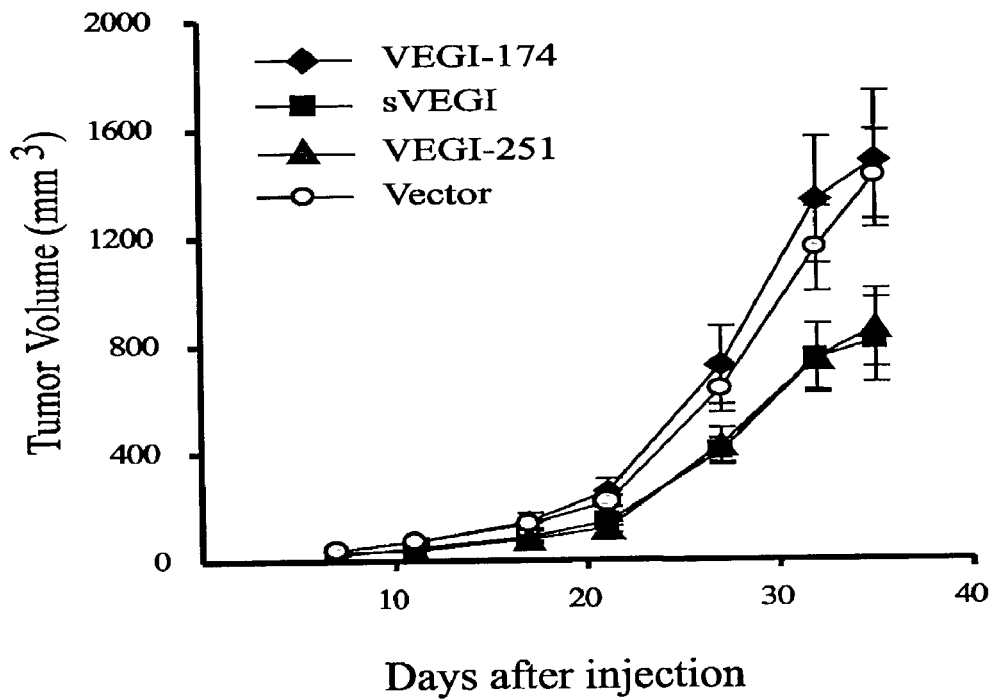
Figure 10C:
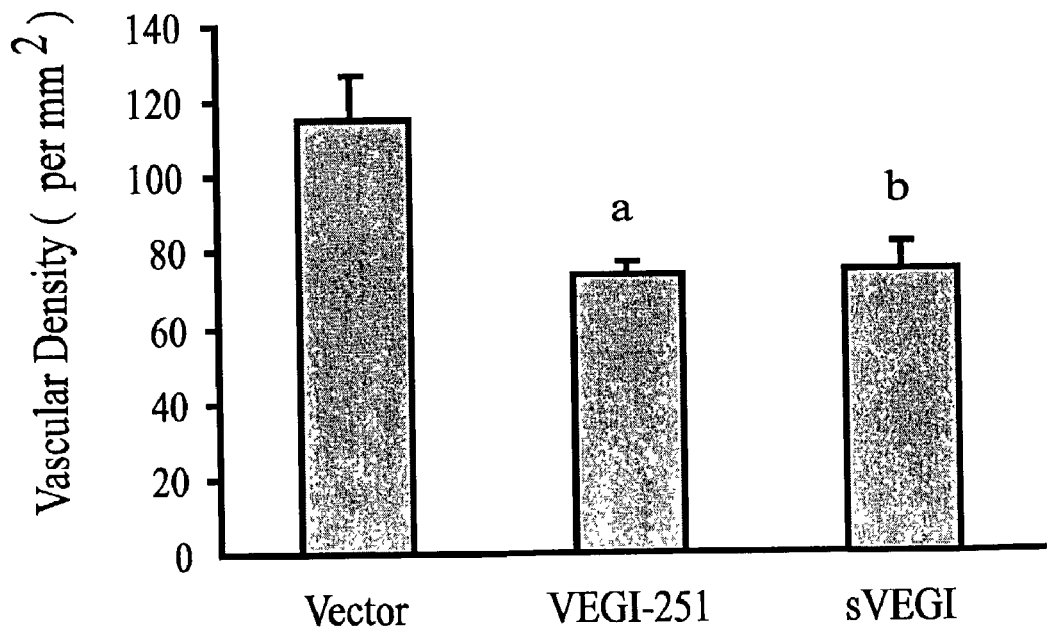

Our results show that overexpression of full length VEGI-$_{174}$ by cancer cells had little effect on the growth of the xenograft tumors (FIG. 10B). However, overexpression of the intact VEGI-$_{251}$ as well as the sVEGI fusion protein retarded tumor growth significantly. These observations are in complete agreement with the effect of lentiviral transfection in vitro (FIG. 10A), confirming the biological activity of native VEGI-$_{251}$.

We then determined the effect of full-length VEGI-$_{251}$ overexpression by cancer cells on tumor neovascularization. Tumor-associated microvessel density was found to be significantly reduced with the expression of VEGI-$_{251}$. The extent of reduction was comparable to that in sVEGI overexpressing tumors. Since the sVEGI fusion protein consists of the secretion signal peptide of IL6 and residues 23-$_{174}$ of VEGI-$_{174}$, the results indicate that residues 23-$_{174}$ contained the biological equivalent of native VEGI-$_{251}$. Taken together, these findings demonstrate that secretion of VEGI-$_{251}$ into the extracellular matrix is necessary for its anti-tumor activity. In addition, similar to sVEGI, this anti-tumor activity of VEGI-$_{251}$ is not due to a direct effect on tumor cells, but rather to interference with the development of tumor-associated vasculature.

Example 24

Identification of Potential Isoforms of VEGI

It is observed that, when a Northern blot membrane of human tissues was analyzed with a VEGI cDNA probe, a multiple number of mRNA bands appear in different tissues (FIG. 11). Since the experimental conditions used in these experiments did not favor non-specific binding of the probes, and judging from the approximate sizes of the mRNA molecules, there were at least three isoforms corresponding to 7.5 kb, 2.0 kb, and 1.5 kb, respectively. The different distribution of these isoforms in various tissues suggested that they play different physiological roles.

Example 25

Confirmation of the Novel VEGI Isoforms

Figure 12:
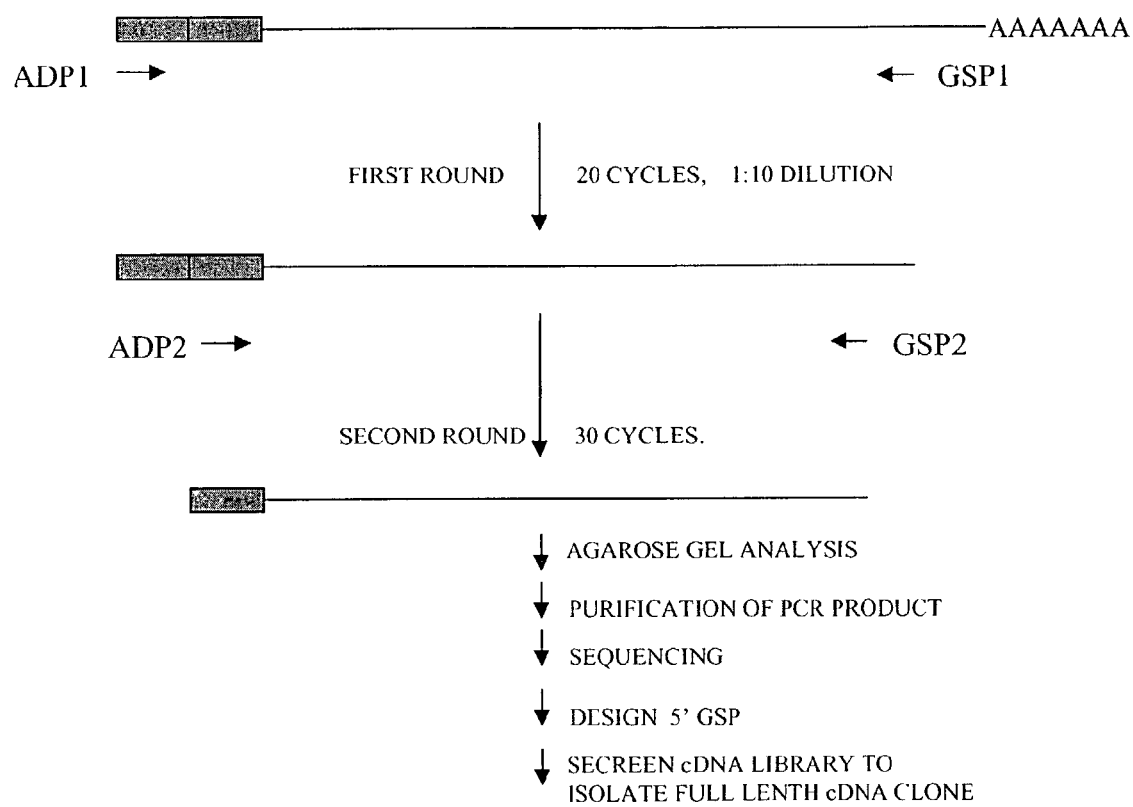
FIG. 12. A scheme illustrating RACE-PCR procedures used to search for possible VEGI isoforms. ADP1 and ADP2 indicate adapter-specific primers. GSP1 and GSP2 indicate gene-specific primers.
Figure 13:
FIG. 13. Photograph of the results of agarose gel electrophoresis of RACE-PCR products. Four PCR products of different sizes from different human tissues are visualized by using ethidium bromide staining. The PCR products were isolated and subjected to sequencing.

Using Rapid Amplification of cDNA End (RACE) (commercially available from OriGene Technology, Rockville, Md.), a panel of cDNA libraries representing various human tissues was used to search for the VEGI isoforms. This panel contains cDNA samples prepared from 24 individual human tissues, with an adapter ligated to the 5' end of each cDNA molecule. A gene-specific oligonucleotide primer (GSP) corresponding to part of VEGI cDNA and an adapter primer (ADP) were used to carry out polymerase chain reaction (PCR) (FIG. 12). Two rounds of nested PCR were performed using two pairs of oligonucleotide primers. After first round PCR (94° C. 3 min, 4 cycles of 94° C. for 30 sec, 65° C. for 30 sec, 72° C. for 2 min; 16 cycles of 94° C. for 30 sec, 60° C. for 30 sec, 72° C. for 2 min; then 72° C. for 6 min) with an adapter primer (ADP1, 5'-CGGAATTCGT CACTCAGCG-3') (SEQ ID NO:8) and a VEGI gene specific primer (GSP1, 5'-CCCG-GATCCT ATAGTAAGAA GGCTCC-3') (SEQ ID NO:9), the reaction products were diluted 1:10 with water. The diluted PCR samples were used in the second round PCR (94° C. for 3 min; 35 cycles of 94° C. for 30 sec; 54° C. for 30 sec, 72° C. for 2 min; then 72° C. for 6 min) with another adapter primer (ADP2, 5'-AGCGCGTGAA TCAGATCG3') (SEQ ID NO:10) and a VEGI gene specific primer (GSP2, 5'-CG-GTGGATCC CGAGTTTGTC TCACAACTG 3') (SEQ ID NO:11). The PCR products were fractionated on an agarose gel. Positive DNA fragments were excised from the gel, purified for sequencing analysis. Four PCR products with different lengths were obtained from different tissues (FIG. 13). These PCR products were subjected to DNA sequencing, confirming that the nucleotide sequences of these PCR products were different from each other. These isoforms are now named as VEGI-$_{174}$, VEGI-$_{192a}$, VEGI-$_{192b}$, and VEGI-$_{251}$, according to the number of amino acid residues in the proteins encoded by these cDNA molecules.

Example 26

Cloning of Full-length cDNA of the Isoforms

Figure 15:
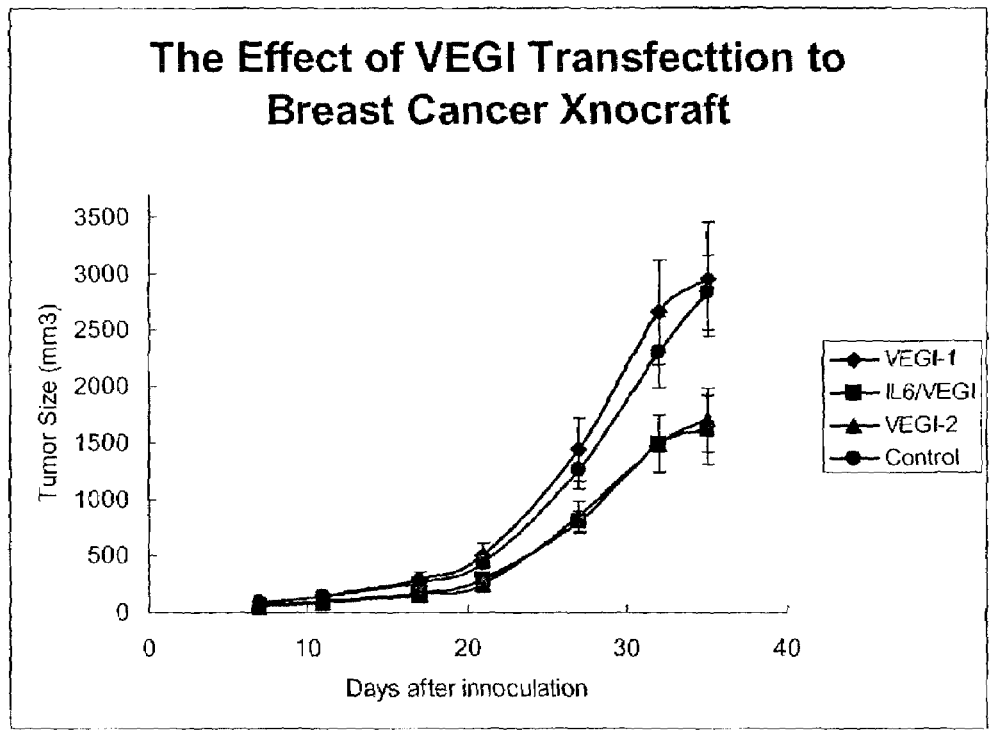
FIG. 15. Graph showing inhibition of the growth of xenograft tumors formed by MDA-MB-231 cells transfected with VEGI-$_{174}$, VEGI-$_{251}$, IL6/VEGI, or an empty pCDNA-3 vector. One million stably transfected cells are injected into the mammary fat pads of female athymic nude mice. There are 2 injection sites per animal and 5 animal per group. The groups are coded and the sizes of the xenograft tumors are monitored in a blinded manner. Statistically significant inhibition of the growth of the tumors are observed for the $VEGI_{251}$ or the IL6-VEGI overexpressing cells. $VEGI_{174}$ overexpression has no effect on the tumor growth.

Gene specific primers designed according to sequencing results of the PCR products obtained from the RACE experiments described above were used to repeat the second round PCR to confirm the specificity of their sequences. The purified RACE products were then cloned into plasmid pCR 3.1 of Invitrogen (San Diego, Calif.) to prepare high quality DNA samples for sequencing. Based on the presence of an in-frame stop codon and an initiation codon in the 5'-sequence of VEGI$_{192a}$ and VEGI$_{192b}$, the full-length cDNA molecule of VEGI$_{192a}$ was constructed with two pairs of nested PCR primers: Vg3A: 5'-AATCTCACCT GTCTCT-GCCT G-3' (SEQ ID NO:43) and Vg-3'-1: 5'-CTAAAC-CGTT GTCCCTGTGG-3' (SEQ ID NO:44); Vg3B: 5'-CCT-GTAAAAA TGGTTATAGT AG-3' (SEQ ID NO:45) and Vg-3'-2: 5'-GGTGGCAGAG GACTTTC-3' (SEQ ID NO:46). The full-length cDNA molecule of VEGI$_{192b}$ was constructed with primer vg$_{4b}$ 5'-CTCTACTTAC GCCAAGG-3' (SEQ ID NO:47) and primer JY2 5'-CCCG-GATCCT ATAGTAAGAA GGCTCC-3' (SEQ ID NO:48). The cDNA libraries from which the isoforms were identified was used for the PCR. Both VEGI$_{192a}$ and VEGI$_{192b}$ were cloned into pCR3.1 of Invitrogen (San Diego, Calif.). Since no in frame translation initiation codon could be found in the 5' sequence of VEGI$_{251}$, a pair of gene specific primers vg5B: 5'-CACCACATAC CTGCTTG-3' (SEQ ID NO:49) and vg161: 5'-GTGTAATCCA CCAAAGAG-3' (SEQ ID NO:12), were used to isolate a full-length VEGI$_{251}$ cDNA clone from Arrayed cDNA Library Panels of OriGene (Rockville, Md.). The cDNA sequence of VEGI-$_{192a}$ is shown in Table 13.

also analyzed. The overexpression of full length VEGI-$_{174}$ by the cancer cells had little effect on the growth of the xenograft tumors, and over-expression of the secreted form of the putative VEGI extracellular domain and the full length VEGI-$_{251}$ markedly inhibited tumor growth (FIG. 15). Furthermore, it was demonstrated that the VEGI protein was available in the tumors by carrying out immunohistochemical analysis of the tumor sections using a monoclonal antibody to VEGI. Some of the tumors (G9-1R) had cancer cells that produced a remarkable amount of VEGI-$_{251}$, while others had cancer

TABLE 13 cDNA sequence Of VEGI-$_{192a}$ (SEQ ID NO:33)

```
TTTTTTNTTTTNCTCAACNCCCCCCNATATTTATAACTGNATTTGGACCCNTGCNTAACCCAACATATATNTTTGAG
ANCCAAAGGGAANTTTTAGGTTTTCTCAAGAANTAATAGACAAACAGAGGCCCHGAGAGGGAAAGGGATTCNCCCAA
AGTCATATAGCTAAAGANTAGTTCCCACCCACTCTTCATCCCATTTCTTNTGGCCATCTATTCAGTGAATATAGTTA
AAGGGCCCTTGCANGANGGCAAAAAGCCAATTCACTCCTGTGAAAGAATTTTGTGGGAAAGAGCAGTGAGTTGTGCT
TTATTGAGCATTGGCCATGTGCAAAATTCATGNTAAGCACCNCCATNTATACTGTGCCCATCTTAGATGAGATGAGA
AAACAGGGTCTCAGGCAGGNTAGATAAACTTGCCCAAAGCCATCGGGCCAAGATTCATTTGTGTTCAAGACTCTTTC
TTGTGAGTCACCCTGTCCTTGGTCGTCCTTGCTGCGGGTGCCACATTCCAATCCAAAATCCTGCAAGGAGTGGCACT
GGACCAAGCTGGAGGAGATCAAGGTTTCTCTCCTATCATAGGCGCCATGCAACTCACAAAGGCCCGTCTTCATTTCA
GTCACCCTTTGTCTCATACAAAGCACATTTCTCCTTTTGTTACAGATGCACATCTTAGGGCAGACGGAGATAAGCCA
AGGGCACACTTGCAGTTGTGAGACAAACTCCCACACAGCACTTTAAAAATCAGTTCCCAGTTCTGCACTGGGAACA
TGAACTAGGCCTGGCCTTCACCAAGAACCGAATGAACTATACCAACAAATTCCTGCTGATCCCAGAGTCGGGAGACT
ACTTCATTTACTCCCGGGTCACATTCCGTGGGATGACCTCTGAGTGCAGTGAAATCAGACAAGCAGGCCGACCAAAC
AAGCCAGACTCCATCACTGTGGTCATCACCAAGGTAACAGACAGCTACCCTGAGCCAACCCAGCTCCTCATGGGGAC
CAAGTCTGTGTGCGAAGTAGGTAGCAACTGGTTCCAGCCCATCTACCTCGGAGCCATGTTCTCCTTGCAAGAAGGGG
ACAAGCTAATGGTGAACGTCAGTGACATCTCTTTGGTGGATTACACAAAAGAAGATAAAACCTTCTTTGGAGCCTTC
TTACTATAGCAGGAGAGCAAATATCATTATATGAAAGTCCTCTGCCACCAGCC
```

Example 27

Anti-angiogenic and Anticancer Activity of VEGI$_{251}$

A recombinant protein made of a truncated form of VEGI$_{174}$, consisting of residues 29-$_{174}$, is a potent inhibitor of tumorigenesis (Zhai Y, et al., *FASEB J.*, 13: 181-189, 1999; Zhai, Y, et al., *Int. J. Cancer,* 82:131-136, 1999). It is shown that VEGI has no direct effect on the growth of the cancer cells, and that the mechanism of action of VEGI in the inhibition of tumor growth is to inhibit the formation of blood vessels in the tumors. Therefore the full-length cDNA of VEGI$_{251}$ was transfected into a human breast cancer cell line MDA-MB-231, then implanted in the mammary fat pads of female athymic nude mice to show that the gene product was able to inhibit the growth of tumors by these cells. In order to inhibit the growth of the endothelial cells in the immediate surroundings of the cancer cells, it is necessary for the VEGI gene product to be released into the outside of the transfected cells. It was demonstrated that a) that the gene product could be found in the conditioned media of the transfected cells in culture, and b) the transfected cells could grow tumors in the nude mice.

The MDA-MB-231 breast cancer cells were transfected with either the empty vector, the full-length VEGI-$_{174}$ cDNA, the full-length VEGI-$_{251}$ cDNA, or with a fusion gene in which the VEGI protein was linked to a secretion signal peptide derived from interleukin-6 (IL6/VEGI). When analyzed by Western blotting, using a monoclonal antibody (13-2D) to VEGI, the gene product of VEGI-$_{251}$ was found in the conditioned media of the transfected cells (FIG. 14). In contrast, the gene product of the VEGI-$_{174}$ was not detectable in the conditioned media.

Figure 17:
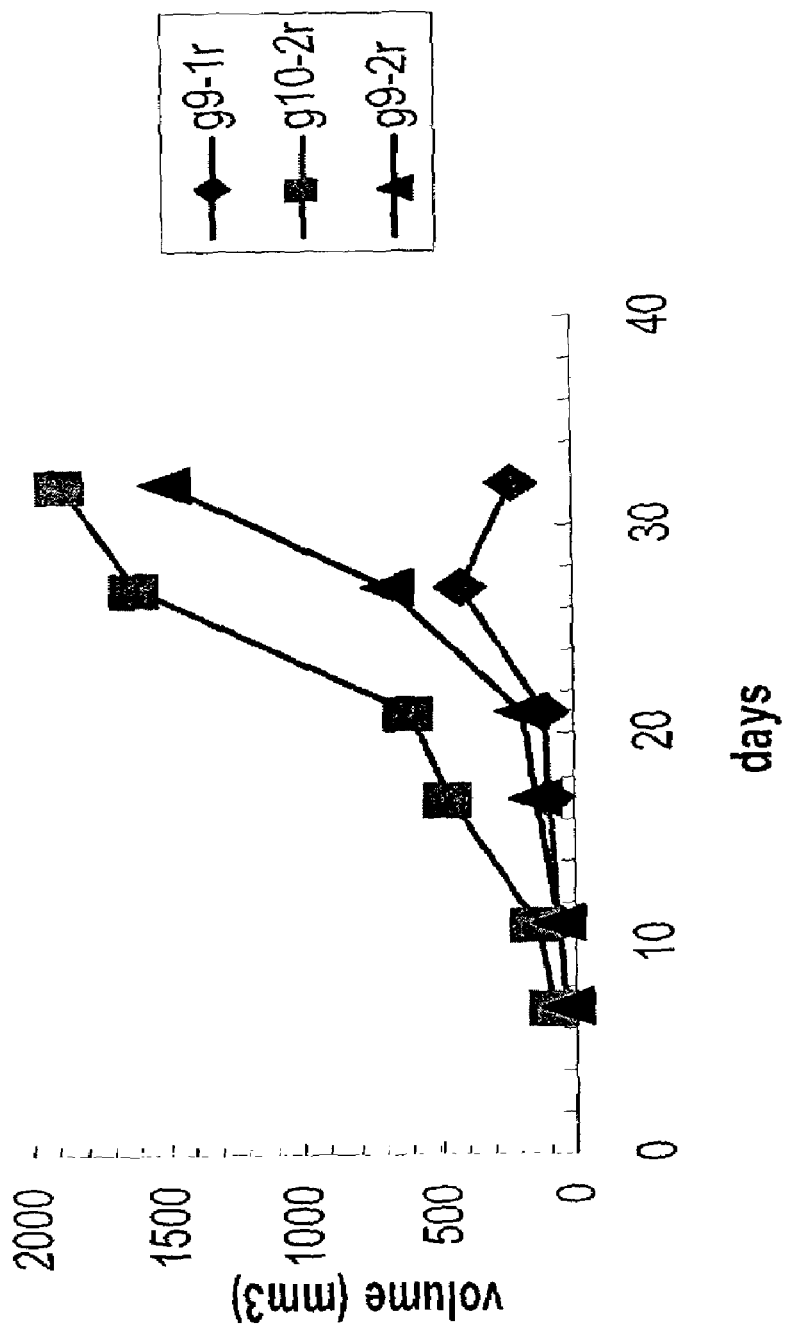
FIG. 17. Graph showing the growth rate of the tumors formed by the $VEGI_{251}$ transfected MDA-MB-231 cancer cells vary in accordance to the amount of VEGI produced by the cancer cells. Tumors in which VEGI level is higher (G9-1R) grow much more slowly than those with low VEGI levels (G9-2R).

The stably transfected MDA-MB-231 clones were injected into the mammary fat pads of athymic female nude mice ($1\times10^6$ cells per injection). The tumor sizes were determined as a function of time. Microvessel density in the tumor was cells that produced little VEGI-$_{251}$ (G9-2R), as compared with tumors formed by vector-transfected cells (G10-2R) (FIG. 16). The more VEGI-$_{251}$ produced by the tumors, the slower was the growth rate of the tumors (FIG. 17). These findings show that that VEGI-$_{251}$ is secreted by the transfected cancer cells, and that the secreted VEGI-$_{251}$ is a potent inhibitor of tumor growth by inhibiting the growth of the endothelial cells in the surroundings. In contrast, VEGI-$_{174}$ is not secreted by the cells, and consequently, cannot inhibit the growth of the endothelial cells.

Example 28

Tissue Distribution of VEGI Expression

Figure 18:
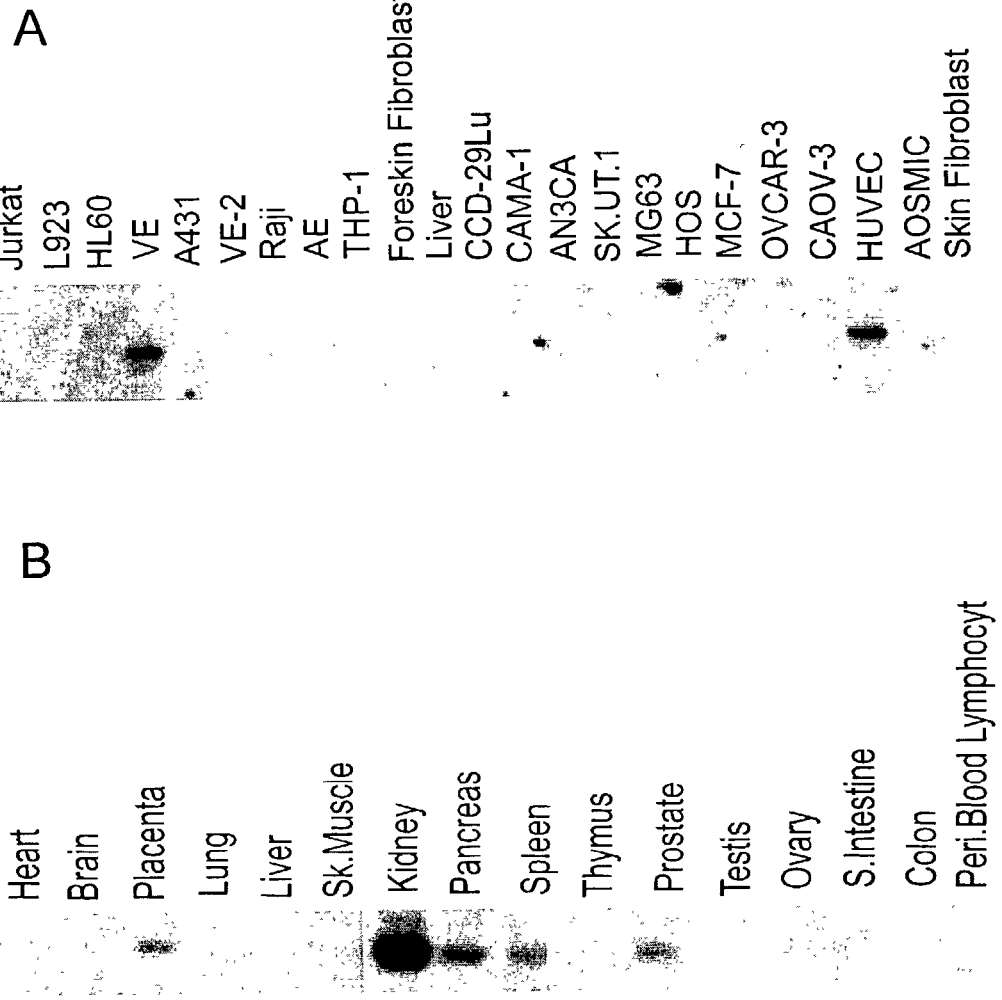
FIG. 18. Northern blotting analysis of VEGI transcripts. Panel A, VEGI expression in human cells: Jurkat, human T cell leukemia cell; L923, human embryonic kidney cell; HL60, human promyelocytic leukemia; V.E, human venous endothelial cell (10th passage); A431, human epidermoid carcinoma; V.E.-2, human venous endothelial cell (20th passage); Raji, human Burkitt's lymphoma; A.E, human artery endothelial cell; THP-1, human monocytic leukemia; CCD-29Lu, human lung emphysema; CAMA1, breast cancer; AN3CA, uterine cancer; SK.UT.1, uterine cancer; MG63, osteoblastoma; HOS, osteoblastoma; MCF7, breast cancer; OVCAR-3, ovarian cancer; CAOV-3, ovarian cancer; HUVE, human umbilical vein endothelial cell; AOSMIC, smooth muscle. The estimated message size is 6.5 kb. Panel B, VEGI expression in adult human tissues using multiple tissue Northern blots (Clonetech): Three separate blots were carried out. Positive results from any of the three experiments are shown.

Unlike other members of the TNF family, VEGI-$_{174}$ is specifically expressed in endothelial cells. Northern blotting analysis of total RNA preparations from 23 cell lines and primary cell cultures showed that VEGI was only detected in HUVE and human venous endothelial cells (FIG. 18). VEGI-$_{174}$ was also not seen in human artery endothelial cells. Using multiple tissue Northern blots, the VEGI-$_{174}$ transcript was found in many adult human tissues, including placenta, lung, skeletal muscle, kidney, pancreas, spleen, prostate, small intestine, and colon (FIG. 18), suggesting that the gene product may play a role in the function of a normal vasculature.

Example 29

Specific Inhibition of Endothelial Cell Growth by VEGI

Figure 19:
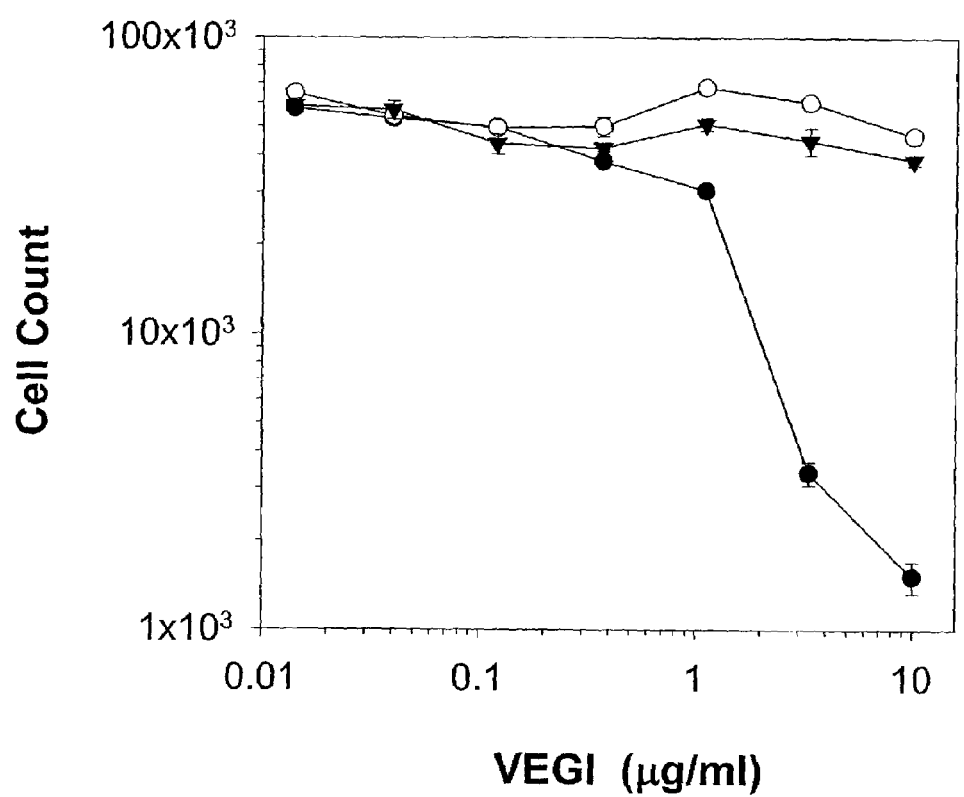
FIG. 19. Graph showing effect of VEGI on the proliferation of endothelial cell and breast cancer cells. The number of cells is plotted against VEGI concentration as indicated. Inhibition of the growth of ABAE cells (closed circles) but not that of MDA-MB-231 (open circles) or MDA-MB-435 (triangles) cells, is shown. Cancer cells and ABAE cells are seeded at 2000 and 8000 cells/well, respectively, in triplicate in 24-well plates. The culture media contained IMEM (Gibco) and 10% FCS. FGF-2 (1 ng/ml) is added to the media for ABAE cells. The cultures were maintained at 37° C., 5% $CO_2$, for 6 days. The cells are then trypsinized, and the number of cells determined by using a Coulter counter. One fifth of the total number of recovered ABAE cells is shown in order to normalize the comparison with the cancer cells.

A truncated version of VEGI-$_{174}$ was generated corresponding to the putative extracellular domain consisting of residues 39-174. The protein was expressed in *E. coli*, purified to apparent homogeneity as judged by SDS-polyacrylamide gel electrophoresis, and examined in a variety of cellular assays. The truncated protein was able to specifically inhibit the proliferation of adult bovine aortic endothelial (ABAE) cells (FIG. 19). Nearly complete inhibition of the growth of the endothelial cells was achieved at 10 µg/ml, with a half-maximum inhibitory concentration value ($IC_{50}$) of about 1 µg/ml (about 70 nM). In contrast, the protein had no effect on the growth of human breast cancer cells (MDA-MB-231 or MDA-MB-435) under similar experimental conditions (FIG. 19). VEGI also did not inhibit the proliferation of human T-cell leukemia cells (Jurkat), human Burkitts lymphoma cells (Raji), human monocytic leukemia cells (THP-1), or human promyelocytic leukemia cells (HL60), cells that are often responsive to the cytotoxic activity of the TNFs. The potency of VEGI appeared to be lower than what might be expected from a cytokine; however, it is comparable to that of known protein inhibitors of angiogenesis such as angiostatin and endostatin, as well as the CD40 ligand, (another TNF-family member). The relatively low potency of the truncated VEGI observed may also be partly due to an un-optimized truncation site, or the lack of post-translational modification, such as glycosylation, since the recombinant protein was expressed in E. coli.

Example 30

Up-regulation of VEGI Gene in Confluent Endothelial Cells

Figure 20:
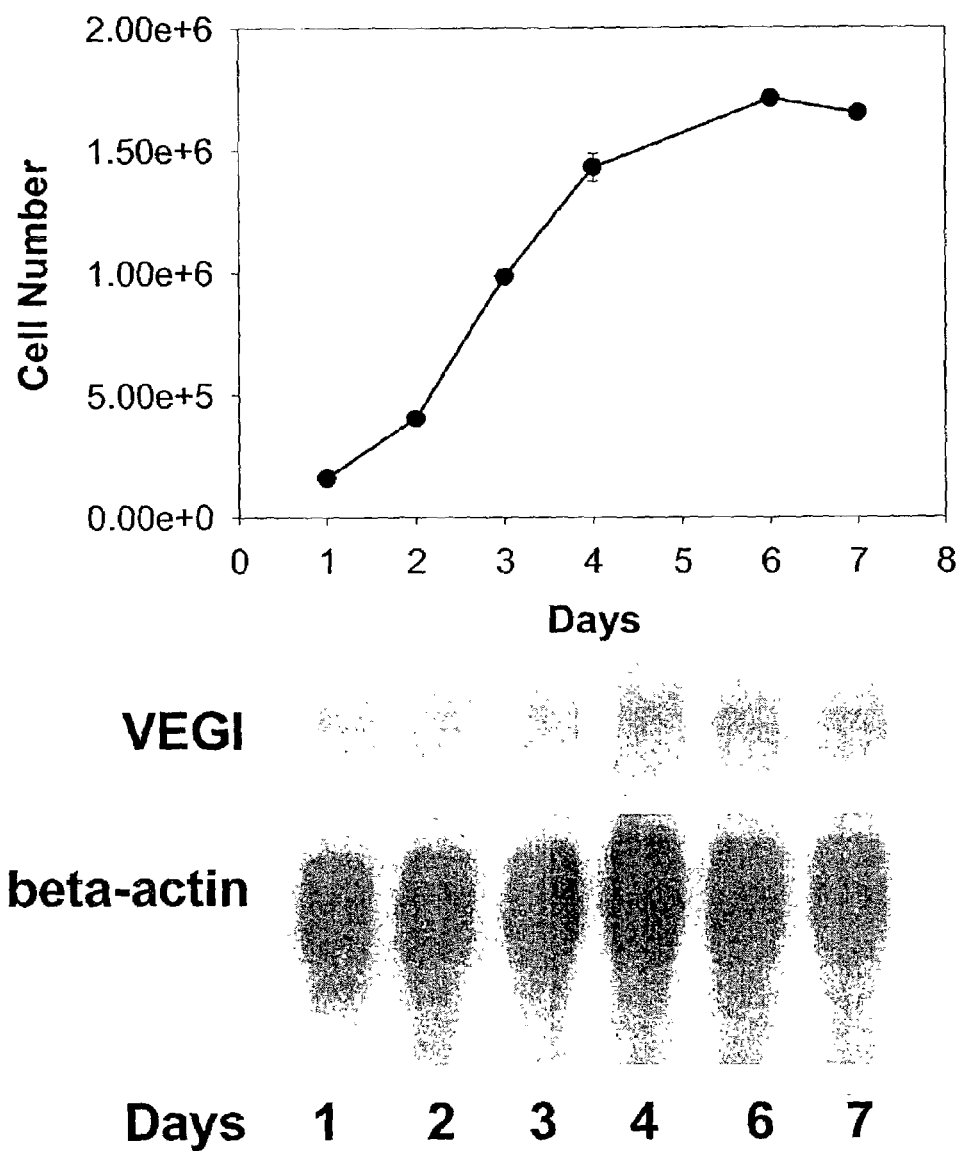
FIG. 20. Expression of VEGI in proliferating or quiescent endothelial cells. The VEGI mRNA levels in cultured HUVE cells are determined by Northern blotting analysis. Identical amount of total RNA (15 μg) is loaded on each lane, as indicated by the intensity of β-actin. Total RNA is prepared at the indicated time point (days post-seeding). The number of cells in each culture flask is determined simultaneously. The experiment is carried out in duplicate. Cells were seeded at 125,000 cells per flask (T-25) in IMEM, 10% FCS, 6 ng/ml FGF-2, and cultured at 37° C., 5% $CO_2$.

The endothelial cell-specific inhibitory activity of VEGI indicates that the protein acts as a negative regulator of angiogenesis. To show that the VEGI gene is down-regulated in proliferating endothelial cells but up-regulated when the cells are quiescent, the expression of VEGI in cultured HUVE cells was examined by Northern blotting (FIG. 20). Low levels of VEGI mRNA were seen in newly seeded HUVE cells; however, as the cell number increases in the cultures, the VEGI mRNA level increases accordingly, and reaches a plateau when the cell cultures become confluent.

Example 31

Figure 21:
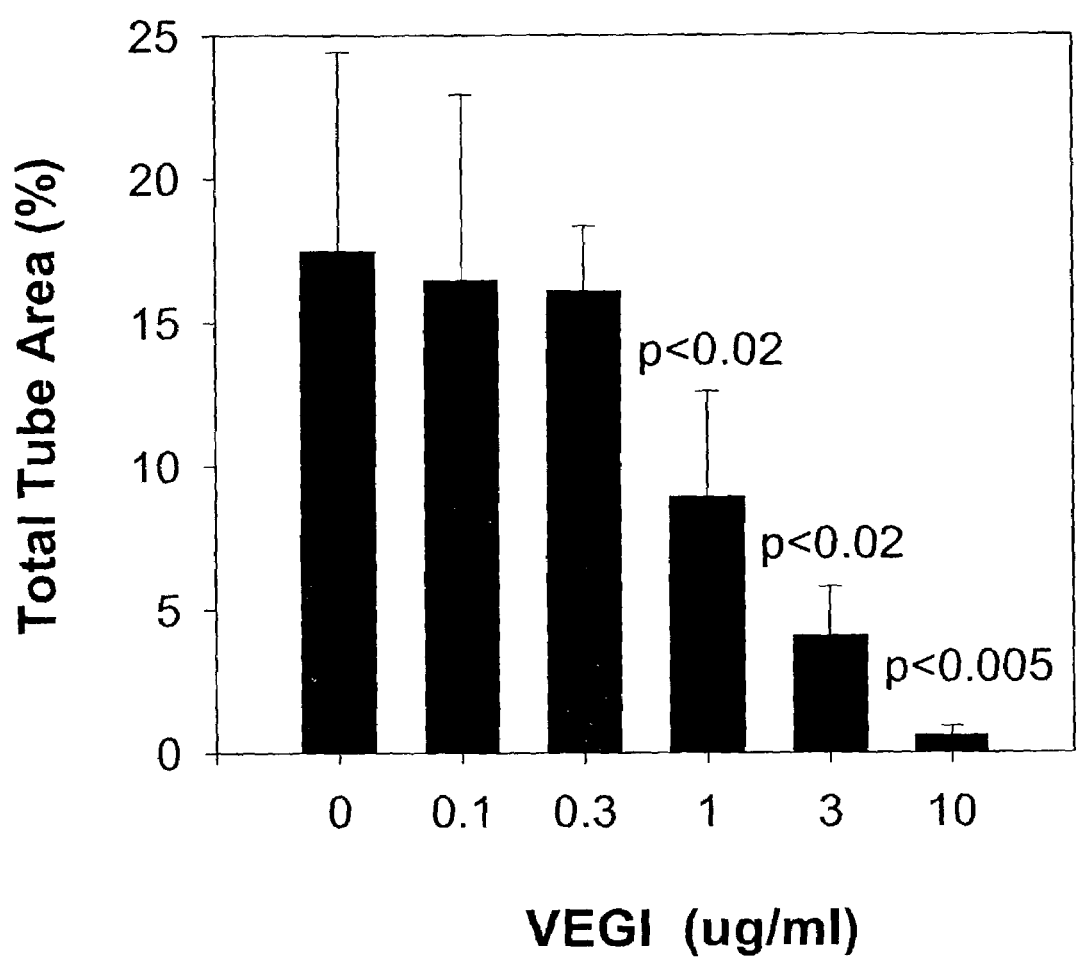
FIG. 21. Graph showing the effect of VEGI on the ability of ABAE cells to form capillary-like tubes on collagen gels. The ability of the recombinant VEGI to inhibit the formation of capillary-like tubes by ABAE cells is shown. The p-values (t-test) given above the columns is obtained by comparing the extent of the capillary-like tube formation by ABAE cells in the presence of various concentrations of VEGI, as indicated, to that when VEGI is absent from the culture media.

Inhibition of Capillary-like Tube Formation by Endothelial Cells Cultured on Collagen Gels The anti-angiogenic activity of the truncated VEGI was examined with an in vitro angiogenesis model (Montesano, R. & Oorci, L., Cell 42:469, 1985)). Endothelial cells cultured on the surface of a three-dimensional collagen gel form a quiescent monolayer when the culture reached confluence. Upon stimulation of the monolayer cells with an angiogenic factor such as FGF-2, however, the cells invaded into the gel and form capillary-like tubular structures in the gel. The tube-formation can be inhibited by anti-angiogenic factors. The extent of the tube formation can be quantitatively assessed by using computer-assisted image analysis (Li, L.Y., Biochemistry 33:10999, 1994). The truncated VEGI-$_{174}$ was able to inhibit the formation of capillary-like tubes by ABAE cells (FIG. 21). The $IC_{50}$ value for the inhibition was approximately 1 µg/ml, similar to that observed for the inhibition of endothelial cell growth.

Example 32

Figure 22:
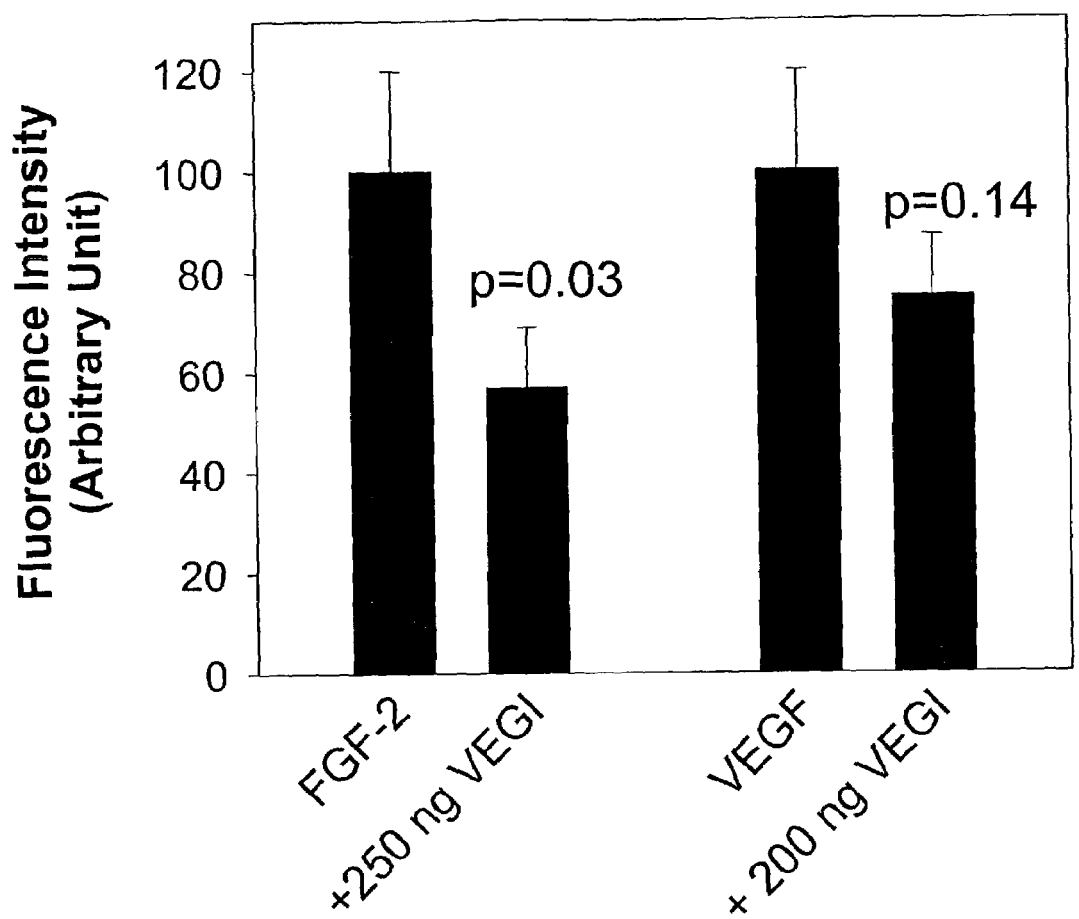
FIG. 22. Graph showing the inhibition of angiogenesis in collagen gels placed on chick embryonic chorioallantoic membrane (CAM) by VEGI. Growth of new capillary vessels into collagen gel pellets (0.05 ml) placed on the CAM is induced by either FGF-2 (100 ng) or VEGF (250 ng), embedded in the gels. The extent of angiogenesis in the gels is determined by evaluation of the fluorescence intensity of FTIC-dextran injected into the CAM circulation and retained in the gel. Inhibition of the capillary vessel growth by VEGI, indicated by a value lower than 100, is shown. The inhibitor is also embedded in the gels. Error bars represent the standard deviation of triplicate experimental values.

Inhibition of Capillary Growth in Collagen Gels Placed on Chick Embryo Chorioallantoic Membrane The antiangiogenic activity of VEGI-$_{174}$ was further demonstrated by using a modified chick embryo chorioallantoic membrane (CAM) assay (Nguyen, M. et al., Microvasc. Res. 47:31, 1994). The method is based on the growth of new capillary vessels into a collagen gel pellet placed on the CAM. Blood vessels were stimulated to grow vertically into a polymerized collagen gel in the presence of an angiogenic factor, such as FGF-2 or VEGF, embedded in the gel. The inhibitor was incorporated into the gels in order to determine its effect on the capillary growth. The extent of angiogenesis in the gel was assessed by the use of FITC-dextran injected into the circulation of the CAM. The recombinant VEGI-$_{174}$ (5.0 µg/ml) inhibited about 50% of the new capillary growth into the collagen gels induced by FGF-2 (2.0 µg/ml) (FIG. 22).

Example 33

Figure 23:
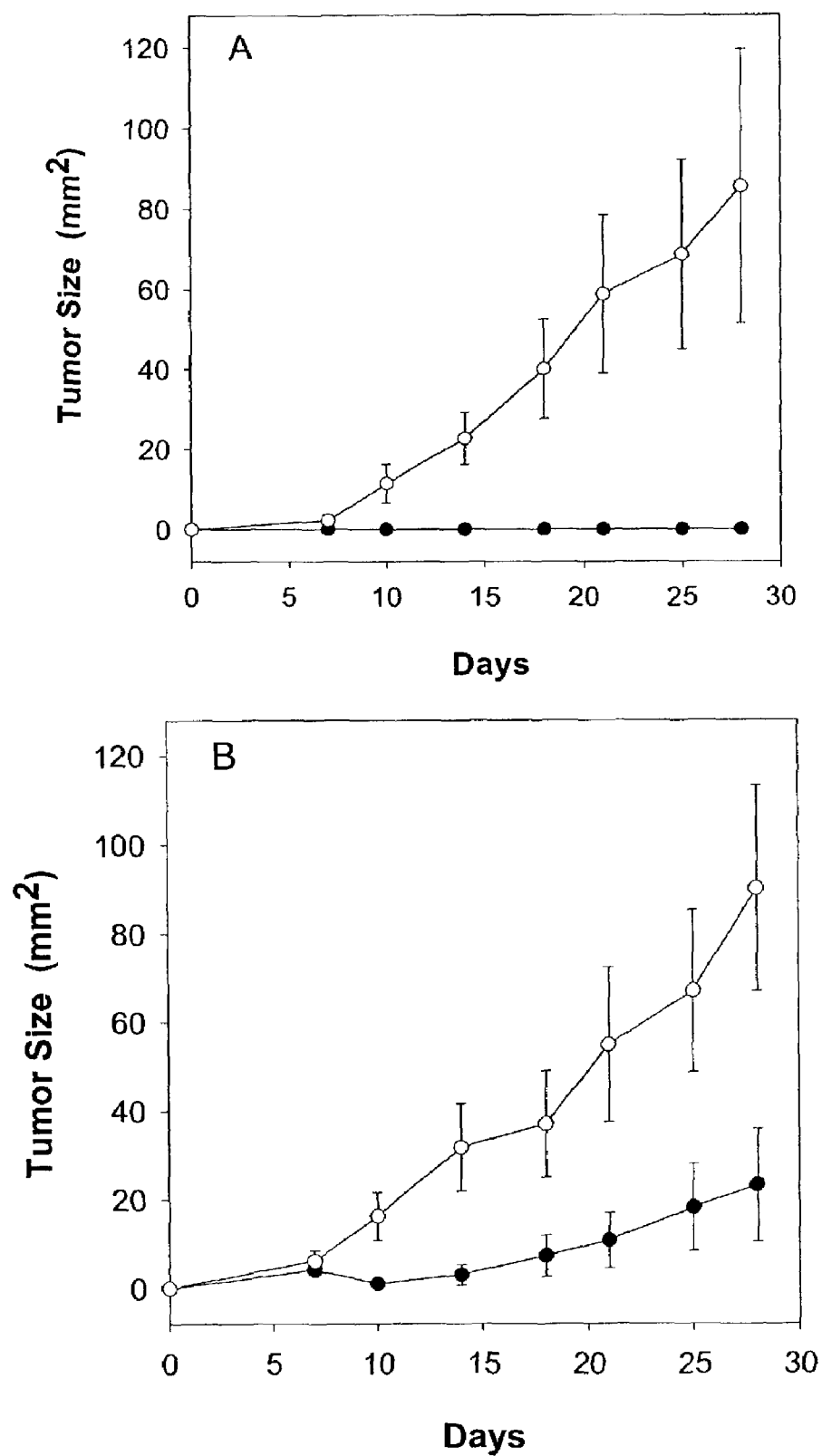
FIG. 23. Graph showing the inhibition of the growth of human breast cancer xenograft tumors in athymic nude mice by VEGI. Mixtures of VEGI-overexpressing or vector-transfected CHO cells ($5 \times 10^6$ cells per injection) and human breast cancer cells ($1 \times 10^6$ cells per injection) were injected into the mammary fat pads of female nude mice. Tumor sizes were monitored following injection. Panel A: Plot of the sizes of the MDA-MB-231 xenograft tumors ($mm^2$) as a function of time post-inoculation (days). Panel B: Plot of the sizes of the MDA-MB-435 xenograft tumors ($mm^2$) as a function of time post-inoculation (days). Open circles, co-inoculated with vector-transfected CHO cells. Closed circles, co-inoculated with the secreted VEGI transfected CHO cells.

Inhibition of Breast Cancer Xenograft Tumor Growth by Co-injected CHO Cells Overexpressing VEGI The anticancer activity of VEGI is demonstrated with a xenograft tumor model, using breast cancer cells that are highly tumorigenic when implanted into the mammary fat pads of female athymic nude mice. A secreted form of VEGI-$_{174}$ is constructed by replacing the N-terminal and the putative transmembrane segments of VEGI-$_{174}$ (residues 1-25) with the secretion signal peptide derived from human interleukin-6. The secreted VEGI-$_{174}$ construct was cloned into an eucaryotic expression vector, which was then transfected into Chinese hamster ovary (CHO) cells. Expression of the corresponding construct was confirmed by Northern blot analysis. Secretion of the modified VEGI by the transfected cells was confirmed by the ability of the conditioned medium to inhibit ABAE cell growth. The transfected CHO cells were then mixed with human breast cancer cells (MDA-MB-231 or MDA-MB-435), and the cell mixtures were injected into the mammary fat pads of nude mice. The growth of the xenograft tumors were monitored following injection. Despite the high tumorigenicity of the breast cancer cell lines used, a marked inhibition of the growth of the xenograft tumors formed by either the MDA-MB-231 (FIG. 23A) or the MDA-MB-435 cells (FIG. 23B) was observed. In a repeat of the experiment using the MDA-MB-435 cells, the co-injection also led to complete inhibition of tumor formation. The vector-transfected CHO cells had no effect on tumor growth in either case. Since VEGI did not inhibit the growth of these breast cancer cells in culture, the anticancer activity of the protein arised from its antiangiogenic activity.

Example 34

Inhibition of ABAE Cell Proliferation by VEGI-$_{192a}$

Full length VEGI-$_{192a}$ was expressed in E. coli and refolded and purified using method described in U.S. Pat. Appl. 20010044521 and PCT WO 01/55$_{174}$. Specifically, an expression vector (PET11, Novagen) containing a polynucleotide insert which encodes full length VEGI-$_{192a}$ polypeptide was constructed. The expression vector was transformed into E. coli and the transformed E. coli were grown to express the VEGI-$_{192a}$ polypeptide. The cells were harvested and inclusion bodies were purified from the disrupted cells. The $OD_{280}$ of the solution containing the inclusion bodies was adjusted to pH 5.0 with the 8 M urea solution. The final solution contained the following reducing reagents: 10 mM beta-Mercaptoethanol, 10 mM DTT (Dithiothreitol), 1 mM reduced glutathion (GSH), 0.1 mM oxidized glutathion (GSSG). The final pH of the solution was 10.0. The above solution was rapidly diluted into 20 volumes of 20 mM TRIS™ base, the pH was adjusted to 9.0, and then slowly adjusted to 8.0 with 1 M HCl, by adjusting pH to 8.8 for twenty four hours, then 8.6 for twenty four hours, etc., until the pH was 8.0. Alternatively, the proteins could be refolded using dialysis. The $OD_{280}$ of the 8 M urea solution was adjusted to 0.5, and dialyzed against 20 volumes of TRIS™ base. The pH of the solution was again slowly adjusted to 8.0. The refolded material was then concentrated by ultrafiltration, and separated by gel filtration, for example, on a SEPHACRYL™ S-300 column equilibrated with 20 mM TRIS™, HCl, 0.4 M urea, pH 8.0. The S-300 fractions could be checked by running a non-reduced SDS-PAGE. The wrongly refolded protein ran at a very high molecular weight, while properly refolded proteins ran at a normal molecular weight.

The VEGI-$_{192a}$ proteins from S-300 fractions were tested for its ability to inhibit endothelia cell growth. Adult bovine aortic endothelial (ABAE) cells were seeded in triplicate at 8,000 cells/well in 24-well plates, in IMEM (GIBCO, Gaithersburg, Md.), 10% fetal calf serum. FGF-2 (1 ng/ml) was added to the media. The cultures were maintained at 37° C., 5% $CO_2$, for 6 days. The cells were then trypsinized, and the number of cells determined by using a Coulter (Hialeah, Fla.) counter.

Figure 24:
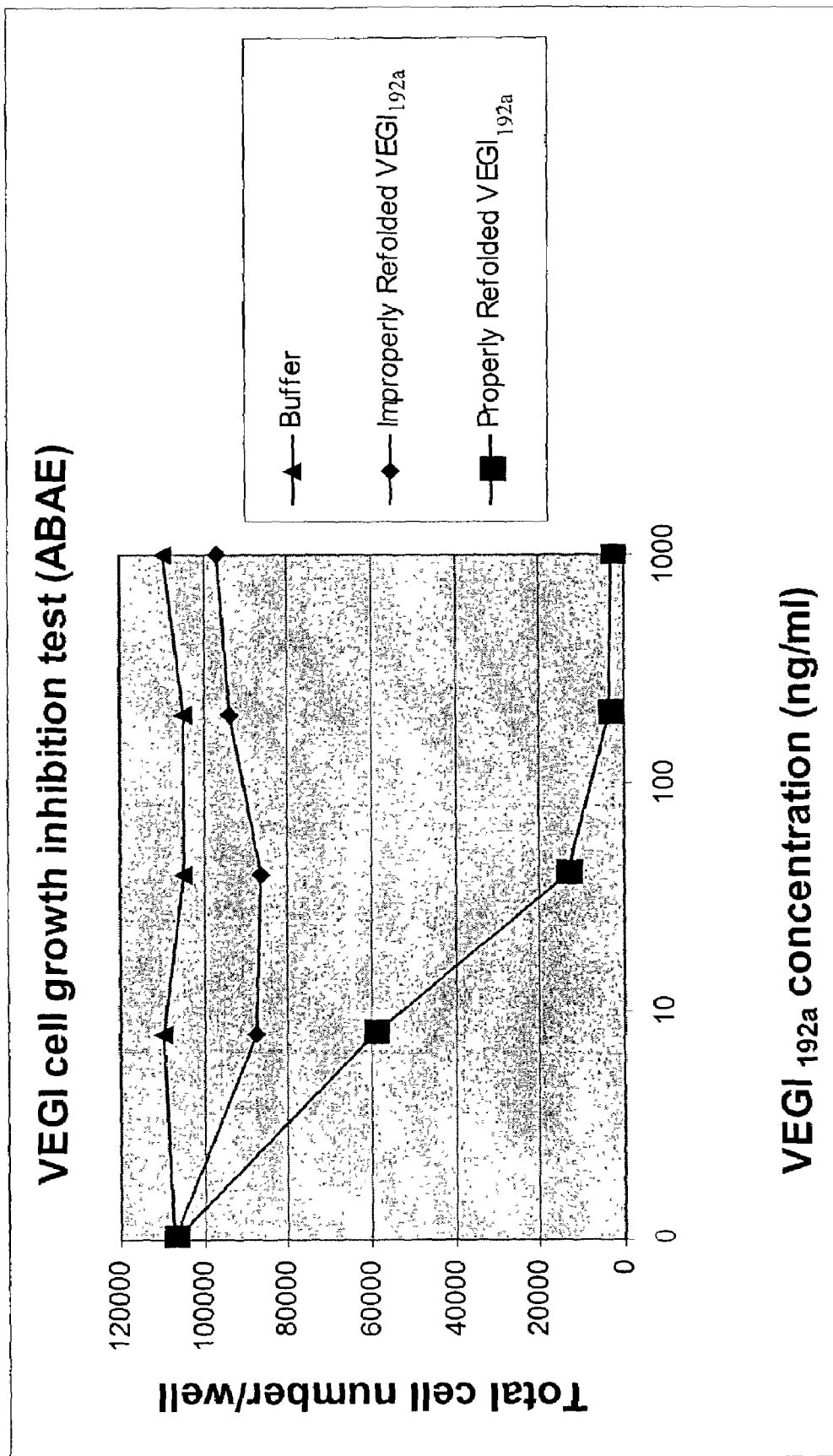
FIG. 24. Graph showing effect of $VEGI_{192a}$ on the proliferation of endothelial cells. Inhibition of the growth of ABAE cells by properly refolded $VEGI_{192a}$, but not improperly refolded $VEGI_{192a}$ or buffer, is shown. ABAE cells are seeded at 8000 cells/well, respectively, in triplicate in 24-well plates. The culture media contained IMEM (Gibco) and 10% FCS. FGF-2 (1 ng/ml) was added to the media for ABAE cells. The cultures were maintained at 37° C., 5% $CO_2$, for 6 days. The cells were then trypsinized, and the number of cells determined by using a Coulter counter. One fifth of the total number of recovered ABAE cells was shown in order to normalize the comparison with the cancer cells.

As shown in FIG. 24, properly folded VEGI-$_{192a}$, but not misfolded VEGI-$_{192a}$, from S-300 fractions was able to inhibit the growth of ABAE cells. Nearly half-complete inhibition of the growth of the endothelia cells was achieved at 1000 ng/ml, with a half-maximum inhibitory concentration value ($IC_{50}$) at about 10 ng/ml.

What is claimed is:

1. An isolated polypeptide comprising the amino acid sequence of SEQ ID NO:4.

2. A fusion protein comprising the polypeptide of claim 1 fused to another polypeptide.

3. The fusion protein of claim 2, wherein the polypeptide is fused to an amino acid sequence that facilitates purification of the polypeptide.

4. The fusion protein of claim 2, wherein the polypeptide is fused to an amino acid sequence encoding an epitope selected from the group consisting Myc, HA derived influenza virus hemagglutinin, and His-6.

5. A polypeptide produced by a method comprising expressing a polynucleotide comprising a nucleotide sequence encoding the amino acid sequence of SEQ ID NO:4 in *E. coli*.

6. The isolated polypeptide of claim 1, wherein the isolated polypeptide consists of the amino acid sequence of SEQ ID NO:4.

7. A composition comprising the polypeptide of claim 1.

8. A composition comprising the polypeptide of claim 6.

9. A composition comprising the polypeptide of claim 6, and further comprising a pharmaceutically acceptable excipient.

10. A composition comprising the polypeptide of claim 5.

* * * * *

```
                         SEQUENCE LISTING

<160> NUMBER OF SEQ ID NOS: 49

<210> SEQ ID NO 1
<211> LENGTH: 596
<212> TYPE: DNA
<213> ORGANISM: Homo Sapiens

<400> SEQUENCE: 1
ctcctatcat aggcgccatg caactcacaa agggccgtct tcatttcagt cacccttgt      60 ctcatacaaa gcacatttct ccttttgtta cagatgcacc tcttagagca gacggagata    120
agccaagggc acacctgaca gttgtgagac aaactcccac acagcacttt aaaaatcagt    180
tcccagctct gcactgggaa catgaactag gcctggcctt caccaagaac cgaatgaact    240
ataccaacaa attcctgctg atcccagagt cgggagacta cttcatttac tcccaggtca    300
cattccgtgg gatgacctct gagtgcagtg aaatcagaca agcaggccga ccaaacaagc    360
cagactccat cactgtggtc atcaccaagg taacagacag ctaccctgag ccaacccagc    420
tcctcatggg gaccaagtct gtatgcgaag taggtagcaa ctggttccag cccatctacc    480
tcggagccat gttctccttg caagaagggg acaagctaat ggtgaacgtc agtgacatct    540
ctttggtgga ttacacaaaa gaagataaaa ccttctttgg agccttctta ctatag        596

<210> SEQ ID NO 2
<211> LENGTH: 1025
<212> TYPE: DNA
<213> ORGANISM: Homo Sapiens
<220> FEATURE:
<221> NAME/KEY: misc_feature
<222> LOCATION: 992
<223> OTHER INFORMATION: n = A,T,C or G

<400> SEQUENCE: 2
ttaaacgggc cctctagact cgagcggccg ccactgtgct ggatatctgc agaattcggc     60
ttagcgcgtg aatcagatcg ggggggggg ttaagcaaag ccataaaact gtcagtttaa     120
tataccatca tttcactaac atgaagtgtg ccggctctgt cccccctttt cttttcctcc    180
ttccaactct tttaaaaaag aacagctcta cttacgccaa ggtggaattt tggctctact    240
agccactatt ctgcgacaga gtggctttgt tgacgtgaga aaggctctct ttgctttgcc    300
agaattagtc atggaaactt cacaggaaca ccagggcccc tcagatatac acagaatacc    360
atggagctgg ggacaaagga attcacatgc acctcttaga gcagacggag ataagccaag    420
ggcacacctg acagttgtga gacaaactcc cacacagcac tttaaaaatc agttcccagc    480
```

-continued

| | |
|---|---|
| tctgcactgg gaacatgaac taggcctggc cttcaccaag aaccgaatga actataccaa | 540 |
| caaattcctg ctgatcccag agtcgggaga ctacttcatt tactcccagg tcacattccg | 600 |
| tgggatgacc tctgagtgca gtgaaatcag acaagcaggc cgaccaaaca agccagactc | 660 |
| catcactgtg gtcatcacca aggtaacaga cagctaccct gagccaaccc agctcctcat | 720 |
| ggggaccaag tctgtatgcg aagtaggtag caactggttc cagcccatct acctcggagc | 780 |
| catgttctcc ttgcaagaag gggacaagct aatggtgaac gtcagtgaca tctctttggt | 840 |
| ggattacaca aaagaagata aaaccttctt tggagccttc ttactatagg atccggagcc | 900 |
| gaattccacc acactggact aagtggattc gagctcggta ccaaagctta gtttaaacg | 960 |
| ctagccagct tgggtccccc tatagtgagt cntattaatt tcgataagcc agtaagcagt | 1020 |
| gggtt | 1025 |

<210> SEQ ID NO 3
<211> LENGTH: 1421
<212> TYPE: DNA
<213> ORGANISM: Homo Sapiens
<220> FEATURE:
<221> NAME/KEY: misc_feature
<222> LOCATION: 1108, 1203, 1351, 1375, 1392, 1406
<223> OTHER INFORMATION: n = A,T,C or G

<400> SEQUENCE: 3

| | |
|---|---|
| ttgtaatacg actcactata gggcggccgc gaattcggca cgagatttaa tggccgagga | 60 |
| tctgggactg agctttgggg aaacagccag tgtggaaatg ctgccagagc acggcagctg | 120 |
| caggcccaag gccaggagca gcagcgcacg ctgggctctc acctgctgcc tggtgttgct | 180 |
| cccctccttt gcaggactca ccacataacct gcttgtcagc cagctccggg cccagggaga | 240 |
| ggcctgtgtg cagttccagg ctctaaaagg acaggagttt gcaccttcac atcagcaagt | 300 |
| ttatgcacct cttagagcag acggagataa gccaagggca cacctgacag ttgtgagaca | 360 |
| aactcccaca cagcacttta aaaatcagtt cccagctctg cactgggaac atgaactagg | 420 |
| cctggccttc accaagaacc gaatgaacta taccaacaaa ttcctgctga tcccagagtc | 480 |
| gggagactac ttcatttact cccaggtcac attccgtggg atgacctctg agtgcagtga | 540 |
| aatcagacaa gcaggccgac caaacaagcc agactccatc actgtggtca tcaccaaggt | 600 |
| aacagacagc taccctgagc caacccagct cctcatgggg accaagtctg tatgcgaagt | 660 |
| aggtagcaac tggttccagc ccatctacct cggagccatg ttctccttgc aagaagggga | 720 |
| caagctaatg gtgaacgtca gtgacatctc tttggtggat tacacaaaag aagataaaac | 780 |
| cttctttgga gccttcttac tataggagga gagcaaatat cattatatga aagtcctctg | 840 |
| ccaccgagtt cctaattttt ttgttcaaat gtaattataa ccaggggttt tcttggggcc | 900 |
| gggagtaggg ggcattccac agggacaacg gtttagctat gaaatttggg gcccaaaatt | 960 |
| tcacacttca tgtgccttac tgatgagagt actaactgga aaaaggctga agagagcaaa | 1020 |
| tatattatta agatgggttg gaggattggc gagtttctaa atattaagac actgatcact | 1080 |
| aaatgaatgg atgatctact cgggtcanga ttgaaagaga aatatttcaa caccttcctg | 1140 |
| ctatacaatg gtcaccagtg gtccagttat tgttcaattt gatcataaat tgcttcaatt | 1200 |
| cangagcttt gaaggaagtc caaggaaagc tctagaaaac agtataaact ttcgagggca | 1260 |
| aaatccttca ccaaatttc cacatacttt catgccctgc ctaaaaaaaa tgaaaagaa | 1320 |
| aagttggtat gtctcatgaa tgttcacaca naaagagttg ggttcatgtc atccncaaca | 1380 |
| tatgagaaaa anctaccttc ttttgnttat gtcacagatt c | 1421 |

<210> SEQ ID NO 4
<211> LENGTH: 192
<212> TYPE: PRT
<213> ORGANISM: Homo sapiens

<400> SEQUENCE: 4

Met Gln Leu Thr Lys Gly Arg Leu His Phe Ser His Pro Leu Ser His
1               5                   10                  15

Thr Lys His Ile Ser Pro Phe Val Thr Asp Ala Pro Leu Arg Ala Asp
            20                  25                  30

Gly Asp Lys Pro Arg Ala His Leu Thr Val Val Arg Gln Thr Pro Thr
        35                  40                  45

Gln His Phe Lys Asn Gln Phe Pro Ala Leu His Trp Glu His Glu Leu
    50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110

Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
    130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
                165                 170                 175

Val Asp Tyr Thr Lys Glu Asp Lys Thr Phe Phe Gly Ala Phe Leu Leu
            180                 185                 190

<210> SEQ ID NO 5
<211> LENGTH: 192
<212> TYPE: PRT
<213> ORGANISM: Homo sapiens

<400> SEQUENCE: 5

Met Glu Thr Ser Gln Glu His Gln Gly Pro Ser Asp Ile His Arg Ile
1               5                   10                  15

Pro Trp Ser Trp Gly Gln Arg Asn Ser His Ala Pro Leu Arg Ala Asp
            20                  25                  30

Gly Asp Lys Pro Arg Ala His Leu Thr Val Val Arg Gln Thr Pro Thr
        35                  40                  45

Gln His Phe Lys Asn Gln Phe Pro Ala Leu His Trp Glu His Glu Leu
    50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110

Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
    130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
            165                 170                 175

Val Asp Tyr Thr Lys Glu Asp Lys Thr Phe Phe Gly Ala Phe Leu Leu
        180                 185                 190

<210> SEQ ID NO 6
<211> LENGTH: 251
<212> TYPE: PRT
<213> ORGANISM: Homo Sapiens

<400> SEQUENCE: 6

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 7
<211> LENGTH: 174
<212> TYPE: PRT
<213> ORGANISM: Homo Sapiens

<400> SEQUENCE: 7

Met Arg Arg Phe Leu Ser Lys Val Tyr Ser Phe Pro Met Arg Lys Leu
1               5                   10                  15

Ile Leu Phe Leu Val Phe Pro Val Val Arg Gln Thr Pro Thr Gln His
            20                  25                  30

```
Phe Lys Asn Gln Phe Pro Ala Leu His Trp Glu His Glu Leu Gly Leu
             35                  40                  45

Ala Phe Thr Lys Asn Arg Met Asn Tyr Thr Asn Lys Phe Leu Leu Ile
 50                  55                  60

Pro Glu Ser Gly Asp Tyr Phe Ile Tyr Ser Gln Val Thr Phe Arg Gly
 65                  70                  75                  80

Met Thr Ser Glu Cys Ser Glu Ile Arg Gln Ala Gly Arg Pro Asn Lys
                 85                  90                  95

Pro Asp Ser Ile Thr Val Val Ile Thr Lys Val Thr Asp Ser Tyr Pro
                100                 105                 110

Glu Pro Thr Gln Leu Leu Met Gly Thr Lys Ser Val Cys Glu Val Gly
            115                 120                 125

Ser Asn Trp Phe Gln Pro Ile Tyr Leu Gly Ala Met Phe Ser Leu Gln
            130                 135                 140

Glu Gly Asp Lys Leu Met Val Asn Val Ser Asp Ile Ser Leu Val Asp
145                 150                 155                 160

Tyr Thr Lys Glu Asp Lys Thr Phe Phe Gly Ala Phe Leu Leu
                165                 170
```

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
cggaattcgt cactcagcg                                              19

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct

<400> SEQUENCE: 9
cccggatcct atagtaagaa ggctcc                                      26

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
agcgcgtgaa tcagatcg                                               18

<210> SEQ ID NO 11
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11
cggtggatcc cgagtttgtc tcacaactg                                   29

<210> SEQ ID NO 12
<211> LENGTH: 18

```
<212> TYPE: DNA
<213> ORGANISM: Artificial Sequence
<220> FEATURE:
<223> OTHER INFORMATION: Synthetic Construct

<400> SEQUENCE: 12
gtgtaatcca ccaaagag                                                     18

<210> SEQ ID NO 13
<211> LENGTH: 220
<212> TYPE: DNA
<213> ORGANISM: Homo Sapiens

<400> SEQUENCE: 13
caaagtaatt tgccccaggt cactagtcca agatgttatt ctctttgaac aaatgtgtat       60
gtccagtcac atattcttca ttcattcctc cccaaagcag tttttagctg ttaggtatat      120
tcgatcactt tagtctattt tgaaaatgat atgagacact ttttaagcaa agtctacagt      180
ttcccaatga gaaaattaat cctcctcctc tctcgggaac                            220

<210> SEQ ID NO 14
<211> LENGTH: 198
<212> TYPE: DNA
<213> ORGANISM: Homo Sapiens

<400> SEQUENCE: 14
gggggggggg gtcagaggtg cctggtgttg ctcccttcc ttgcaggact caccacatac        60
ctgcttgtca gccagctccg ggcccaggga gaggcctgtg tgcagttcca ggctctaaaa      120
ggacaggagt ttgcaccttc acatcagcaa gtttatgcac ctcttagagc agacggagat      180
aagccaaggg cacacctg                                                    198

<210> SEQ ID NO 15
<211> LENGTH: 137
<212> TYPE: DNA
<213> ORGANISM: Homo Sapiens

<400> SEQUENCE: 15
ctcctatcat aggcgccatg caactcacaa agggccgtct tcatttcagt cacccttttgt      60 ctcatacaaa gcacatttct cctttttgtta cagatgcacc tcttagagca gacggagata     120
agccaagggc acacctg                                                     137

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
atggccgagg atctgggact                                                   20

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
ctgcacacag gcctctccct g                                                 21
```

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct

<400> SEQUENCE: 18
ccttgcagga ctcaccacat acctgctt                                       28

<210> SEQ ID NO 19
<211> LENGTH: 30
<212> TYPE: DNA
<213> ORGANISM: Artificial Sequence
<220> FEATURE:
<223> OTHER INFORMATION: Synthetic Construct

<400> SEQUENCE: 19
agaggctagg tttccagtta aacccattga                                     30

<210> SEQ ID NO 20
<211> LENGTH: 30
<212> TYPE: DNA
<213> ORGANISM: Artificial Sequence
<220> FEATURE:
<223> OTHER INFORMATION: Synthetic Construct

<400> SEQUENCE: 20
tggggataac cttcagcctc atatttttta                                     30

<210> SEQ ID NO 21
<211> LENGTH: 30
<212> TYPE: DNA
<213> ORGANISM: Artificial Sequence
<220> FEATURE:
<223> OTHER INFORMATION: Synthetic Construct

<400> SEQUENCE: 21
atgtgaaggt gcaaactcct gtccttttag                                     30

<210> SEQ ID NO 22
<211> LENGTH: 30
<212> TYPE: DNA
<213> ORGANISM: Artificial Sequence
<220> FEATURE:
<223> OTHER INFORMATION: Synthetic Construct

<400> SEQUENCE: 22
gatctggagg gactgatgga gaagaaatgg                                     30

<210> SEQ ID NO 23
<211> LENGTH: 28
<212> TYPE: DNA
<213> ORGANISM: Artificial Sequence
<220> FEATURE:
<223> OTHER INFORMATION: Synthetic Construct

<400> SEQUENCE: 23
tacgtgccca gtagtgagat tgctagac                                       28

<210> SEQ ID NO 24
<211> LENGTH: 33
<212> TYPE: DNA
<213> ORGANISM: Artificial Sequence
<220> FEATURE:
<223> OTHER INFORMATION: Synthetic Construct -continued

<400> SEQUENCE: 24
gaggctgatg aaaaggagaa catagccatt att                     33

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
ctaaaaggac aggagtttgc a                                  21

<210> SEQ ID NO 26
<211> LENGTH: 19
<212> TYPE: DNA
<213> ORGANISM: Artificial Sequence
<220> FEATURE:
<223> OTHER INFORMATION: Synthetic Construct

<400> SEQUENCE: 26
ctgtaacaaa aggagaaat                                     19

<210> SEQ ID NO 27
<211> LENGTH: 19
<212> TYPE: DNA
<213> ORGANISM: Artificial Sequence
<220> FEATURE:
<223> OTHER INFORMATION: Synthetic Construct

<400> SEQUENCE: 27
atttctcctt ttgttacag                                     19

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
cttgaacagg cacagatgaa c                                  21

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
atctagttca tctgtgcctg ttca                               24

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
gggagtttgt ctcacaactg g                                  21

<210> SEQ ID NO 31

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
ccagttgtga gacaaactcc c                                              21

<210> SEQ ID NO 32
<211> LENGTH: 23
<212> TYPE: DNA
<213> ORGANISM: Artificial Sequence
<220> FEATURE:
<223> OTHER INFORMATION: Synthetic Construct

<400> SEQUENCE: 32
gtaaggcaca tgaagtgtga aat                                            23

<210> SEQ ID NO 33
<211> LENGTH: 1208
<212> TYPE: DNA
<213> ORGANISM: Homo Sapiens
<220> FEATURE:
<221> NAME/KEY: misc_feature
<222> LOCATION: 7, 12, 19, 26, 40, 51, 55, 71, 79, 90, 110, 131, 149,
      172, 204, 245, 248, 341, 350, 355, 405
<223> OTHER INFORMATION: n = A,T,C or G

<400> SEQUENCE: 33
tttttntttt tnctcaacnc ccccnatat ttataactgn atttggaccc ntgcntaacc     60
caacatatat ntttgaganc caaagggaan ttttaggttt tctcaagaan taatagacaa   120
acagaggccc ngagagggaa agggattcnc ccaaagtcat atagctaaag antagttccc   180
acccactctt catcccattt cttntggcca tctattcagt gaatatagtt aaagggccct   240 tgganganggg caaaaagcca attcactcct gtgaaagaat tttgtgggaa agagcagtga   300
gttgtgcttt attgagcatt ggccatgtgc aaaattcatg ntaagcaccn ccatntatac   360
tgtgcccatc ttagatgaga tgagaaaaca gggtctcagg caggntagat aaacttgccc   420
aaagccatgg ggccaagatt catttgtgtt caagactctt tcttgtgagt caccctgtcc   480
ttggtggtgc ttgctgcggg tgccacattc aatccaaaa tcctgcaagg agtggcactg   540
gaccaagctg gaggagatca aggtttctct cctatcatag gcgccatgca actcacaaag   600
ggccgtcttc atttcagtca cccttttgtct catacaaagc acatttctcc ttttgttaca   660
gatgcacatc ttagggcaga cggagataag ccaagggcac acttgacagt tgtgagacaa   720
actcccacac agcactttaa aaatcagttc ccagttctgc actgggaaca tgaactaggc   780
ctggccttca ccaagaaccg aatgaactat accaacaaat tcctgctgat cccagagtcg   840
ggagactact tcatttactc ccgggtcaca ttccgtggga tgacctctga gtgcagtgaa   900
atcagacaag caggccgacc aaacaagcca gactccatca ctgtggtcat caccaaggta   960
acagacagct accctgagcc aacccagctc tcatgggga ccaagtctgt gtgcgaagta  1020
ggtagcaact ggttccagcc catctacctc ggagccatgt tctccttgca agaaggggac  1080
aagctaatgg tgaacgtcag tgacatctct ttggtggatt acacaaaaga agataaaacc  1140
ttctttggag ccttcttact ataggaggag agcaaatatc attatatgaa agtcctctgc  1200
caccagcc                                                          1208

<210> SEQ ID NO 34
```

```
<211> LENGTH: 22
<212> TYPE: DNA
<213> ORGANISM: Homo Sapiens

<400> SEQUENCE: 34
agttcaggta agccacatgg ca                                              22

<210> SEQ ID NO 35
<211> LENGTH: 30
<212> TYPE: DNA
<213> ORGANISM: Homo Sapiens

<400> SEQUENCE: 35
cacatcagca agtttgtaag tatgctcatc                                      30

<210> SEQ ID NO 36
<211> LENGTH: 29
<212> TYPE: DNA
<213> ORGANISM: Homo Sapiens

<400> SEQUENCE: 36
gggcacacct gacagtaagc ctccctgct                                       29

<210> SEQ ID NO 37
<211> LENGTH: 29
<212> TYPE: DNA
<213> ORGANISM: Homo Sapiens

<400> SEQUENCE: 37
acaggaaaat ctcggataac cctttctttt                                      29

<210> SEQ ID NO 38
<211> LENGTH: 35
<212> TYPE: DNA
<213> ORGANISM: Homo Sapiens

<400> SEQUENCE: 38
ttttacttca cgtatgaaaa ctacacgatc tgtaa                                35

<210> SEQ ID NO 39
<211> LENGTH: 23
<212> TYPE: DNA
<213> ORGANISM: Homo Sapiens

<400> SEQUENCE: 39
tccacgtaga cattgttttc ctc                                             23

<210> SEQ ID NO 40
<211> LENGTH: 34
<212> TYPE: DNA
<213> ORGANISM: Homo Sapiens

<400> SEQUENCE: 40
tcctctcttt ctctctcccg actatcttag actt                                 34

<210> SEQ ID NO 41
<211> LENGTH: 23
<212> TYPE: DNA
<213> ORGANISM: Homo Sapiens

<400> SEQUENCE: 41
agagtgttga cagtccacac ggg                                             23
```

<210> SEQ ID NO 42
<211> LENGTH: 146
<212> TYPE: PRT
<213> ORGANISM: Homo Sapiens

<400> SEQUENCE: 42

Pro Thr Gln His Phe Lys Asn Gln Phe Pro Ala Leu His Trp Glu His
1               5                   10                  15

Glu Leu Gly Leu Ala Phe Thr Lys Asn Arg Met Asn Tyr Thr Asn Lys
            20                  25                  30

Phe Leu Leu Ile Pro Glu Ser Gly Asp Tyr Phe Ile Tyr Ser Gln Val
        35                  40                  45

Thr Phe Arg Gly Met Thr Ser Glu Cys Ser Glu Ile Arg Gln Ala Gly
    50                  55                  60

Arg Pro Asn Lys Pro Asp Ser Ile Thr Val Val Ile Thr Lys Val Thr
65                  70                  75                  80

Asp Ser Tyr Pro Glu Pro Thr Gln Leu Leu Met Gly Thr Lys Ser Val
                85                  90                  95

Cys Glu Val Gly Ser Asn Trp Phe Gln Pro Ile Tyr Leu Gly Ala Met
            100                 105                 110

Phe Ser Leu Gln Glu Gly Asp Lys Leu Met Val Asn Val Ser Asp Ile
        115                 120                 125

Ser Leu Val Asp Tyr Thr Lys Glu Asp Lys Thr Phe Phe Gly Ala Phe
    130                 135                 140

Leu Leu
145

<210> SEQ ID NO 43
<211> LENGTH: 21
<212> TYPE: DNA
<213> ORGANISM: Artificial Sequence
<220> FEATURE:
<223> OTHER INFORMATION: Synthetic Construct

<400> SEQUENCE: 43
aatctcacct gtctctgcct g                                        21

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
ctaaaccgtt gtccctgtgg                                          20

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
cctgtaaaaa tggtttatagt ag                                      22

<210> SEQ ID NO 46
<211> LENGTH: 17
<212> TYPE: DNA
<213> ORGANISM: Artificial Sequence
<220> FEATURE:

```
<223> OTHER INFORMATION: Synthetic Construct

<400> SEQUENCE: 46
ggtggcagag gactttc                                                  17

<210> SEQ ID NO 47
<211> LENGTH: 17
<212> TYPE: DNA
<213> ORGANISM: Artificial Sequence
<220> FEATURE:
<223> OTHER INFORMATION: Synthetic Construct

<400> SEQUENCE: 47
ctctacttac gccaagg                                                  17

<210> SEQ ID NO 48
<211> LENGTH: 26
<212> TYPE: DNA
<213> ORGANISM: Artificial Sequence
<220> FEATURE:
<223> OTHER INFORMATION: Synthetic Construct

<400> SEQUENCE: 48
cccggatcct atagtaagaa ggctcc                                        26

<210> SEQ ID NO 49
<211> LENGTH: 17
<212> TYPE: DNA
<213> ORGANISM: Artificial Sequence
<220> FEATURE:
<223> OTHER INFORMATION: Synthetic Construct

<400> SEQUENCE: 49
caccacatac ctgcttg                                                  17
```